US008486618B2

(12) United States Patent
Schenk et al.

(10) Patent No.: US 8,486,618 B2
(45) Date of Patent: Jul. 16, 2013

(54) HETEROGENEOUS INSEMINATE SYSTEM

(75) Inventors: John L. Schenk, Fort Collins, CO (US); George E. Seidel, Laporte, CO (US); Tae Kwang Suh, Fort Collins, CO (US); Juan F. Moreno, College Station, TX (US); Maurice A. Rosenstein, Navasota, TX (US)

(73) Assignee: XY, LLC, Navasota, TX (US)

( * ) Notice: Subject to any disclaimer, the term of this patent is extended or adjusted under 35 U.S.C. 154(b) by 28 days.

(21) Appl. No.: 13/185,400

(22) Filed: Jul. 18, 2011

(65) Prior Publication Data

US 2011/0275052 A1    Nov. 10, 2011

Related U.S. Application Data

(63) Continuation-in-part of application No. 12/806,945, filed on Aug. 24, 2010, which is a continuation of application No. 10/523,268, filed as application No. PCT/US03/24460 on Aug. 1, 2003, now Pat. No. 8,211,629.

(60) Provisional application No. 60/400,971, filed on Aug. 1, 2002.

(51) Int. Cl.
*A01N 1/02* (2006.01)
*G01N 33/00* (2006.01)
*A61B 17/43* (2006.01)
*A61D 7/00* (2006.01)

(52) U.S. Cl.
USPC .................. 435/2; 422/73; 600/33; 600/35

(58) Field of Classification Search
USPC ................................ 435/2; 422/73; 600/33, 35
See application file for complete search history.

(56) References Cited

U.S. PATENT DOCUMENTS

| | | |
|---|---|---|
| 3,005,756 A | 10/1961 | VanDenmark et al. |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister |
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter et al. |
| 3,791,517 A | 2/1974 | Friedman |
| 3,810,010 A | 5/1974 | Thom |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,906,929 A | 9/1975 | Augspurger |
| 3,909,744 A | 9/1975 | Wisner et al. |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| RE29,141 E | 2/1977 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |
| 4,092,229 A | 5/1978 | Bhattacharya |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |

(Continued)

FOREIGN PATENT DOCUMENTS

| BR | 9704313 | 6/1999 |
|---|---|---|
| CA | 1029833 | 4/1978 |

(Continued)

OTHER PUBLICATIONS

Beatty. J Genetics 55(2):325-347, 1957; abstract.*
Stahlberg et al. Theriogenology 53:1365-1373, 2000.*
Rath et al. J Anim Sci 77:3346-3352, 1999.*
Azmal et al. Relative merits of homo and heterospermic bull semen in respect of preservation quality. Pakistan Journal of Biol. Sci., Nov. 2004, vol. 7, pp. 1908-1911.
Beatty. Fertility of mixed semen from different rabbits. Journal or Reprod. Fertil. Feb. 1960, vol. 1, pp. 52-60.
U.S. Appl. No. 12/806,945, filed Aug. 24, 2010.
U.S. Appl. No. 10/523,268, filed Jul. 7, 2005.

(Continued)

*Primary Examiner* — Marcia S Noble

(74) *Attorney, Agent, or Firm* — Craig R. Miles; CR Miles, P.C.

(57) ABSTRACT

A heterogeneous inseminate including a first amount of sperm of a first animal and a second amount of sperm of a second animal of the same species, the first amount of sperm and the second amount of sperm sex-selected sperm of the same sex, useful in the in-vivo or in-vitro fertilization of an egg of a female animal of the same species for the production of sex-selected embryos and sex-selected offspring.

28 Claims, 7 Drawing Sheets

U.S. PATENT DOCUMENTS

| | | |
|---|---|---|
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |
| 4,225,405 A | 9/1980 | Lawson |
| 4,230,558 A | 10/1980 | Fulwyler |
| 4,251,733 A | 2/1981 | Hirleman, Jr. |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| RE32,350 E | 2/1987 | Bhattacharya |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaudier |
| 4,680,258 A | 7/1987 | Hammerling et al. |
| 4,683,195 A | 7/1987 | Mullis et al. |
| 4,683,202 A | 7/1987 | Mullis |
| 4,683,213 A | 7/1987 | Ax |
| 4,691,829 A | 9/1987 | Auer |
| 4,698,142 A | 10/1987 | Muroi et al. |
| 4,702,598 A | 10/1987 | Boehmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | Van den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junilla |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,989,977 A | 2/1991 | North, Jr. |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | De Grooth |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |
| 5,138,181 A | 8/1992 | Lefevre et al. |
| 5,142,140 A | 8/1992 | Yamazaki et al. |
| 5,142,462 A | 8/1992 | Kashima |
| 5,144,224 A | 9/1992 | Larsen |
| 5,150,313 A | 9/1992 | Van den Engh et al. |
| 5,158,889 A | 10/1992 | Hirako et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,204,884 A | 4/1993 | Leary et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |

| Patent | Date | Inventor |
|---|---|---|
| 5,260,764 A | 11/1993 | Fukuda et al. |
| 5,274,240 A | 12/1993 | Mathies et al. |
| 5,275,787 A | 1/1994 | Yuguchi et al. |
| 5,298,967 A | 3/1994 | Wells |
| 5,315,122 A | 5/1994 | Pinsky et al. |
| 5,316,540 A | 5/1994 | McMannis et al. |
| 5,317,162 A | 5/1994 | Pinsky et al. |
| 5,346,990 A | 9/1994 | Spaulding |
| RE34,782 E | 11/1994 | Dandliker et al. |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. |
| 5,395,588 A | 3/1995 | North, Jr. et al. |
| 5,400,179 A | 3/1995 | Ito |
| 5,412,466 A | 5/1995 | Ogino |
| 5,437,987 A | 8/1995 | Teng et al. |
| 5,439,362 A | 8/1995 | Spaulding |
| 5,444,527 A | 8/1995 | Kosaka |
| 5,447,841 A | 9/1995 | Gray et al. |
| 5,447,842 A | 9/1995 | Simons |
| 5,452,054 A | 9/1995 | Dewa et al. |
| 5,457,526 A | 10/1995 | Kosaka |
| 5,461,145 A | 10/1995 | Kudo et al. |
| 5,464,581 A | 11/1995 | Van den Engh |
| 5,466,572 A | 11/1995 | Sasaki et al. |
| 5,467,189 A | 11/1995 | Kreikebaum et al. |
| 5,469,375 A | 11/1995 | Kosaka |
| 5,471,294 A | 11/1995 | Ogino |
| 5,471,299 A | 11/1995 | Kaye et al. |
| 5,475,487 A | 12/1995 | Mariella, Jr. et al. |
| 5,480,774 A | 1/1996 | Hew et al. |
| 5,480,775 A | 1/1996 | Ito et al. |
| 5,483,469 A | 1/1996 | Van den Engh et al. |
| 5,488,469 A | 1/1996 | Yamamoto et al. |
| 5,492,534 A | 2/1996 | Atheyde |
| 5,494,795 A | 2/1996 | Guerry et al. |
| 5,495,719 A | 3/1996 | Gray, Jr. |
| 5,496,272 A | 3/1996 | Chung et al. |
| 5,503,994 A | 4/1996 | Shear et al. |
| 5,514,537 A | 5/1996 | Chandler |
| 5,523,573 A | 6/1996 | Hanninen et al. |
| 5,532,155 A | 7/1996 | Ranoux |
| 5,547,849 A | 8/1996 | Baer et al. |
| 5,548,395 A | 8/1996 | Kosaka |
| 5,548,661 A | 8/1996 | Price et al. |
| 5,550,058 A | 8/1996 | Corio et al. |
| 5,556,764 A | 9/1996 | Sizto et al. |
| 5,558,998 A | 9/1996 | Hammond et al. |
| 5,559,032 A | 9/1996 | Pomeroy et al. |
| 5,569,581 A | 10/1996 | Killian et al. |
| 5,578,449 A | 11/1996 | Frasch et al. |
| 5,579,159 A | 11/1996 | Ito |
| 5,584,982 A | 12/1996 | Dovichi et al. |
| 5,589,457 A | 12/1996 | Wiltbank |
| 5,596,401 A | 1/1997 | Kusuzawa |
| 5,601,234 A | 2/1997 | Larue |
| 5,601,235 A | 2/1997 | Booker et al. |
| 5,601,533 A | 2/1997 | Hancke et al. |
| 5,602,039 A | 2/1997 | Van den Engh |
| 5,602,349 A | 2/1997 | Van den Engh |
| 5,608,519 A | 3/1997 | Gourley et al. |
| 5,620,842 A | 4/1997 | Davis et al. |
| 5,622,820 A | 4/1997 | Rossi |
| 5,627,037 A | 5/1997 | Ward et al. |
| 5,633,503 A | 5/1997 | Kosaka |
| 5,641,457 A | 6/1997 | Vardanega |
| 5,643,796 A | 7/1997 | Van Den Engh et al. |
| 5,650,847 A | 7/1997 | Maltsev et al. |
| 5,658,751 A | 8/1997 | Yue et al. |
| 5,660,997 A | 8/1997 | Spaulding |
| 5,663,048 A | 9/1997 | Winkfein et al. |
| 5,665,315 A | 9/1997 | Robert et al. |
| 5,672,880 A | 9/1997 | Kain |
| 5,674,743 A | 10/1997 | Ulmer |
| 5,675,401 A | 10/1997 | Wangler et al. |
| 5,682,038 A | 10/1997 | Hoffman |
| 5,684,575 A | 11/1997 | Steen |
| 5,687,727 A | 11/1997 | Kraus et al. |
| 5,690,815 A | 11/1997 | Krasnoff et al. |
| 5,690,895 A | 11/1997 | Matsumoto et al. |
| 5,691,133 A | 11/1997 | Critser et al. |
| 5,693,534 A | 12/1997 | Alak et al. |
| 5,696,157 A | 12/1997 | Wang et al. |
| 5,699,152 A | 12/1997 | Fedor et al. |
| 5,700,692 A | 12/1997 | Sweet |
| 5,701,012 A | 12/1997 | Ho |
| 5,707,808 A | 1/1998 | Roslaniec et al. |
| 5,708,868 A | 1/1998 | Ishikawa |
| 5,712,807 A | 1/1998 | Bangham |
| 5,719,666 A | 2/1998 | Fukuda et al. |
| 5,719,667 A | 2/1998 | Miers |
| 5,726,009 A | 3/1998 | Connors et al. |
| 5,726,364 A | 3/1998 | Van den Engh |
| 5,726,751 A | 3/1998 | Altendorf et al. |
| 5,730,941 A | 3/1998 | Lefevre et al. |
| 5,736,330 A | 4/1998 | Fulton |
| 5,739,902 A | 4/1998 | Gjelsnes et al. |
| 5,745,308 A | 4/1998 | Spangenberg |
| 5,747,349 A | 5/1998 | Vanden Engh et al. |
| 5,759,767 A | 6/1998 | Lakowicz et al. |
| 5,770,363 A | 6/1998 | Brown |
| 5,777,732 A | 7/1998 | Hanninen et al. |
| 5,780,230 A | 7/1998 | Li et al. |
| 5,786,560 A | 7/1998 | Tatah et al. |
| 5,790,692 A | 8/1998 | Price et al. |
| 5,793,485 A | 8/1998 | Gourley |
| 5,796,112 A | 8/1998 | Ichie |
| 5,798,276 A | 8/1998 | Haugland et al. |
| 5,799,830 A | 9/1998 | Carroll et al. |
| 5,804,436 A | 9/1998 | Okun et al. |
| 5,815,262 A | 9/1998 | Schrof et al. |
| 5,819,948 A | 10/1998 | Van den Engh |
| 5,824,269 A | 10/1998 | Kosaka et al. |
| 5,831,723 A | 11/1998 | Kubota et al. |
| 5,835,262 A | 11/1998 | Iketaki et al. |
| 5,840,504 A | 11/1998 | Blecher |
| 5,844,685 A | 12/1998 | Gontin |
| 5,846,737 A | 12/1998 | Kang |
| 5,866,344 A | 2/1999 | Georgiou |
| 5,868,767 A | 2/1999 | Farley et al. |
| 5,872,627 A | 2/1999 | Miers |
| 5,873,254 A | 2/1999 | Arav |
| 5,874,266 A | 2/1999 | Paisson |
| 5,876,942 A | 3/1999 | Cheng et al. |
| 5,880,457 A | 3/1999 | Tomiyama et al. |
| 5,880,474 A | 3/1999 | Norton et al. |
| 5,883,378 A | 3/1999 | Irish et al. |
| 5,888,730 A | 3/1999 | Gray et al. |
| 5,891,734 A | 4/1999 | Gill et al. |
| 5,893,843 A | 4/1999 | Rodrigues Claro |
| 5,895,764 A | 4/1999 | Sklar et al. |
| 5,895,922 A | 4/1999 | Ho |
| 5,899,848 A | 5/1999 | Haubrich |
| 5,909,278 A | 6/1999 | Deka et al. |
| 5,912,257 A | 6/1999 | Prasad et al. |
| 5,916,144 A | 6/1999 | Prather et al. |
| 5,916,449 A | 6/1999 | Ellwart et al. |
| 5,917,733 A | 6/1999 | Bangham |
| 5,919,360 A | 7/1999 | Contaxis, III et al. |
| 5,919,621 A | 7/1999 | Brown |
| 5,934,885 A | 8/1999 | Farrell et al. |
| 5,962,238 A | 10/1999 | Sizto et al. |
| 5,972,592 A | 10/1999 | Suarez |
| 5,972,710 A | 10/1999 | Weigl et al. |
| 5,973,842 A | 10/1999 | Spangenberg |
| 5,985,216 A | 11/1999 | Rens et al. |
| 5,985,538 A | 11/1999 | Stachecki |
| 5,990,479 A | 11/1999 | Weiss et al. |
| 5,991,028 A | 11/1999 | Cabib et al. |
| 5,998,140 A | 12/1999 | Dervan et al. |
| 5,998,212 A | 12/1999 | Corio et al. |
| 6,002,471 A | 12/1999 | Quake |
| 6,003,678 A | 12/1999 | Van den Engh |
| 6,042,025 A | 3/2000 | Crampton et al. |
| 6,042,249 A | 3/2000 | Spangenberg |
| 6,050,935 A | 4/2000 | Ranoux et al. |

| | | | | | | | |
|---|---|---|---|---|---|---|---|
| 6,071,689 | A | 6/2000 | Seidel et al. | 6,537,829 | B1 | 3/2003 | Zarling et al. |
| 6,079,836 | A | 6/2000 | Burr et al. | 6,540,895 | B1 | 4/2003 | Spence et al. |
| 6,086,574 | A | 7/2000 | Carroll et al. | 6,563,583 | B2 | 5/2003 | Ortyn et al. |
| 6,087,352 | A | 7/2000 | Trout | 6,576,291 | B2 | 6/2003 | Bawendi et al. |
| 6,090,947 | A | 7/2000 | Dervan et al. | 6,577,387 | B2 | 6/2003 | Ross, III et al. |
| 6,097,485 | A | 8/2000 | Lievan | 6,580,504 | B1 | 6/2003 | Ortyn et al. |
| 6,111,398 | A | 8/2000 | Graham | 6,587,203 | B2 | 7/2003 | Colon |
| 6,117,068 | A | 9/2000 | Gourley et al. | 6,589,792 | B1 | 7/2003 | Malachowski |
| 6,119,465 | A | 9/2000 | Mullens et al. | 6,590,911 | B1 | 7/2003 | Spinelli et al. |
| 6,120,735 | A | 9/2000 | Zborowski et al. | 6,596,143 | B1 | 7/2003 | Wang et al. |
| 6,128,133 | A | 10/2000 | Bergmann | 6,596,499 | B2 | 7/2003 | Jalink |
| 6,130,034 | A | 10/2000 | Aitken | 6,604,435 | B2 | 8/2003 | Buchanan et al. |
| 6,132,961 | A | 10/2000 | Gray et al. | 6,613,525 | B2 | 9/2003 | Nelson et al. |
| 6,133,044 | A | 10/2000 | Van den Engh | 6,617,107 | B1 | 9/2003 | Dean |
| 6,133,995 | A | 10/2000 | Kubota | 6,618,143 | B2 | 9/2003 | Roche et al. |
| 6,139,800 | A | 10/2000 | Chandler | 6,618,679 | B2 | 9/2003 | Loehrlein et al. |
| 6,140,121 | A | 10/2000 | Ellington et al. | 6,641,708 | B1 | 11/2003 | Becker et al. |
| 6,143,535 | A | 11/2000 | Paisson | 6,642,018 | B1 | 11/2003 | Koller et al. |
| 6,143,901 | A | 11/2000 | Dervan | 6,658,357 | B2 | 12/2003 | Chandler |
| 6,146,837 | A | 11/2000 | van de Winkel | 6,664,550 | B2 | 12/2003 | Rader et al. |
| 6,149,867 | A | 11/2000 | Seidel et al. | 6,667,830 | B1 | 12/2003 | Iketaki et al. |
| 6,153,373 | A | 11/2000 | Benjamin et al. | 6,671,044 | B2 | 12/2003 | Ortyn et al. |
| 6,154,276 | A | 11/2000 | Mariella, Jr. | 6,673,095 | B2 | 1/2004 | Nordquist |
| 6,175,409 | B1 | 1/2001 | Nielsen et al. | 6,674,525 | B2 | 1/2004 | Bardell et al. |
| 6,177,277 | B1 | 1/2001 | Soini | 6,698,627 | B2 | 3/2004 | Garcia et al. |
| 6,193,647 | B1 | 2/2001 | Beebe et al. | 6,700,130 | B2 | 3/2004 | Fritz |
| 6,201,628 | B1 | 3/2001 | Basiji et al. | 6,703,621 | B2 | 3/2004 | Wolleschensky |
| 6,207,392 | B1 | 3/2001 | Weiss et al. | 6,704,313 | B1 | 3/2004 | Duret et al. |
| 6,208,411 | B1 | 3/2001 | Vaez-Iravani | 6,706,163 | B2 | 3/2004 | Saul et al. |
| 6,211,477 | B1 | 4/2001 | Cardott et al. | 6,707,555 | B1 | 3/2004 | Kusuzawa et al. |
| 6,214,560 | B1 | 4/2001 | Yguerabide et al. | 6,713,019 | B2 | 3/2004 | Ozasa et al. |
| 6,221,654 | B1 | 4/2001 | Quake et al. | 6,729,369 | B2 | 5/2004 | Neas et al. |
| 6,221,671 | B1 | 4/2001 | Groner et al. | 6,746,873 | B1 | 6/2004 | Buchanan et al. |
| 6,238,920 | B1 | 5/2001 | Nagai et al. | 6,752,298 | B2 | 6/2004 | Garcia et al. |
| 6,247,323 | B1 | 6/2001 | Maeda | 6,753,161 | B2 | 6/2004 | Koller et al. |
| 6,248,590 | B1 | 6/2001 | Malachowski | 6,761,286 | B2 | 7/2004 | Py et al. |
| 6,256,096 | B1 | 7/2001 | Johnson | 6,761,288 | B2 | 7/2004 | Garcia |
| 6,263,745 | B1 | 7/2001 | Buchanan et al. | 6,767,706 | B2 | 7/2004 | Quake |
| 6,283,920 | B1 | 9/2001 | Eberle et al. | 6,780,377 | B2 | 8/2004 | Hall et al. |
| 6,296,810 | B1 | 10/2001 | Ulmer | 6,782,768 | B2 | 8/2004 | Buchanan et al. |
| 6,309,815 | B1 | 10/2001 | Tash et al. | 6,789,706 | B2 | 9/2004 | Abergel et al. |
| 6,316,234 | B1 | 11/2001 | Bova | 6,789,750 | B1 | 9/2004 | Heldt |
| 6,317,511 | B1 | 11/2001 | Horiuchi | 6,793,387 | B1 | 9/2004 | Neas et al. |
| 6,322,901 | B1 | 11/2001 | Bawendi et al. | 6,813,017 | B1 | 11/2004 | Hoffman et al. |
| 6,323,632 | B1 | 11/2001 | Husher et al. | 6,819,411 | B1 | 11/2004 | Sharpe et al. |
| 6,326,144 | B1 | 12/2001 | Bawendi et al. | 6,849,394 | B2 | 2/2005 | Rozenboom et al. |
| 6,328,071 | B1 | 12/2001 | Austin | 6,849,423 | B2 | 2/2005 | Mutz et al. |
| 6,329,158 | B1 | 12/2001 | Hoffman et al. | 6,861,265 | B1 | 3/2005 | Van den Engh |
| 6,332,540 | B1 | 12/2001 | Paul et al. | 6,941,005 | B2 | 9/2005 | Lary et al. |
| 6,357,307 | B2 | 3/2002 | Buchanan et al. | 7,015,310 | B2 | 3/2006 | Remington et al. |
| 6,368,786 | B1 | 4/2002 | Saint-Ramon et al. | 7,024,316 | B1 | 4/2006 | Ellison et al. |
| 6,372,422 | B1 | 4/2002 | Seidel et al. | 7,070,917 | B1 | 7/2006 | Christensen et al. |
| 6,372,506 | B1 | 4/2002 | Norton | 7,094,527 | B2 | 8/2006 | Seidel et al. |
| 6,384,951 | B1 | 5/2002 | Basiji et al. | 7,105,355 | B2 | 9/2006 | Kurabayashi et al. |
| 6,395,305 | B1 | 5/2002 | Buhr et al. | 7,169,548 | B2 | 1/2007 | Maxwell et al. |
| 6,400,453 | B1 | 6/2002 | Hansen | 7,195,920 | B2 | 3/2007 | Seidel et al. |
| 6,411,835 | B1 | 6/2002 | Modell et al. | 7,208,265 | B1 | 4/2007 | Schenk |
| 6,411,904 | B1 | 6/2002 | Chandler | 7,221,453 | B2 | 5/2007 | Sharpe et al. |
| 6,416,190 | B1 | 7/2002 | Grier et al. | 7,371,517 | B2 | 5/2008 | Evans et al. |
| 6,423,505 | B1 | 7/2002 | Davis | 7,723,116 | B2 | 5/2010 | Evans et al. |
| 6,423,551 | B1 | 7/2002 | Weiss et al. | 7,758,811 | B2 | 7/2010 | Durack et al. |
| 6,432,630 | B1 | 8/2002 | Blankenstein | 7,943,384 | B2 | 5/2011 | Durack et al. |
| 6,432,638 | B2 | 8/2002 | Dervan et al. | 8,251,887 | B2 | 8/2012 | Li et al. |
| 6,452,372 | B1 | 9/2002 | Husher et al. | 2001/0006416 | A1 | 7/2001 | Johnson |
| 6,454,945 | B1 | 9/2002 | Weigl et al. | 2002/0047697 | A1 | 4/2002 | Husher et al. |
| 6,456,055 | B2 | 9/2002 | Shinabe et al. | 2002/0058332 | A1 | 5/2002 | Quake et al. |
| 6,463,314 | B1 | 10/2002 | Haruna | 2002/0064809 | A1 | 5/2002 | Mutz et al. |
| 6,465,169 | B2 | 10/2002 | Walderich et al. | 2002/0096123 | A1 | 7/2002 | Whither et al. |
| 6,473,176 | B2 | 10/2002 | Basiji et al. | 2002/0113965 | A1 | 8/2002 | Roche et al. |
| 6,482,652 | B2 | 11/2002 | Furlong et al. | 2002/0115055 | A1 | 8/2002 | Matta |
| 6,489,092 | B1 | 12/2002 | Benjamin et al. | 2002/0119558 | A1 | 8/2002 | Seidel et al. |
| 6,495,333 | B1 | 12/2002 | Willmann et al. | 2002/0131957 | A1 | 9/2002 | Gavin |
| 6,495,366 | B1 | 12/2002 | Briggs | 2002/0171827 | A1 | 11/2002 | Van den Engh |
| 6,503,698 | B1 | 1/2003 | Dobrinsky et al. | 2002/0182590 | A1 | 12/2002 | Strange et al. |
| 6,511,853 | B1 | 1/2003 | Kopf-Sill et al. | 2002/0186375 | A1 | 12/2002 | Asbury et al. |
| 6,514,722 | B2 | 2/2003 | Paisson et al. | 2002/0186874 | A1 | 12/2002 | Price et al. |
| 6,524,860 | B1 | 2/2003 | Seidel et al. | 2002/0198928 | A1 | 12/2002 | Bukshpan et al. |
| 6,528,802 | B1 | 3/2003 | Koenig et al. | 2003/0002027 | A1 | 1/2003 | Fritz |
| 6,534,308 | B1 | 3/2003 | Palsson et al. | 2003/0048433 | A1 | 3/2003 | Desjonqueres |

| | | | | | | |
|---|---|---|---|---|---|---|
| 2003/0059764 | A1 | 3/2003 | Ravkin et al. | EP | 0 316 173 A1 | 5/1989 |
| 2003/0059945 | A1 | 3/2003 | Dzekunov et al. | EP | 0 317 809 A2 | 5/1989 |
| 2003/0078703 | A1 | 4/2003 | Potts | EP | A-O 366794 | 5/1990 |
| 2003/0096405 | A1 | 5/2003 | Takayama et al. | EP | 0 409 293 A2 | 1/1991 |
| 2003/0098421 | A1 | 5/2003 | Ho | EP | 0 461 618 | 12/1991 |
| 2003/0113765 | A1 | 6/2003 | Dempcy et al. | EP | 0 463 562 A1 | 1/1992 |
| 2003/0119050 | A1 | 6/2003 | Shai | EP | 0 471 758 B1 | 1/1992 |
| 2003/0119206 | A1 | 6/2003 | Shai | EP | 0468100 A1 | 1/1992 |
| 2003/0129091 | A1 | 7/2003 | Seidel et al. | EP | 0474 187 A2 | 3/1992 |
| 2003/0157475 | A1 | 8/2003 | Schenk | EP | 0 316 172 B1 | 7/1992 |
| 2003/0165812 | A1 | 9/2003 | Takayama et al. | EP | 0 316171 B1 | 9/1992 |
| 2003/0175917 | A1 | 9/2003 | Cumming | EP | 0570102 A1 | 3/1993 |
| 2003/0175980 | A1 | 9/2003 | Hayenga et al. | EP | 0538786 A | 4/1993 |
| 2003/0190681 | A1 | 10/2003 | Shai | EP | 0 279 000 B1 | 7/1993 |
| 2003/0207461 | A1 | 11/2003 | Bell et al. | EP | 0 553 951 A1 | 8/1993 |
| 2003/0209059 | A1 | 11/2003 | Kawano | EP | 0 288 029 B1 | 1/1994 |
| 2004/0005582 | A1 | 1/2004 | Shipwast | EP | 0 381 694 B1 | 6/1994 |
| 2004/0031071 | A1 | 2/2004 | Morris et al. | EP | 0 361 504 B1 | 7/1994 |
| 2004/0034879 | A1 | 2/2004 | Rothstein et al. | EP | 0 289 200 B2 | 8/1994 |
| 2004/0049801 | A1 | 3/2004 | Seidel | EP | 0 555 212 B1 | 10/1994 |
| 2004/0053243 | A1 | 3/2004 | Evans | EP | 0 361 503 B1 | 11/1994 |
| 2004/0055030 | A1 | 3/2004 | Maxwell et al. | EP | 0 696 731 A2 | 2/1996 |
| 2004/0061070 | A1 | 4/2004 | Hansen | EP | 0 711 991 A1 | 5/1996 |
| 2004/0061853 | A1 | 4/2004 | Blasenheim | EP | 0 736 765 A1 | 10/1996 |
| 2004/0062685 | A1 | 4/2004 | Norton et al. | EP | 0 545 284 B1 | 2/1997 |
| 2004/0072278 | A1 | 4/2004 | Chou et al. | EP | 0 360 487 B1 | 7/1997 |
| 2004/0107150 | A1 | 6/2004 | Neas et al. | EP | 0 412 431 B1 | 10/1997 |
| 2004/0132001 | A1 | 7/2004 | Seidel et al. | EP | 0 526 131 B1 | 1/1998 |
| 2005/0003472 | A1 | 1/2005 | Anzar et al. | EP | A-O 478155 | 1/1998 |
| 2005/0011582 | A1 | 1/2005 | Haug | EP | 0 822 404 A3 | 2/1998 |
| 2005/0053910 | A1 | 3/2005 | McKenzie et al. | EP | 0 822 401 A2 | 4/1998 |
| 2005/0064383 | A1 | 3/2005 | Bashkin et al. | EP | 0781985 A3 | 7/1998 |
| 2005/0112541 | A1 | 5/2005 | Durack | EP | 0 556 748 B1 | 10/1998 |
| 2005/0214733 | A1 | 9/2005 | Graham et al. | EP | 0 430 402 B1 | 1/1999 |
| 2005/0244805 | A1 | 11/2005 | Ludwig et al. | EP | 0 529 666 B1 | 4/2000 |
| 2005/0282245 | A1 | 12/2005 | Ludwig et al. | EP | 0 994 342 A3 | 4/2000 |
| 2006/0118167 | A1 | 6/2006 | Neas et al. | EP | 0 752 133 B1 | 6/2000 |
| 2006/0121440 | A1 | 6/2006 | Schenk et al. | EP | 1 018 644 A2 | 7/2000 |
| 2006/0147894 | A1 | 7/2006 | Sowter | EP | 1 118 268 A1 | 7/2001 |
| 2006/0203226 | A1 | 9/2006 | Roche et al. | EP | 1 147 774 A1 | 10/2001 |
| 2006/0263829 | A1 | 11/2006 | Evans et al. | EP | 0 534 033 B1 | 11/2001 |
| 2006/0281176 | A1 | 12/2006 | Seidel et al. | EP | 0 925 494 B1 | 12/2001 |
| 2007/0026378 | A1 | 2/2007 | Schenk | EP | 0 748 316 B1 | 5/2002 |
| 2007/0026379 | A1 | 2/2007 | Seidel et al. | EP | 0 662 124 B1 | 6/2002 |
| 2007/0042342 | A1 | 2/2007 | Seidel et al. | EP | 1 245 944 A3 | 10/2002 |
| 2007/0092860 | A1 | 4/2007 | Schenk | EP | 1 249 502 A2 | 10/2002 |
| 2007/0099171 | A1 | 5/2007 | Schenk | EP | 1250897 A1 | 10/2002 |
| 2007/0099260 | A1 | 5/2007 | Seidel et al. | EP | 1 380 304 A2 | 1/2004 |
| 2007/0117086 | A1 | 5/2007 | Evans et al. | EP | 1 403 633 A3 | 4/2004 |
| 2007/0123461 | A1 | 5/2007 | Josephson | EP | 1 100 400 B1 | 5/2004 |
| 2007/0248976 | A1 | 10/2007 | Harding | EP | 1 257 168 B1 | 2/2005 |
| 2010/0191042 | A1 | 7/2010 | Li et al. | FR | 2574656 A1 | 6/1986 |
| | | | | FR | 635453 A2 | 2/1990 |
| | | FOREIGN PATENT DOCUMENTS | | FR | 2 647 668 A | 12/1990 |
| | | | | FR | 2699678 A1 | 6/1994 |
| CA | 1 250 808 | 3/1989 | | GB | 1471019 | 4/1977 |
| CA | 2113957 A1 | 1/1994 | | GB | 2 121 976 A | 1/1984 |
| CN | 1732983 | 2/2006 | | GB | 2 122 369 A | 1/1984 |
| CN | 1927226 | 3/2007 | | GB | 2 125 181 A | 2/1984 |
| CN | 100998524 | 7/2007 | | GB | 2 136 561 A | 9/1984 |
| CN | 101220345 | 7/2008 | | GB | 2 137 352 A | 10/1984 |
| DE | 69028526 | 2/1997 | | GB | 2145112 | 2/1985 |
| DE | 195 49 015 C1 | 4/1997 | | GB | 2 144 542 A | 3/1985 |
| DE | 198 82 943.3 | 2/2001 | | GB | 2 153 521 A | 8/1985 |
| EP | 0025296 A2 | 3/1981 | | GB | 2 243 681 A | 11/1991 |
| EP | 0 046 345 A2 | 2/1982 | | GB | 2 360 360 A | 9/2001 |
| EP | 0 068 404 B1 | 1/1983 | | JP | 61139747 | 6/1986 |
| EP | 0071538 A1 | 2/1983 | | JP | 61159135 A | 7/1986 |
| EP | 0 026 770 B1 | 3/1983 | | JP | 2024535 | 1/1990 |
| EP | 0 029 662 B1 | 2/1984 | | JP | 4126064 A | 4/1992 |
| EP | 0 025 296 B1 | 5/1985 | | JP | 4126065 A | 4/1992 |
| EP | 0140616 | 5/1985 | | JP | 4126066 A | 4/1992 |
| EP | 0 158 147 A2 | 10/1985 | | JP | 4126079 A | 4/1992 |
| EP | 0 160 201 A2 | 11/1985 | | JP | 4126080 A | 4/1992 |
| EP | 0189702 A1 | 8/1986 | | JP | 4126081 A | 4/1992 |
| EP | 0 229 814 B1 | 7/1987 | | JP | 2008-63235 | 3/2008 |
| EP | 0 246 604 A2 | 7/1987 | | SU | 1056008 | 11/1983 |
| EP | 0288029 B1 | 4/1988 | | SU | 1260778 A1 | 9/1986 |
| EP | 0276166 A2 | 7/1988 | | WO | WO 84/01265 A1 | 4/1984 |
| EP | 0 289 677 A2 | 11/1988 | | | | |

| | | |
|---|---|---|
| WO | WO 85/04014 A1 | 9/1985 |
| WO | WO 88/07198 | 9/1988 |
| WO | WO 89/04470 A1 | 5/1989 |
| WO | WO 89/04471 A1 | 5/1989 |
| WO | WO 90/13315 A1 | 11/1990 |
| WO | WO 9105236 | 4/1991 |
| WO | WO 92/08120 A1 | 5/1992 |
| WO | WO 92/17288 A1 | 10/1992 |
| WO | WO 93/10803 | 6/1993 |
| WO | WO 97/17322 A1 | 9/1993 |
| WO | 606847 P2 | 7/1994 |
| WO | WO 94/22001 A1 | 9/1994 |
| WO | WO 96/04542 A1 | 2/1996 |
| WO | WO 96/12171 A2 | 4/1996 |
| WO | WO 96/12172 | 4/1996 |
| WO | WO 9612173 A1 | 4/1996 |
| WO | WO 96/33806 A1 | 10/1996 |
| WO | WO9631764 | 10/1996 |
| WO | WO 96/29354 A1 | 8/1997 |
| WO | WO 97/30338 A1 | 8/1997 |
| WO | WO 97/35189 A1 | 9/1997 |
| WO | WO 97/43620 A1 | 11/1997 |
| WO | WO 89/04472 A1 | 5/1998 |
| WO | WO 98/34094 A1 | 8/1998 |
| WO | 98/48259 | 10/1998 |
| WO | WO 98/57152 A1 | 12/1998 |
| WO | WO 99/05504 A2 | 2/1999 |
| WO | WO 99/33956 A1 | 7/1999 |
| WO | WO 99/38883 A1 | 8/1999 |
| WO | WO 99/42810 A1 | 8/1999 |
| WO | WO 99/44035 | 9/1999 |
| WO | WO 99/44037 A1 | 9/1999 |
| WO | WO 99/47906 A1 | 9/1999 |
| WO | WO 99/60397 A1 | 11/1999 |
| WO | WO 99/61888 A2 | 12/1999 |
| WO | WO 00/06193 A1 | 2/2000 |
| WO | WO 00/12204 | 3/2000 |
| WO | WO 00/36396 | 6/2000 |
| WO | WO 00/49387 | 8/2000 |
| WO | WO 00/54026 | 9/2000 |
| WO | WO 00/56444 | 9/2000 |
| WO | WO 00/70080 | 11/2000 |
| WO | WO 01/02836 A1 | 1/2001 |
| WO | WO 01/28700 A1 | 4/2001 |
| WO | WO 0129538 | 4/2001 |
| WO | WO 01/37655 A1 | 5/2001 |
| WO | WO 01/40765 A2 | 6/2001 |
| WO | WO 01/40765 A3 | 6/2001 |
| WO | WO 01/42757 A2 | 6/2001 |
| WO | WO 01/51612 A1 | 7/2001 |
| WO | WO 01/61313 A2 | 8/2001 |
| WO | WO 01/68110 | 9/2001 |
| WO | WO 01/68226 A2 | 9/2001 |
| WO | WO 01/71348 A1 | 9/2001 |
| WO | WO 01/75161 A2 | 10/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/01189 A1 | 1/2002 |
| WO | WO 02/04666 A2 | 1/2002 |
| WO | WO 02/19594 | 3/2002 |
| WO | WO 02/19943 A1 | 3/2002 |
| WO | WO 02/20850 A2 | 3/2002 |
| WO | WO 02/21102 A2 | 3/2002 |
| WO | WO 02/23163 A1 | 3/2002 |
| WO | WO 02/25269 A2 | 3/2002 |
| WO | WO 02/26114 A2 | 4/2002 |
| WO | WO 02/28311 A1 | 4/2002 |
| WO | WO0229106 A2 | 4/2002 |
| WO | WO 02/41906 A2 | 5/2002 |
| WO | WO 0241906 A2 | 5/2002 |
| WO | 02/43574 A2 | 6/2002 |
| WO | WO 02/43486 A1 | 6/2002 |
| WO | WO 02/43574 A3 | 6/2002 |
| WO | WO 02/44319 A2 | 6/2002 |
| WO | WO 02/052244 A2 | 7/2002 |
| WO | WO 02/054044 A2 | 7/2002 |
| WO | WO 02/057775 A1 | 7/2002 |
| WO | WO 02/060880 A1 | 8/2002 |
| WO | WO 03020877 A2 | 8/2002 |
| WO | WO 02/077637 A1 | 10/2002 |
| WO | WO 02/092161 A1 | 11/2002 |
| WO | WO 02/092247 A1 | 11/2002 |
| WO | WO 03/008102 A1 | 1/2003 |
| WO | WO 03/008937 A2 | 1/2003 |
| WO | WO 03/012403 A1 | 2/2003 |
| WO | WO 03/016875 A2 | 2/2003 |
| WO | WO 03/056330 A2 | 7/2003 |
| WO | WO 03/056335 A2 | 7/2003 |
| WO | WO 03/072765 A1 | 9/2003 |
| WO | WO 03/078065 A1 | 9/2003 |
| WO | WO 03/078972 A1 | 9/2003 |
| WO | 2004/009237 A2 | 1/2004 |
| WO | WO 2004/006916 A1 | 1/2004 |
| WO | WO 2004/009237 A2 | 1/2004 |
| WO | WO 2004/009237 A3 | 1/2004 |
| WO | 2004/012837 A2 | 2/2004 |
| WO | WO 2004/012837 A3 | 2/2004 |
| WO | WO 2004/017041 A2 | 2/2004 |
| WO | WO 2004/017041 A3 | 2/2004 |
| WO | WO 2004012837 A2 | 2/2004 |
| WO | WO 2004/024227 A2 | 3/2004 |
| WO | WO 2004/024227 A3 | 3/2004 |
| WO | WO 2004/046712 A2 | 6/2004 |
| WO | WO 2004/059289 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | 2004/104178 A3 | 12/2004 |
| WO | WO 2004/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO2005095960 A1 | 10/2005 |
| WO | WO 2006/012597 A2 | 2/2006 |
| WO | WO 2006/015056 A2 | 2/2006 |
| WO | WO 2006060770 A2 | 8/2006 |
| WO | WO 2007016090 A2 | 2/2007 |
| ZA | 03109426.0 | 12/2005 |

OTHER PUBLICATIONS

PCT International Patent Application PCT/US2003/024460, filed Aug. 1, 2003.
U.S. Appl. No. 60/400,971, filed Aug. 1, 2002.
PCT International Patent Application PCT/US2011/001052, filed Jun. 8, 2011.
U.S. Appl. No. 61/353,140, filed Jun. 9, 2010.
Elliott. Heterospermic Trials at A.B.S. Proceedings of the 5th Technical Conference on Artificial Insemination and Reproduction, 1974.
Flint, et al. Fertility Assessment through Heterospermic Insemination of Flow-Sorted Sperm in Cattle, J Anim Sci 2003, 81, 1814-1822.
Johnson et al. Sex Preselection: High-Speed Flow Cytometric Sorting of X and Y Sperm for Maximum Efficiency. Theriogenology, vol. 52, 1999, pp. 1323-1341.
Abdel-Ghaffar, A. E., et al., "Rabbit Semen Metabolism" in Rabbit Production in Hot Climates' Baselga and Marai (eds); International Conference of Rabbit Production in Hot Cliamtes 1994, p. 305-312.
Akhtar, S., et al., "Prevelance of Five Stereotypes of Bluetongue Virus in a Rambouillet Sheep Flock in Pakistan", Veterinary Record 136, p. 495. (1995).
Aldrich, S. L., et al., "Parturition and Periparturient Reproductive and Metabolic Hormone Concentration in Prenatally Androgenized Beef Heifers", J. Anim. Sci. 73:3712. (1995).
Amann, R. P. et al., "Issues Affecting Commercialization of Sexed Sperm", Therio. 52:1447, (1999).
Amann, R. P., et al. "Prospects For Sexing Mammalian Sperm," Animal Reproduction Laboratory College of Veterinary Medicine and Biomedical Sciences, Colorado State University, (1982).
Amann, R.P. "Fertilizing Potential Vitro of Semen from Young Beef Bulls Containing a High or Low Percentage of Sperm with a Proximal Droplet" Theriogenology 54: 1499-1515, 2000.
Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).
Amoah, E. A. and Gelaye S., "Biotechnology Advances in Goat Reproduction", J. Anim. Sci. 75(2): 578-585. (1996).
Anderson. V. K., et al., Intrauterine and tiefzervikale Insemination mit Gefriersperma bein Schat (Intrauterine and Deep Cervical Insemination With Frozen Semen in Sheep), Zuchthygiene 8:113-118. (1973).
Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).
Asbury, Charles A. "Fluorescence Spectra of DNA Dyes Measured in a flow Cytomete," University of Washington Feb. 19, 1996.
Bagley, C. P. "Nutritional Management of Replacement Beef Heifers: a Review" J. Anim. Science 71:3155-3163. (1993).
Bailey, C. M. et al., "Nulliparous Versus Primiparous Crossbred Females for Beef", J. Anim. Sci. 69:1403. (1991).
Baker, R.D., et al., "Effect of Volume of Semen, Number of Sperm and Drigs on Transport of Sperm in Artificially Inseminated Gilts", J. Anim. Sci. 27:88-93. (1968).
Bakker Schut, Tom C. "A New Principle of Cell Sorting by Using Selective Electroportation in a Modified Flow Cytometry," University of Twente, Mar. 10, 1990.
Barnes, F. L. and Eyestone, W. H., "Early Cleavage and the Maternal Zygotic Transition in Bovine Embryos", Therio. vol. 33, No. 1, pp. 141-149. (1990).
Batellier, F. et al., "Advances in Cooled Semen Technology" Animal Reproduction Science 68 p. 181-190 (2001).
Becker, S.E. and Johnson, A. L. "Effects of Gonadotropin-Releasing Hormone Infused in a Pulsatile or Continuous Fashion on Serum Gonadotropin Concentrations and Ovulation in the Mare" J. Anim. Sci. 70:1208-1215. (1992).
Bedford, S. J. and Hinrichs, K., "The Effect of Insemination Volume on Pregnancy Rates of Pony Mares", Therio, 42:571-578. (1994).
Behrman, S. J., et al., "Freeze Preservation of Human Sperm" American Journal of Obstetrics and Gynecology vol. 103 (5) p. 654-664 Mar. 1, 1969.
Bellows, R. A. et al., "Cause and Effect Relationships Associated With Calving Difficulty and Calf Birth Weight", J. Anim. Sci. 33:407. (1971).
Berardinelli, J. G.., et al, "Source of Progesterolle Prior to Puberty in Beef Heifers". J. Anim. Sci. 49:1276 (1979).
Berger, G. S. "Intratubal Insemination", Fertil. Steril. 48:328-330, (1987).
Bergfeld, E. G., et al., "Ovarian Follicular Development in Prepubertal Heifers is Influenced by Level of Dietary Energy Intake", Bio. of Repro. 51:1051, (1994).
Berry, B. W., et al., "Beef Carcass Maturity Indicators and Palatability Attributes", J. Anim. Sci. 38:507 (1974).
Beyhan, Z., et al., "Sexual Dimorphism in IVF Bovine Embryos Produced by Sperm Sorted by High Speed Flow Cytometry", abstr. Therio. 49(1):359 (1998).
Beyhan, Z., et al.,1999 Sexual Dimorphism In IVM-IVF Bovine Embryos Produced from X and Y Chromosome-Bearing Spermatozoa Sorted By High Speed Flow Cytometry, Theriogenology, 52: 35-48.
Bigos, Martin "Nine Color Eleven Parameter Immunophenotyping Using Three Laser Flow Cytometry," Stanford Universty Dec. 22, 1998.
Bioxcell, Bovine Sperm Preservation, Advertisement Jun. 28, 2005.
Bond, J., et al., "Growth and Carcass Traits of Open Beef Heifers Versus Beef Heifers That Have Calved", Nutrition Reports International 34:621, 1986.
Boucque, C. V., et al., "Beef-Production With Maiden and Once-Calved Heifers", Livestock Prod. Sci. 7:121. 1980.
Bourdon, R. M. and J. S. Brinks. "Simulated Efficiency of Range Beef—Production III. Culling Strategies and Nontraditional Management-Systems", J. Anim. Sci. 65:963. 1987.
Bracher, V. and Allen, W.R.., "Videoendoscopic Examination of the Mare's Uterus: I. Findings in Normal Fertile Mares", Equine Veterinary Journal, vol. 24, p. 274-278, 1992.

Braselton. W. E. and McShan, W. H., "Purification and Properties of Follicle Stimulating and Luteinizing Hormones From Horse Pituitary Glands" Arch. Biochem. Biophys. 139:45-48. 1970.
Braun, J. et al, "Effect of Diffent Protein Supplements on Motility and Plasma Membrane Integrity of Frozen-Thawed Stallion Spermatozoa", Cryobiology (1995) 32:487-492.
Brethour, J. R. and Jaeger, J. R., "The Single Calf Heifer System", Kansas Agric. Sta. Rep. of Progress 570. 1989.
Brinsko, S.P. et al., "Artificial Insemination and Preservation of Semen," Veterinary Clinics of North America:Equine Practice vol. 8 No. 1 Apr. 1992 pp. 205-218.
Bristol, F. "Breeding Behavior of a Stallion at Pasture With 20 Mares in Synchronized Oestrus" J. Reprod. Fertil. Suppl. 32:71. 1982.
Brookes, A. J. and O'Byme, M., "Use of Cow-Heifers in Beef Production" J. of the Royal Agriculture Society of Enngland 126:30. 1965.
Buchanan, B. R., et al, "Insemination of Mares with Low Numbers of Either Unsexed or Sexed Spermatozoa", Therio. vol. 53, p. 1333-1344. 2000.
Buchanan, B.R. "Pregnancy Rates in Mares Following a Single Insemination with a Low Number of Spermatozoa into the Tip of the Uterine Horn" Theriogenology p. 395 1999.
Bums, P. D. and Spitzer, IC., "Influence of Biiostimulation on Reproduction in Postpartum Beef-Cows", J. Anim. Sci. 70:358. 1992.
Burgwash, L. D., et al., "Relationship of Duration of Estrus to Pregnancy Rate in Normally Cycling, Non Lactating Mares" J.A.V.M.A. 165:714-716. 1974.
Barley, D. J., et al., "Pregnancy Rates of Beef Heifers Bred Either on Puberal or Third Estrus". J. Anim. Sci. 65:645. 1987.
Caslick, E. A., "The Vulva and the Vulvo-Vaginal Orifice and its Relation to Genital Health of the Thoroughbred Mare", Cornell Veterinarian, vol. 27, p. 178-187. 1937.
Catt, et al., "Assessment of Ram and Boar Spermatozoa During Cell-Sorting by Flow Cytometry", Reproduction Dom Animal, vol. 32, pp. 251-258. 1997.
Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495, 1996.
Cave-Penney, Tony, "Sexed Semen Offers Faster Gentic Gain", Farming News, Livestock Supplement, Feb. 1997, p. 28.
Celestron: Telescope Basics: www.celestron.com/tb-2ref/htm; 4 pages, Oct. 20, 2003.
Chandler, J. E., "Videomicroscopic Comparison of Bull Sperm and Leukocyte Chromosome Areas as Related to Gender", J Dairy Sci 73, p. 2129-2135. 1990.
Chandler, J. E., et al., "Bovine Spermatozoal Head Size Variation and Evaluation of a Separation Technique Based on this Size", Therio. 52, p. 1021-1034. 1999.
Chen, S.H. "Effects of Oocyte Activation and Treatment of Spermatozoa on Embryonic Development Following Intracytoplasmic Sperm Injection in Cattle" Theriogenology 48: 1265-1273, 1997.
Chen, Y. et al., Survival of Bull Spermatozoa Seeded and Frozen at Different Rates in Egg Yolk- Tris and Whole Milk Extenders, 1993 J Dairy Sci 76:1028-1034.
Chin, W. W. and Boime, I. 1990. In Glycoprotein Hormones, Serona Symp. Norwell, MA. pp. 19-20.
Choi, Y.H. "Developmental Cappacity of Equine Oocytes Matured and Cultured in Equine Trophoblast-Conditioned Media" Theriogeneogy 56: 320-339, 2001.
Chung, Y. G., et al. "Artificial insemination of Superovulated Heifers With 600,000 Sexed Sperm". J. Anim. Sci. Suppl. 1. 836:215. 1998 abstr.
Clement, F., et al., "Which Insemination Fertilizes When Several Successive Inseminations are Performed Before Ovulation" 7th Int. Symp. Eq. Repro. 151, 1998 abstr.
Cran, D. G., et al, "Production of Lambs by Low Dose Intrauterine Insemination With Flow Cytometrically Sorted and Unsorted Semen", Therio. p. 267. 1997.
Cran, D. G., et al., "Sex Preselected in Cattle: A Field Trial", Veterinary Record 136, 1995, p. 495-496.

Cran, D. G. et al., "Production of Bovine Calves Following Separation of X- and Y-Chromosome Bearing Sperm and In Vitro Fertilization". Vet. Rec. 132:40-41. 1993.
Cran, D. G., et al., "The Predetermination of Embryonic Sex Using Flow Cytometrically Separated X and Y Spermatozoa" Human Reproduction Update 1996, vol. 2 (4) p. 355-63.
Crowley, J. P. "The facts of Once-Bred Heifer Production" School of Agric., Univ. of Aberdeen, Scotland. 1973.
Cui, K. et al, "X Larger than Y", Nature 366, p. 177-118, 1993.
Cui, K., "Size Differences Between Human X and Y Spermatozoa and Prefertilization Diagnosis", Molecular Human Reproduction, vol. 3, No. 1, pp. 61-67. 1997.
Curran, S. "Fetal Gender Determination" in Equine Diagnostic Ultrasonography 1st ed. Rantanen, N.W. and McKinnon A.O. (eds.) Williams and Williams, 1998, p. 165-169.
da Silva, Coutinho M.A.. "Effect of time of oocyte collection and site of insemination on oocyte transfer in mares." Animal Reproduction and Biotechnology Laboratiory, Colorado State Uniuversity, Fort Collins Journal of Animal Science 2002, 80:1275-1279.
DakoCvtomation, "MoFIo® Sorters" http://www.dakocytomation.us, one page, originally downloaded Jun. 26, 2003.
Database up 1 BR9704313 (Alves, De Resende at al) Jun. 4, 1999.
Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.
de Leeuw, F.E. et al: "Effects of carious cryprotective agents and membrane-stabilizing compounds on bull sperm emebrane integrity after cooling and freezing" Cryobiology US, Academic Press Inc 1993 pp. 32-44.
Dean, P.N., et al. "Hydrodynamic Orientation of Spermatozoa Heads for Flow Cytometry", Biophys. J. 23:7-13. 1978.
Demick D.S., et al. "Effect of Cooling, Storage, Glycerization and Spermatozoal Numbers on Equine Fertility" J. Anim. Sci. 43:633-637. 1976.
DenDaas, J. H. G., et al. "The relationship between the number of spermatozoa inseminated and the reproductive efficiency of dairy bulls" J Dairy Sci. 81: 1714-1723. 1998.
Denham, A. "In-vitro studies on Sandhill Range Forage as Related to Cattle Preference", M.S. Thesis. Colorado State University, 1965.
Denk, Winfried. "Two-Photon Molecular Excitation in Laser-Scanning Microscopy," Handbook of Biological Confocal Microscopy, 1995.
Deutscher, G. H. "Extending Interval From Seventeen to Nineteen Days in the Melengestrol Acetate-Prostaglandin Estrous Synchronization Program for Heifers", The Professional Animal Scientist 16:164. 2000.
Diagnostic Products Corporation, "Coat-A-Count" http://www.Proaesterone.com. 1998.
Dikeman, M. E. "Cattle Production Systems to Meet Future Consumer Demands" J. Anim Sci. 59:1631, 1984.
Dinnyes, A., et al., "Timing of the First Cleavage Post-Insemination Affects Cryosurvival of In Vitro-produced Bovine Blastocysts", Molec. Reprod. Develop. 53, p. 318-324, 1999.
Dippert, K.D, "Fertilization Rates in Superovulated and Spontaneously Ovulating Mares" Theriogenology 41: 1411-1423, 1994.
Donaldson, L. E., "Effect of Insemination Regimen on Embryo Production in Superovolated Cows", The Veterinary Record, Jul. 13, p. 35-37, 1985.
Donoghue, A.M., et al. "Timing of Ovulation after Gonadotropin Induction and its Importance to Successful Intrauterine Insemination in the Tiger (*Panthera tigris*)" J. Reprod. Fertil. 107:53-58, 1996.
Douglas, R. H., "Review of Induction of Superovulation and Embryo Transfer in the Equine" Therio. 11:33-46. 1979.
Douglas, R.H., et al. "Induction of Ovulation and Multiple Ovulation on Seasonally-Anovulatory Mares with Equine Pituitary Fractions." Therio. 2(6): 133-142. 1974.
Doyle, S. P., et al. "Artificial Insemination of Lactating Angus Cows with Sexed Semen". Proc. Western Sect. Am. Soc. Anim. Sci. 50:203. 1999.
Dresser D.W. et al. Analysis of DNA content ofLiving Spermatozoa Using Flow Cytometry Technique Journal of Reproduction and Fertility, 1993, vol. 98, pp. 357-365.

Duchamp, G., et al. "Alternative Solutions to hCG Induction of Ovulation in the Mare" J. Reprod. Fertil. Suppl. 35:221-228. 1987.
Evans, M. J. and Irvine, C. H. G. "Induction of Follicular Development, Maturation and Ovulation by Gonadotropin Releasing Hormone Administration to Acyclic Mares" Bic,. Reprod. 16:452-462. 1977.
Ferrell, C. L. Effects of Post-Weaning Rate of Gain on Onset of Puberty and Productive Performance of Heifers of Different Breeds. J. Anim. Sci. 55:1272. 1982.
Ferrell, C. L. and T. G. Jenkins. "Energy-Utilization by Mature, Nonpregnant, Nonlactating Cows of Different Types" J. Anim. Sci. 58:534. 1984.
Field, R. A., et al., "Bone-Ossification and Carcass Characteristics of Wethers Given Silastic Implants Containing Estradiol", J. Anim. Sci. 68:3663-3668. 1990.
Field, R. et al., "Growth, Carcass, and Tenderness Characteristics of Virgin, Spayed, and Single-Calf Heifers", J. Anim. Sci. 74:2178. 1996.
Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res, 54:1746-1751. 1993.
Fluharty, F. L., et al., "Effects of Age at Weaning and Diet on Growth of Calves",Ohio State University Dept. of Animal Scieneces. 1966 Ohio Agri. Res. and Den. Circular, 156:29 1966.
Foote, et al. Motility and Fertility of Bull Sperm Frozen-Thawed Differently in Egg Yolk and Milk Extenders Containing Detergent, 1987 J Dairy Sci 70:2642-2647.
Foote, R.H., "Buffers and Extenders: What Do They Do? Why Are They Important?" Proc of the NAAB Tech. Conf. on Artifcial Inseminatiom and Reproduction, 62-70 (1984).
Foulkes J. A., et al. "Artificial Insemination of Cattle Using Varying Nmbers of Spermatozoa." Vet. Rec. 101:205. 1977.
Francon, M. and Yamamoto, T., "Un Noveau et tres simple dispositif interferentiel applicable as microscope" Optica Acta 9, p. 395-408. 1962.
Fugger, E. F. "Clinical Experience with Flow Cytometric Separation of Human X- and Y-Chromosome Bearing Sperm", Therio. vol. 52, pp. 1435-1440.1999.
Fuller, Robert R. "Characterizing Submicron Vesicles With Wavelenth-Resolved Fluorescence in Flow Cytometry," University of Illinois, May 13, 1996.
Fulwyler, M. J. "Electronic Separation of Biological Cells by Volume." Science. 150:910. 1965.
Fulwyler, M. J. "Hydrodynamic Orientation of Cells." J of Histochem. and Cytochem. 25:781-783. 1977.
Garner, D. L., et al. "Quantification of the X and Y Chromosome-Bearing Spermatozoa of Domestic Animals by Flow Cytometry." Biol. Reprod. 28:312-321. 1983.
Ginther, O. J., "Sexual Behavior Following Introduction of a Stallion into a Group of Mares" Therio. vol. 19 (6) Jun. 1983.
Ginther, O. J., "Some Factors Which Alter Estrus Cycle in Mares." J. Anim. Sci. 33:1158. 1971 abstr.
Ginther, O. J., Reproductive Biology of the Mare. (2nd Ed.) Equiservices, Cross Plains, WI. 1992.
Gledhill, B. L. "Gender Preselection: Historical, Technical and Ethical Perspective." Semen Reprod. Endocrinol. 6:385-395. 1988.
Gombe, S. and Hansel, W. "Plasma LuteinizingOHormone (LH) and Progesterone Levels in Heifers on Restricted Energy Intakes." J. Anim. Sci. 37:728. 1973.
Gottlinger et al., "Operation of a Flow Cytometer", Flow Cytometry and Cell Sorting, A. Radbroch (Ed), 1992, pp. 7-23.
Gourley, D. D. and. Riese, R. L. "Laparoscopic Artificial Insemination in Sheep." Vet. Clin. N. Amer: Food Anim. Prac. 6(3): 615-633 (1990).
Graham, J. Analysis of Stallion semen and its Relation to Fertility. Abstract Reproductive Technology vol. 12 No. 1 Apr. 1996.
Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).
Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) The Early Calving of Heifers and Its impact on Beef Production. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and NormalOWeaned Calves". I. Prod. Agric. 4:168 (1991).

Grondahl, C., et al, "In Vitro Production of Equine Embryos", Biology of Reproduction, Monograph Series I, p. 299-307 (1995).

Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).

Gurnsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).

Hall, J. B., et al., "Effect of Age and Pattern of Gain on Induction of Puberty with a Progestin in Beef Heifers," J. Anim. Sci. 75:1606 (1997).

Hamamatsu. "Technical Information. Optical Detector Selection: A Delicate Balacing Act", web page. http://www.optics.ora/hamamatsu/ohotodiode.html, printed on Apr. 15, 2000. 6 panes total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harrison, L.A., et al., "Comparison of HCG, Buserelin and Luprostiol for Induction of Ovulation in Cycling Mares." Eq. Vet. Sci. 3:163-166 (1991).

Harte, F.J. "System of Production of Beef From Once Calved Heifers." In: J.C. Taylor (Ed.) The Early Calving of Heifers and its Impact on Beef Production. 123 (1975).

Hawk, H. W., et al., "Fertilization Rates in Superovulating Cows After Deposition of Semen on the Infundibulum Near the Uterotubal Junction or After Insemination with High Numbers of Sperm", XP-002101478, Therio, vol. 29, No. 5, p. 1131-4142 (1988).

Hermesmeyer, G. N., et al. "Effects of Prenatal Androgenization and Implantation on the Performance and Carcass Composition of Lactating Heifers in the Single-Calf Heifer System," The Professional Animal Scientist 15:173. 1999.

Herweijer, Hans. "High-Speed Photodamage Cell Selection Uing Bromodeoxyuridine/Hoechst 33342 Photosensitized Cell Killing." Sep. 23, 1987.

Herzenberg, Leonard A. "Flourescence-activated Cell Sorting," Sci. Am. 1976; 234, pp. 108-117.

Hilton, G. G., et al., "An Evaluation of Current and Alternatives Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fern!. 98:597-602. 1993.

Hohenboken, W. D. "Applications of sexed semen in cattle production." Therio. 52:1421. 1999.

Holtan, D. W., et al., "Estrus, Ovulation and Conception Following Synchronization With Progesterone, Postaglandin F2a and Human Chorionic Gonadotropin in Pony Mares" J. Anim. Sci. 44:431-437. 1977.

Horan, Paul K. "Quantitative Single Ana,lysis and sorting, Rapid Analysis and sorting of cells is emerging as an important new technology in research and medicine." Science, Oct. 1977.

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (Mustela putorious furo) and Pregnancies After Laparoscopic Intrauterine Insemination With Frozen-Thawed Spermatozoa." J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc. 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 1989, p. 181-190.

IMV Technologies, Protocol of Bioxcell with Fresh Semen, 1 page, 2000.

IMV Technologies, Protocol of Bioxcell with Frozen Semen, 2 pages, 2000.

Irvine, C H. G. and Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-266.

Jafar, et al., "Sex Selection in Mammals: A Review", Therio. vol. 46, p. 191-200, (1996).

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) The Early Calving of Heifers and its Impact on Beef Production. 10. (1975).

Jasko, D. J., et al., "Effect of Insemination Volume and Concentration of Spermatozoa on Embryo Recovery in Mares", Therio. 37:1233-1239, (1992).

Johnson, A. L. "Pulsatile Administration of Gonadotropin Releasing Hormone Advances Ovulation in Cycling Mares", Biol. Reprod. 35:1123-1130, (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, LA., "Flow Cytometric Determination of Spermatozoa Sex Ratio in Semen Purportedly Enriched for X or Y Bearing Spermatozoa", Therio. 1988 29:265 abstr.

Johnson, L.A., "Gender Preselection in Domestic Animals Using Flow Cytometrically Sorted Sperm" J. Anim. Sci. (Supp) I) 70:8-18, (1992).

Johnson, L.A., "The Safety of Sperm Selection by Flow Cytometry" Ham. Reprod. 9(5): 758. (1994).

Johnson, L.A., "Advances in Gender Preselection in Swine" Journal of Reproduction and Fertility Supplement, vol. 52, p. 255-266 (1997).

Johnson, L.A., "Gender Preselection in Humans? Flow Cytometric Seperation of X and Y Spermatozoa for the Prevention of X-Linked Diseases" Human Reproduction vol. 8, No. 10, p. 1733-1739 (1993).

Johnson, L.A., "Gender Preselection in Mammals: An Overview", Deutsch. Tierarztl. Wschr, vol. 103, p. 288-291 (1996).

Johnson, L.A., "Isolation of X- and Y-Bearing Spermatozoa for Sex Preselection." Oxford Reviews of Reproductive Biology. Ed. H. H. Charlton. Oxford University Press. 303-326. (1994).

Johnson, L.A., "Sex Preselection by Flow Cytometric Separation of X and Y Chromosome Bearing Spermatozoa Based on DNA Difference: a Review." Reprod. Fertil. Dev. 7:893-903. (1995).

Johnson, L.A., "Sex Preselection in Rabbits: Live Births from X and Y Sperm Separated by DNA and Cell Sorting", Biology of Reproduction 41, pp. 199-203 (1989).

Johnson, L.A., "Sex Preselection in Swine: Altered Sex Rations in Offspring Following Surgical Insemination of Flow Sorted X- and Y-Bearing Sperm", Reproduction in Domestic Animals, vol. 26, pp, 309-314 (1991).

Johnson, L.A., "Sex Preselection in Swine: Flow Cytometric Sorting of X- and Y- Chromosome Bearing Sperm to Produce Offspring", Boar Semen Preservation IV, p. 107-114. (2000).

Johnson, L.A., "Successful Gender Preselection in Farm Animals", Agricultural Biotechnology, p. 439-452. (1998).

Johnson, L.A., et al., "Enhanced Flow Cytometric Sorting of Mammalian X and Y Sperm: High Speed sorting and Orienting Nozzle for Artificial Insemination", Therio. 49(1):361 (1988) abstr.

Johnson, L.A., et al., "Flow Sorting of X and Y Chromosome-Bearing Spermatozoa into Two Populations", Gamete Res. 16:203-212. (1987).

Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).

Johnson, L.A., et al., "Flow Cytotnetry of X- and Y-Chromosome Bearing Sperm for DNA Using an Improved Preparation Method and Staining with Hoechst 33342." Gamete Research 17: 203-212. (1987).

Johnson, L.A., et al., "Modification of a Laser-Based Flow Cytometry for High-Resolution DNA Analysis of Mammalian Spermatozoa" Cytometry 7, pp. 268-273 (1986).

Joseph., R. L. "Carcass composition and meat quality in once calved heifers." In: J.C. Taylor (Ed.) The Early Calving of Heifers and its Impact on Beef Production. 143. (1975).

Joseph, R. L. and J. P. Crowley, "Meat Qualityof Once-Calved Heifers." Irish J. of Agric. Research 10:281. (1971).

Kachel, V., et al., "Uniform Lateral Orientation, Caused by Flow Forces, of Flat Particles in Flow-Through Systems", The Journal of Histochemistry and Cytochemistry, vol. 25, No. 7, pp. 774-780. (1997).

Kanayama, K., et al., Pregnancy by Means of Tubal Insemination and Subsequent Spontaneous Pregnancy in Rabbits, J. Int. Med. Res. 20:401-405. (1992).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al. "Endocrine Basis for Puberty in Heifers and Ewes." J. Repro. and Fertility, p. 393. (1995).

Kinder, J.E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse, "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in Glvcoorotein Hormones Chin. W.W. and Boime, I., eds. Serono Symposia, Norwell, MA. p. 19-20. 1990.

Koch, R. M., et al., "Characterization of Biological Types of Cattle -Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenolgy, vol. 45, 1996, pp. 1515-1521.

Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semen." J S Afr. Vet. Assoc. 56(2): 61-63. (1985).

Levinson, G., et al., "DNA-based X-Enriched Sperm Separation as an Adjunct to Preimplantation Genetic Testing for the Preparation of X-linked Disease." Mol. Human Reprod. 10:979-982. (1995).

Lightwave Electronics, "Xcyte," www.LightwaveElectronics.com.

Lindsey, A.C., et al., "Low Dose Insemination of Mares Using Non-Sorted and Sex-Sorted Sperm" Animal Reproduction Science 68 p. 279-89 (2001).

Lindsey, A.C. Hysteroscopic insemination of mares with nonfrozen low-dose unsexed or sex-sorted spermatozoa.

Liu, Z, et al. "Survival of Bull Sperm Frozen at Different rates in Media Varying in Osmolarity,"Cryobiology, vol. 27, 1998, pp. 919-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Loy, R. G. and Hughes, J.P. "The Effects of Human Chorionic Gonadotropin on Ovulation, Length of Estrus, and Fertility in the Mare," Cornell Vet. 56:41-50 (1965).

Lu. K. H. et al., "In Vitro Fertilization of Bovine Oocytes with Flow-Cytometrically Sorted and Unsorted Sperm from Different Bulls" Therio, 2001 abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug in Dairy Cattle?", Animal Research Station, Private Bag, Hamilton, New Zealand, Therio. vol. 18, No. 3, p. 245-253 (1982).

Manni, Jeff. "To-Photon Excitation Expands the Capabilities of Laser-Scanning Microscopy," 1996 Biophotonics International.

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matsuda, Y. and Tobari, I. "Chromosomal Analysis in Mouse Eggs Fertilized In Vitro With Sperm Exposed to Ultraviolet Light (UV) and Methyl and Ethy Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) The Early Calving of Heifers and its Impact on Beef Production. (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-440 (1998).

Maxwell W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6$^{th}$ ed. Edited by N. H. Booth and L. E. McDonald, Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1783 (1990).

McKinnon, A.O. and Voss, J. L. Equine Reproduction. Lea and Febiger. Philadelphia, London (1993).

McKinnon, A.O., "Predicatable Ovulation in Mares Treated With an Implant of the GnRH Analogue Deslorelin." Eq. Vet. J. 25:321-321. (1993).

McKinnon, A.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

McNutt, T. L. et al., "Flow Cytometric Sorting of Sperm: Influence on Fertilization and Embryo/Fetal Development in the Rabbit", Molecular Reproduction and Development, vol. 43, p. 261-267 (1996).

Meilgaard, M., et al., "Sensor Evaluation Techniques." CRC Press Inc., Boca Raton, FL. (1991).

Meinert C., et al., "Advanicing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Menders Jr., J.O.B. "Effect of heparin on cleavage rates and embryo production with four bovine sperm preparation protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Importing of Flow Cytometry Analysis and Sorting of Bull Spermatozoa by Optical Monitoring of Cell Orientation as Evaluated by DNA Specific Probing Molecular Reproduction and Development, 1991,vol. 30 pp. 250-257.

Meyers, P. J., et al., "Use of the GnRH Analogue, Deslorelin Acetate, In a Slow Release Implant to Accelerate Ovulation in Oestrous Mares," Vet. Rec. 140:249-252, (1997).

Michaels, C., "Beef A. I. Facilities That Work", Proc. Fifth N.A.A.B Tech. Conf. A. I. Reprod. Columbia, MO, pp. 20-22.

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 1971 54:548.

Molinia, F. C., et al., "Successful Fertilization After Superovulation and Laparoscopic Intrauterine Insemination of the Brushtail Possum *Trichosurus vulpecula*, and Tammar Wallaby, *Macropus eugenii*." J. Reprod. Fertil. 112:9-17. (1998).

Moran, C., et al., "Puberty in Heifers—a Review." Animal Reproduction Sci. 18:167. (1989).

Moran, D. M. et al., "Determination of Temperature and Cooling Rate Which induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W.M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids," Euro. J. Biochem. 54:358. (1975).

Mullis, K. B, and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation of X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al.., "Comparison of Three Weaning Ages on Cow-Calf Performance and Steer Carcass Traits," J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001 (Suppl. 1) 64:158.

Olive, M.D., "Detection of Enterotoxigenic *Escherichia coli* after Polymerase Chain Reaction Amplification with a Tehrmostable DNA Polymerase", J. of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female—A Means of Increasing Meat Production." Proc. Symp. on the Use of Once Bred Heifers and Gilts. (1973).

Ozhin F.V. et al. Artificial insemination of farm animals Moscow. Izdatelstvo Selskokhozyaastvennoi Literatury, 1961, pp. 350-361 and pp. 380-393.

Pace, M. M. and Sullivan, J. J. "Effect of Timing of Insemination, Numbers of Spermatozoa and Extender Components on Pregnancy Rates in Mares Inseminated with Frozen Stallion Semen," J. Reprod. Fertil. Suppl. 2001, 23:115-121.

Parrish, J.J., et al., "Capacitation of Bovine Sperm by Heparin", Department of Meat and Animal Science, Biology of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al "Sex Diagnosis of Equine Preimplantation Embryos Using the Polymerase Chain Reaction", Therio. vol. 44:619-627 (1995).

Penfold, L.M.et al., "Comparative Motility of X and Y Chromosome-Bearing Bovine Sperm Separated on the Basis of DNA Content", Mel. Reprod. and Develop. 1998, vol. 50, pp. 323-317.

Perry, E. J., "Historical Background" The Artificial Insemination of Farm Animals. 4th ed. E. J. Perry (ed.) New Brunswick, Rutgers University Press, pp. 3-12. (1968).

Petersen, G. A., et al. "Cow and Calf Performance Economic-Considerations of Early Weaning of Fall-Born Beef Claves", J. Anim. Sci., 64:15, pp. 15-22. (1987).

Petit, M. "Early Calving in Suckling Herds," In: J.C. Taylor (ed.) The Early Calving of Heifers and its Impact on Beef Production. p. 157-176. (1975).

Pickett B.W., et al., Recent Developments in Artificial Inseminatin in Horses, Livestock Production Science, 1998.

Pickett, B. W., et al., "Factors Influencing the Fertility of Stallion Spermatozoa in an A. I. Program." Proc. 8th International Congress Anim. Reprod. A. I. Krakow, Poland. 4:1049-1052. (1976).

Pickett, B. W., et al., "Effect of Seminal Extenders on Equine Fertility." J. Anim. Sci. 40:1136-1143. (1975).

Pickett, B. W., et al., "Influence of Seminal Additives and Packaging Systems on Fertility of Bovine Spermatozoa." J. Anim. Sci. Suppl. II, 47:12. (1978).

Pickett, B. W., et al., "Management of the Mare for Maximum Reproductive Efficiency." CSU Anim. Repro. Lab. Bull. No. 06. Fort Collins CO. (1989).

Pickett, B. W., et al., "Procedures for Preparation, Collection, Evaluation and Insemination of Stallion Semen." CSU Exp. Sta. Artira. Reprod. Lab. Gen. Series Bull. 935. (1973).

Pickett, B. W., et al., "Recent Developements in Artificial Insemination in Horses", Livestock Production Science, 40, p. 31-36 (1994).

Pickett, B. W. et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).

Pinkel et al., "Flow Chambers and Smaple Handling", Flow Ctometry: Instrumentation and Data Analysis, Van Dilla et al. (Eds.), 1985, pp. 77-128.

Pinkel, D., et al, "Flow Cytometric Determination of the Proportions of X- and Y- Chromosome-Bearing Sperm in Samples of Purportedly Separated Bull Sperm", J. of Anim. Sci. vol. 60, pp. 1303-1307 (1998).

Pinkel, D., et al., "High Resolution DNA Content Measurements of Mammalian Sperm", Cytometry 3:1-9, (1982).

Pinkel, D., et al., "Sex Preselection in Mammals? Separation of Sperm Bearing the Y and "0" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol., 178, Nov. 29, 1994.

Polge, E.J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Differential Interference Contrast (DIC) Images", Presented at the Multidimensional Microscopy: Image Acquisition and Processing V, p. 1-11 (1998).

Province, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Low Dose Insemination Technique in the Pig", Boar Semen Preservation IV, p. 115 118. (2000).

Rath, D., et al., "Production of Piglets Preselected for Sex Following in Vitro Fertilization with X and Y Chromosome-Bearing Spermatozoa Sorted by Flow Cytometry", Therio, 47, p. 795-800 (1997).

Rathi, R. et al., "Evaluation of In Vitro Capacitation of Stallion Spermatoza", Biology of Reproduction 2001, vol. 65, pp. 462-470.

Recktenwald, Diether. "Cell Separation Methods and Applications," New York 1997.

Rellina B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al.,"Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (1996).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rens, W., et al., "Improved Flow Cytometric Sorting of X- and Y-Chromosome Bearing Sperm: Substantial Increase in Yield of Sexed Semen", Molecular Reproduction and Development, p. 50-56(1999).

Rieger, D., et al, "The Relationship Between the Time of First Cleavage of Fertilized Cattle Oocytes and Their Developement to the Blastocyst Stage", Therio. 1999, p. 190.

Rigby, S. L., et al., "Pregnancy Rates in Mares Following Hysterscopic or Rectall-Guided Utero- Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases, Ithaca, New York, p. 740-749. (1971).

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid during In Vitro Maturation of Bovine Oocytes on In Vitro Fertilization and Early Embryonic Development" Biology of Reproduction 55, 1012-1016 1996.

Romita, A. "Some Considerations on the Beef Situation in Italy," In: J.C. Taylor (ed.) The Early Calvina of Heifers and its Impact on Beef Production. 23. (1975).

Roser, J. F., et al., "Reproductive Efficiency in Mares With Anti-hCG Antibodies," Prop. 9th Int. Congr. Anim. Repro. and A. I. 4:627 (1980) abstr.

Roth, T.L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 161:1 (1987).

Rowley, H. S., et al., "Effect of Insemination Volume on Embryo Recovery in Mares." J. Equine Vet. Sci. 10:298-300 (1990).

Roy, J. H., "Rearing Dairy-Herd Replacements." Journal of the Society of Dairy Technology 31:73-79 (1978).

Rutter, L. M., et al., "Effect of Abomasal Infusion of Propionate on the GnRH-Induced Luteinizing Hormone Release in Prepuberal Hefers." J. Anim. Sci. 56:1167 (1983).

Salamon, S., Artificial Inseminaion of Shee", Chippendale, New South Whales, Publicity Press. p. 83-84 (1976).

Salisbury, G. W. and VanDenmark, N. L. "Physiology of Reproduction and Artificial Insemination of Cattle." San Francisco: Freeman and Company. p. 442-551 (1978) Chapters 16 and 17. W.H.Freeman Co., San Francisco California.

Schenk, J. L. "Applying Sperm Sexing Technology to the AI Industry", Proceedings of the 18th Technical Conference on Artificial insemination & Reproduction, Sep. 29-30, 2000.

Schenk, J. L, et al., "Imminent Commercialization of Sexed Bovine Sperm", Proceedings, The Range Beef Cow Symposium XVI p. 89-96 (1999) Greeley Colorado.

Schenk, J. L., "Cryopreservation of Flow-Sorted Bovine Spermatozoa", Therio. vol. 52, 1375-1391 (1999).

Schiewe, M. C., et al., "Transferable Embryo Recovery Rates Following Different Insemination Schedules in Superovulated Beef Catle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination", 7th International Symposium on Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34, Sep. 2001.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Numbers of Nonfrozen and Sexed Spermatozoa", Atlantic Breeders Cooperative, Therio. 48: pp. 1255-1264, (1997).

Seidel, G. E. Jr et al., "Current Status of Sexing Mammalian Spermatozoa," Society for Reproduction and fertiity, pp. 733-743, 2002.

Seidel, G. E. Jr., "Commercilizing Repreductive Biotechnology—The Approach used by XY, Inc.," Theriogenology, p. 5, 1999.

Seidel, G. E. Jr. et al., "Insemination of Heifers with Sexed Sperm", Therio, vol. 52, pp. 1407-1421 (1991).

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Artificial Insemination With X-and Y-Bearing Bovine Sperm", Animal Reproduction and Biotechnology Laboratory, Colorado State Universtity, (1996).

Seidel, G. E. Jr., "Status of Sexing Semen for Beef Cattle", Texas A & M University 45th Annual Beef Cattle Short Course and Trade Show Proceedings, Aug. 9-11, p. 11124-11127, (1999).

Seidel, G. E. Jr., et al, "Insemination of Heifers With Very Low Numbers of Frozen Spermatozoa", CSU, Atlantic Breeders Cooperative, Lancaster, PA, DUO Dairy, Loveland, CO, Jul. 1996.

Seidel, G. E. Jr., et al, "Insemination of Holstein Heifers With Very Low Numbers of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., "Artificial Insemination of Heifers with Cooled, Unfrozen Sexed Semen", Therio, vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.; Oct. 1988.

Senger, P. L., et al., "Influence of Cornual Insemination on Conception in Dairy Cattle." J Anim. Sci. 66:3010-3016. (1988).

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females," J. Anim. Sci. 73:3304. (1995).

Sharpe, IC., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathan, Thesis; "Gender Preselection—Principle Scientific Options," Ch. 3.4-3.4.8, 1997.

Sharpe, Johnathan, Thesis; "Sperm Sexing using Flow Cytometry," Ch. 3.5-3.5.8; 1997.

Sharpe, Johnathan, Thesis; "Sperm Sexing—Method of Johnson et al," Ch. 3.6-4.3.4, 1997.

Shelton, J. N. and Moore, N.W. The Response of the Ewe to Pregnant Serum Mare Gonadotropin and to Horse Anterior Pituitary Extract. J. Reprod. Fertil. 14:175-177. (1967).

Shilova, A. V., et al., "The Use of Human Chorionic Gonadotropin for Ovulation Date Regulation in Mares." VIIIth Int. Congress on Anim. Repro. and A. 1.204-208. (1976).

Shorthose, W. R. and P. V. Harris, "Effect of Animal Age on the Tenderness of Selected Beef Muscles." J. Food Sci. 55:1-. (1990).

Silbermann, M., "Hormones and Cartilage. Cartilage: Development, Differentiation, and Growth," pp. 327-368. Academic Press, Inc. (1983).

Simon, M., "The Effect of Management Option on the Performance of Pregnant Feedlot Heifers," M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks," J. of Food Quality 11:1. (1988).

Smith, G. C., et al., "Relationship of USDA Maturity Gropus to Palatability of Cooked Beef," J. of Food Sci. 47:1100. (1982).

Smith, R. L., et al, Influence of Percent Egg Yolk during Cooling and Freezing on Survival of Bovine Spermatozoa, Dairy Sciences 1979 J 62:1297-1303.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Febar" http://www.splasers.com/products/oem_products/ov_fcbar.html two pages printed Nov. 14, 2002.

Spectra-Physics, The Solid State Laser Company, Vanguard 2000-HMD 532, www.specra-physics.com, Copyright 2002.

Spectra-Physics, The Solid State Laser Company, Vanguard 350-HMD 355, www.specra-physics.com Copyright 2002.

Squires, E. L, et al., "Effect of Dose of GnRH Analog on Ovulation in Mares." Therio. 41:757-769. (1994).

Squires, E. L, "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).

Squires, E. L., "Early Embryonic Loss" Equine Diagnostic Ultrasonoaraphy, first ed., Rantanen & McKinnon. Williams and Wilkins, Baltimore Maryland, p. 157-163 (1998).

Squires. E. L., et al, "Cooled and Frozen Stallion Semen", Bulletin No. 9, Colorado State University, Ft. Collins, CO. (1999).

Squires, EL., "Procedures for Handling Frozen Equine Semen for Maximum Reproductive Efficiency", (1998) pp. 1, 39-41, 81-89.

Staigmiller, R.B. "Superovulation of Cattle with Equine Pituitary Extract and Porcine FSH" Theriogenology 37: 1091-1099 1992.

Stap J. et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol 76 1998, pp. 1896-1902.

Steel, N. L., "Cost Efectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of.Estrus by Visual Observation and Radiotelemetry in Peripubertal, Estrus-Synchronized Beef Heifers," J. Anim. Sci. 74:729. (1996).

Story, C. E., et al., "Age of Calf at Weaning of Spring-Calving Beef Cows and the Effect on Cow and Calf Performance and Production Economics," J. Anim. Sci. 78:1403. (2000).

Stove) R.T. A Means for Orienting Flat Cells in flow systems Biophysical Journal, 1978,vol. 23,pp. 1-5.
Sullivan, J. J., et al., "Duration of Estrus and Ovulation Time in Nonlactating Mares Given Human Chorionic Gonadotropin During Three Successive Estrous Periods." J.A.V.M.A. 162:895-898.(1973).
Sumner, A. T. and Robinson, J. A., "A Difference in Dry Mass Between the Heads of X and Y-Bearing Human Spermatozoa",J Reprod Fertil. 48, p. 9-15 (1976).
Swanson, E. W. "Future Research on Problems of Increasing Meat Production by Early Calving." In: J.C. Taylor (ed.) The Early Calving of Heifers and its Impact on Beef Production. (1975).
Swenson, S. L., et al., "PRRS Virus Infection in Boars: Isolation From Semen and Effect on SemenQuality" from the 1995 Research Investment Report, Iowa State University, Veterinary Clinical Sciences, Iowa State University.
Taljaard. T. L., et al., "The Effect of the Laparoscopic Insemination Technique on the Oestrus Cycle of the Ewe." J. South Afr. Vet. Assoc. 62(2): 60-61. (1991).
Tatum, J. D., et al., "Carcass Characteristics, Time on Feed and Cooked Beef Palatability Attributes." J. Anim. Sci. 50:833. (1980).
Taylor, C. S., "Efficiency of Food Utilization in Traditional and Sex-Controlled Systems of Beef Production", AFRC Animal Breeding Research Organization, West Mains Road, Edinburg EH9 3JQ; Animal Prod. 1985 40:401-440.
Tervit, H.R., et al., "Successful Culture In Vitro of Sheep and Cattle Ova", Agriculture Research Council, Unit of Reprod. Physio. and Biochem.. Univ of Cambridge, p. 493-497 (1972).
Thun, Rico, et al., Comparison of Biociphos-Plus® and TRIS-Egg Yolk Extender for Cryopreservation of Bull Semen; Theriogenology Symposium, Dec. 1999, vol. 52, #8.
Time-Bandwidth Products "GE—100—XHP".www.tbsp.com. 2 pages. Jan. 2002.
Unruh, J. A. "Effects of Endogenous and Exogenous Growth-Promoting Compounds on Carcass Composition, Meat Quality and Meat Nutritional-Value." J. Anim. Sci. 62:1441. (1986).
USDA "Official United States Standards for Grades of Carcass Beef." Agric, Marketing Serv., USDA, Washington, DC. (1997).
Van Dina, Martin, "Overview of Flow Cytometry: Instrumentation and Data Analysis", Flow Cytometry: Instrumentation and Data Analysis, Van Dilla et al. (Eds.), 1985, pp. 1-8.
van Munster, E. B., et al, "Difference in Sperm Head Volume as a Theoretical Basis for Sorting X & Y-Bearing Spermatozoa: Potentials and Limitations", Therio 52, pp. 1281-1293 (1999).
van Munster, E. B., et al., "Difference in Volume of X- and Y-chromosome Nearing Bovine Sperm Heads Matches Difference in DNA Content" Cytometry vol. 35 p. 125-128 (1999).
van Munster, E. B., at al, "Measurement-Based Evaluation of Optical Path Length Distributions Reconstructed From Simulated Differential Interference Contrast Images", J of Microscopy 191, Pt.2, p. 170-176 (1998).
van Munster, E. B., et al, "Reconstruction of Optical Pathlength Distributions From Images Obtained by a Wide Field Differential Interference Contrast Microscopic", J of Microscopy 188, Pt.2, p. 149-157 (1997).
Vazquez, J. J. et al., "Nonsurgical Uterotubal Insemination in the Mare", Proceedings of the 44th Annual Convention of the American Association of Equine Practitioners, vol. 44, pp. 68-69 (1998).
Vazquez, J. M., et al., "A. I. in Swine; New Strategy for Deep Insemination with Low Number ofSpermatozoa Using a Non-surgical Methodology", 14th International Congress on AnimalReproduction, vol. 2, Stockholm, Jul. 2000, p. 289.
Vazquez, J., et al., "Development of a Non-surgical Deep Intra Uterine Insemination Technique",Boar Semen Preservation IV, IVth International Conference on Boar Semen Preservation, Maryland, Aug. 8, 1999, pp. 262-263.
Vazquez, J., et al., "Hyposmotic Swelling Test as Predictor of the Membrane Integrity in BoarSpermatozoa", Boar Semen Preservation IV, IVth International Conference on Boar Semen Preservation, Maryland, pp. 263., Jun. 2004.
Vazquez, J., et al., "Successful low dose insemination by a fiber optic Endoscope technique ni the Sow", Proceedings Annual Conference of the International Embryo Transfer Society, Netherlands, Theriogenology, vol. 53 Jan. 2000.

Vidament, M., et al., "Equine Frozen Freezability and Fertility Field Results." Therio. 48:907. (1997).
Vincent, B.C., et al, "Carcass Characteristics and Meat Quality of Once-Calved Heifers." Canadian J. Anim. Sci. 71:311. (1991).
Vogel, T., et al, "Organization and Expression of Bovine TSPY", Mammalian Genome, vol 8, pp. 491-496 (1997).
Voss, J. L. and Pickett, B. W., "Reproductive Management of the Broodmare." CSU Exp. Sta. Anim. Reprod. Lab. Gen. Series. Bull. 961. (1976).
Voss, J. L., et al., "Effect of Number and Frequency of Inseminations on Fertility in Mares." J. Reprod. Fertit. Suppl. 32:53-57. (1982).
Voss, J. L., at at., Effect of Human Chorionic Gonadotropin on Duration of Estrous Cycle and Fertility of Normally Cycling, Nonlactating Mares. J.A.V.M.A. 165:704-706. (1974).
Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.
Watson, "Recent Developements and Concepts in the Cryopreservation of Spermatozoa and the Assessment of Their Post-Thawing Function," Reprod. Fertil. Dev. 7:871-891 (1995) Abstract.
Welch G., et al., Fluidic and Optical Modifications to a FACS IV for Flow Sorting of X- and Y-Chromosome Bearing Sperm Based on DNA. Cytometry 17 (Suppl. 7): 74. (1994).
Welch, G., et al., "Flow Cytometric Sperm Sorting and PCR to Confirm Separation of X and Y-Chromosome Bearing Bovine Sperm", Animal Biotechnology, 6, pp. 131-139 (1995).
Wheeler, T. L., et al., "Effect of Marbling Degree on Beef Palatability in Bos-taurus and Bos-indicus cattle." J. Anim. Sci. 72:3145. (1994).
Wickersham, E. W. and L. H. Schultz. "Influence of Age at First Breeding on Growth, Reproduction, and Production of Well-Fed Holstein Heifers." J. Dairy Sci. 46:544. (1963).
Wilhelm, K.M. et al, "Effects of Phosphatidylserine and Cholesterol Liosomes on the Viability, Motility, and Acrosomal Integrity of Stallion Spermatozoa Prior to and after Cryopreservation", Cryobiology 31:320, 1996.
Wilson, C. G., et al., "Effects of Repeated hCG Injections on Reproductive Efficiency in Mares." Eq. Vet. Sci. 4:301-308. (1990).
Wilson, D. E. et al., "Mammal Species of the World", Smithsonian Institution Press, 1993, 1206 pp.
Wilson, M.S. "Non-surgical Intrauterine Artificial Insemination in Bitches Using Frozen Semen." J. Reprod. Fertil. Suppl. 47:307-311. (1993).
Windsor, D. P., et al, "Sex Predetermination by Separation of X and Y Chromosome-bearing Sperm: A Review", Reproduction of Fertilization and Development 5, pp. 155-171, (1993).
Woods, G. L. and Ginther, O. J. "Recent Studies Related to the Collection of Multiple Embryos in Mares." Therio. 19:101-108. (1983).
Woods, J., et al., "Effects of Time of Insemination Relative to Ovulation on Pregnancy Rate and Embryonic-Loss Rate in Mares." Eq. Vet. J. 22(6): 410-415. (1990).
Zhou, Hongwei, et al. "Research on and Development of Flow Cell Sorting Apparatuses," Gazette of Biophysics, vol. 13, ed. 3, 1997.
Hamamatsu. "Photomultiplier Tubes." web page, http://www.optics.oro/hamamatsu/pmt.html. Printed on Apr. 15, 2000 4.
Hermesmeyer, G.N., et al. Effects of Lactation and Prenatal Androgenization on the Performance, Carcass Composition, and Longissimus muscle sensory characteristics of heifers in the single-calf heifer system. The Professional Animal Scientists 15: 14-23, (1995).
Seidel, G. E. Jr., "Fertility of Bulls on the edge of the Dose-Response Curve for Numbers of Sperm per Inseminate"; Proceedings of the 17th Technical conference on Artificial Insemination & Reproduction, 1998.
Hollinshead, F.K. et al. "In vitro and in vivo assesment of functional capacity of flow cytometrically sorted ram spermatozoa after freezing and thawing." Reprod. Fertil. and Develop. 2003. vol. 15, pp. 351-359.
Hollinshead F. K. et al. "Production of lambs of predetermined sex after the insemination of ewes with low numbers of frozen-thawed sorted X- or Y- Chromosome-bearing spermatozoa", Reprod. Fertil. and Develp. 2002, vol. 14, pp. 503-508.

Hollinshead F. K. et al. "Sex-Sorting and Re-cryopreservation of Frozen-Thawed Ram Sperm for In Vitro Embryo Production" Theriogenology, vol. 53, (2003) pp. 209.

Dhali et al. Vitrification of Buffalo (*Bubalus bubalis*)Oocytes, Embryo Theriogenology vol. 53, pp. 1295-1303 (2000).

Borini et al. Cryopreservation of Mature Oocytes: The use of a trypsin inhibitor enhances fertilization and obtained embryos rates, Fertil. Steril. (1997), vol. 68 (Suppl.).

Hollinshead F. K. et al. "Production of lambs of predetermined sex after the insemination of ewes with low numbers of frozen-thawed sorted X- or Y- Chromosome-bearing spermatozoa", Reprod. Fertil. and Develop. 2002, vol. 14, pp. 503-508.

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for In Vitro fertiliation and AI, Journal of Animal Science,vol. 77, Suppl 2/J, Dairy Sci. vol. 82, Suppl. 2/1999 pp. 213-220.

Peters D., The LLNL high-speed sorter: Design features,operational characteristics, and bioloical utility, Cyometry, 6:290-301 (1985).

Rens W., et al Slit-scan flow cytometry for consistent high resdolution DNA analysis of X- and Y- chromosome bearing sperm, Cytometry 25:191-199 (1996).

van Munster, E. B. Interferometry in flow to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluoreseense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/1srll.htm, pp. 14, May 11, 2004.

Saacke,R.G., Can Spermatozoa with abnormal heads gain access to the ovum in artificially inseminated super- and single-ovulating cattle? Theriogenology 50:117-128. 1998.

Hawk, H.W., Gamete Transport in the Suporovulated Cow. Theriogenology: Jan. 1998 vol. 29 No. 1 pp. 125-142.

Blecher, S.R., et al. A new approach to immunological sexing of sperm, Theriogenology, 52(8), pp. 1309-1321, 1999.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen recepters (ER) a and (3 during early development of bovine fetal ovaries; The society for the study of reproduction 38th annual meeting Jul. 24-27, 2005; Abstract Only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65(2006) 299-307.

Garner, D. L., Flow cytometric sexing of mammalian sperm, Theriogenology, 65 (2006) 943-957.

Habermann F. A., et al., Validation of sperm sexing in the cattle (*Bos taurus*) by dual colour flourescence in situ hybridization; J. Anim Breed Genet. Apr. 2005; 1:22-7 (Abstract only).

Johnson, L. A., Sexing mammalian sperm for production of offspring: the state-of-the-art; Animal Reproduction Science; 60-61 (2000) pp. 93-107.

Seidel, G.E. Jr., et al., Methods of Ovum Recovery Factors Affecting Fertilization of Superovulated Bovine Ova, Control of Reproduction in the Cow, Sneenan ed., 1978 pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., at al., In vitro production of bovine embryos using sex-sorted sperm, Theriogenology, 65 (2006) 1007-1015.

Johnson, L.A., et al, 1996 Gender preselection in mammals. XX Beltsville Symposium in Agriculture Research Technolog's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437.

Hagele, W.C., et al., Effect of Seperating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006 entitled "Apparatus, Methods and Processes for Sorting Particles and for Providing Sex-Sorted Animal Sperm".

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dariy Sci. Assoc., 2005.

Bailey, T. et al., Milk Production Evaluation In First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931 E00.htm.

Kume, Shin-ichi; Dept of Animal Nutrition National Institute of Animal Indstry Tsukuba 305, Japan The Dairy Industry $in Asia B. Japan; www.agnet.org/library/article/eb384b.html.

Crichton,E. et al., 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H. et al., Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology (1998) www.foodsci.uoguelp.ca/dairyedu/biosynthesis.html.

Milf Production, Released Jul. 18, 2006, by the National Agricultural Statistics Service (NASS), Agri. Stats. Board, US Dept of Agri.

DeVries, A. Economic Value of Pregnancy in Dairy Cattle Journal of Dairy Sci. 89:3876-3885/American Dairy Sci. Assoc. 2006.

Garner, D.L. et al., Viability Assessment of Mammalian Sperm Using SYBR-14 and Propidium Lodide, 1996, Biology of Reproduction, vol. 53, pp. 276-284.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel *Anguilla japonica*, National Research Institute of Aquiculture; 28th Panel Proceedings (1999).

Morisawa, M. The Process of the Initiation of Sperm Motility; Laboratory of Physiology, Ocean Research Institute, University of Tokyo (1986).

McGrady, A.V., et al. Cholinergic Effects on Bull and Chimpanzee Sperm Motility; Biology of Reproduction 15, 248-253 (1976).

Klinc, P. Dissertation—Improved Fertility Flowcytometrically Sex Selected Bull Spermatozoa, School of Veterinary Medicine Hanover Germany, 2005.

Jones. J.M. et al. Acidification of Intracellular pH in Bovine Spermatozoa Suppresses Motility and Extends Viable Life, Journal of Andrology, vol. 21, No. 5, September/October 616-624.

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp.

Babcock, D. F., Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and -D-Glucuron idase Activity as Indicators of Sea Bass Semen Quality; Biology of Reproduction 70,1679-1684 (2004).

Hanania, E. G, et al. A novel Automated Method of Scanning Cytometry and Laser-Induced Necrosis Applied to Tumor Cell Purging, Blood. Nov. 15, 1999, vol 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of Cholesterol-loaded cyclodextrin on the cryosurvival of bull sper,, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Bavister, B.D. et al., The effects of Sperm Extracts and Energy Sources on the Motility and Acromosome Reaction of hamster Spermatozoa in vitero; Biology of Reproduction 16, 228 237 (1997).

Fattouh, EI-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:574-882.

Panskowski, J., A., et al. Use of Prostaglandin F2a as a Postpartum Reproductive Management Tool for Lactating Dairy Cows; 1995 J. Dairy Sci Sci 78:1477-1488.

Scipioni R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76; 184-188 (2007).

Garner, D. L., Sex-Sorting Mamallian Sperm: Concept to Application in Animals; Journal of Andrology, vol. 22, No. 4 Jul./Aug. 2001.

Tubmann, L.M. et al., Jharacteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130 American Dairy Science Assoc.

Ferre, L., In vitro-derived embryo production with sexed and unsexed semen from different bulls; Reproduction Fertility and development, vol. 16, Part 1/2, p. 253, 2004.

Dalton, JC, et al.. Effect of Time of Insemination on Number of Accessory Sperm, Fetilizaion Rate, and Embryo Quality in Nonlactating Dairy Cattle. J Dairy Sci. 84:2413-2418.

Dransfield, M.B.G., et al., Timing of Inseminatio for Dairy Cows Identified in Estrus by a Radiotelemetric Etrus Detection System, 1998 J Dairy Sci. 81: 1874-1882.

Maatje, K. et al. Predicting Optimal Time of Insemination in Cows that Show Visual Signs of Estrus by Estimating onset of Estrus with Pedometers.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozehoom, K. J. et al. Late Estrus or Metestrus Insemination After Estrual Inseminations Decreases Farrowing Rare and Litter Size in Swine J. Animal Sci. 1997. 75:2323-2327.

Peeler, I. D. et al. Pregnancy Rates After Times Al of Heifers Following Removal of Intavaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attepmts on freezing the Greylag (*Anser anser* L.) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conley, H.H. et al. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Bakst, Murray R. Fate of Fluorescent Stained Sperm following Insemination: New Light on Ovicucal Sperm Transport and Storage in the Turkey.

Johnson L.A., et al. Use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Rath, D., "On the Status of Sex-Specific Sperm Sorting" Review lecture ET Conference 2002, Department of Animal Production and Animal Behaviour, Mariensee, Germany.

Grossfeld, R., "Experiments to Improve the Quality of Sex-Sorted Fresh and Frozen Porcine Spermatozoa" PhD thesis of the Faculty of Agriculture Sciences, Gerog-August University, Gottingen, May 2007.

de Graaf, S.P. et al., Birth of offspring of pre-determined sex after artificial insemination of frozen-thawed, sex-sorted and re-frozen-thawed ram spermatozoa, Theriogenology, 67 (2007) 391-398.

O'Brien, J.K. et al., Development for sperm sexing and associated assisted reproductive technology for sex preselection of captive bottlenose dolphins, Reproduction Fertility and Development, 2006, 18, 319-329.

Zhang, M, et al., In vitro fertilization with flow-sorted buffalo sperm, Reproduction Fertility and Development, 2005, 18(2), 283-284.

Schenk, J.L. et al., Insemination of cow elk with sexed frozen semen, 2003 Theriogenology 59, 514.

BD Biosciences Brochure, BD FACSCalibur Flow CytoMeter, The Automated, Multicolor Flow Cytometry System, 2006.

Johnson L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.

Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.

Presicce, G.A., et al., First established pregnancies in mediterranean italian buffalies (*Bubalus bubalis*) following deposition of sexed spermatozoa near the utero tubal junction, Reproduction in Domestic Animals, vol. 40, No. 1, Feb. 2005, pp. 73-75(3).

Dielemann, Si., Superovulation in cattle: from understanding the biological mechanisms to genomics of the oocyte; $23_{rd}$ Annual meeting A.E.T.E—Alghero; Sep. 2007.

Hasler, J.F., Factors influencing the success of embryo transfer in cattle; $23^{rd}$ World Buiatrics Congress, Quebec, Canada Jul. 2004.

Mapletoft, R. J. et al., Superovulation in perspective, Bioniche Animal Health, Dec. 2002.

Bahr, G.F.etal., Considerations of volume, mass, DNA, and arrangement of mitochondria in the midpiece of bull spermatozoa, Experimental Cell Research 60 (1970) 338-340.

Baumber, J., et al., "The Effect of Reactive Oxygen Species on Equine Sperm Motility, Viability, Acrosomal Integrity, Mitochondrial Membrane Potential, and Membrane Lipid Peroxidation", 2000, Journal of Andrology, vol. 21 (6),pp. 895-902.

BD LSR II Flow Cytometer, BD Biosciences Clontech Discovery labware Immunocytometry systems Pharmingen Jan. 28, 2004.

Bermudez, D.et al., The immediate effect of IR, laser readiation on rat, germ, cells, was studied by cytophotometric quantification, Scisearch 2001.

Sequent Biotechnologies Inc., Welcome to the Sequent Biotechnologies Inc. website., http://www.sequentbiotech.com/ Dec. 6, 2003.

Brooks, D.E., Manipulation of Mammalian Gametes in Vitro, Biennial Report, Waite Agriculture Research Institute 1986-1989.

Bruemmer, J.E. et al., "Effect of Pyruvate on the Function of Stallion Spermatozoa Stored for up to 48 Hours", Journal of Animal Science 2002, vol.80*1, pp. 12-18.

Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).

Chaudhry, P. et al., Casein Kinase II activity and polyamine-stimulated protein phosphorylation of cytosolic and plasma membrane protiens in bovine sperm, Archives of Biochemistry and Biophysics vol. 271, No. 1 pp. 98-106, May 15, 1989.

Chen, Y. et al., Effects of sucrose, trehalose, hypotaurine, taurir e, and blood serum on survival of frozen bull sperm, Cryobiology 30,423-431 (1993).

Chapter 16 Semen processing, storage, thawing, and handling, http://nongae.gsnu.ac.kr/-cspark/teaching/chap16.html Sep. 23, 2002.

Conover,J. et al., Pre-loading of mouse oocytes with DNA-specific fluorochrome (Hoechst 33342) permits rapid detection of sperm-oocyte fusion, Journals of Reproductive & Fertility Ltd. 82, (1988).

Cressman, B.E. MD, et al., Effect of sperm dose on pregnancy rate from intrauterine insemination: a retrosnective analysis, Texas Medicine, 92:74-79 (1996).

Crissman, H.A. et al., Use of DIO-C5-3 to improve hoechst 33342 uptake, resolution of DNA content, and survival of CHO cells, Experimental cell research 174: 338-396 (1988).

Graves, C.N., et al., "Metabolism of Pyruvate by Epididymal-Like Bovine Spermatozoa", 1964 Journal of Dairy Science vol. 47 (12), pp. 1407-1411.

Certified Semen Services, CSS Minimum requirements for disease control of semen produced for AI, http://www.naab-css.org/about_css/disease_control-2002.html Sep. 22, 2003.

Culling, "Handbook of Histopathological and Histochemical Techniques," 3rd Ed., Butterworths, pp. 192.

De Grooth, B. et al., Simple delay monitor for droplet sorters, Cytometry 12:469-472 (1991).

Lodge, J.R., et al., "Carbon Dioxide in Anaerobic Spermatozoan Metabolism" 1968, Journal of Dairy Science, vol. 51(1), pp. 96-103.

Delgado,N. et al., Correlation between sperm membrane destabilization by heparin and aniline blue staining as membrane integrity index, Archives of Andrology 40:147-152 (1998).

Denniston, D.J. et al., "Effect of Antioxidants on the Motility and Viability of Cooled Stallion Spermatozoa", Journal Reproduction Supplement 56, 2001, pp. 121-126.

Donoghue, A. et al., Effects of water- and lipid-soluble antioxidants on turkey sperm viability, membrane integrity, and motility during liquid storage, Poultry Science 76:1440-1445 (1997).

Durack, Gary; "Cell—Sorting Technology", Emerging Tools for Single-cell Analysis, Chapter 1 pp. 1-359.

Zucker, R. et al., Utility of light scatter in the Morphological analysis of sperm, Cytometry 13:39-47 (1992).

Ericsson, S. et al,, Interrelationships among fluorometric analyses of spermatozoa function, classical semen quality parameters and the fertility of frozen-thawed bovine spermatozoal, Theriogenology 39:1009-1024 (1993).

Ericsson, et al. "Flow Cytometric Evaluation of Cryopreserved Bovine Spermatozoa Processed Using a New Antibiotic Combination", Theriogenology, 1990, vol. 33(6), pp. 1211-1220.

Cho, et al. A microfluidic device for separating motile sperm from nomotile sprem via inter-streadmline crossings. Microtechnologies in Medicine and Biology, $2^{nd}$ Annual Int'l IEEE-EMB Special Topic Conference, Sep. 7, 2002.

Ericsson, R. et al., Functional differences between sperm bearing the X- or Y-chromosome, Colorado Ass. Univ. Press, 1982.

Esteves, S. et al., Improvement in motion characteristics acrosome status in cryopreserved human spermatozoa by swim-up processing before freezing, Human Reproduction of vol. 15 No. 10 pp. 2173-2179 (2000).

Evenson, D.et al., Physiology and Management, Rapid determination on sperm cell concentration in bovine Semen by flow cytometry, J Dairy Sci. 76: 86-94 (1993).

Farrell et al., "Quantification of Bull Sperm Characteristics measured by Computer-Assisted Sperm Analysis (CASA) and the Relationship of Fertility", Theriogenology, 1998, vol. 49 (4), pp. 871-879.

Fitzgerald, D., Cell sorting: An enriching Experience, The Scientist Jul. 23, 2001.

Foote,R., The history of artificial insemination: Selected notes all notables, American Society of Animal Science (2002).

Foote, R., Functional differences between sperm bearing the X- or Y-chromosome. Colorado Ass. Univ. Press, 1982.

Garner, D., Past, Present and future perspectives on sexing sperm, CSAS Symposium SCSA: 67-78.

Johnson, L. et al., Sex preselection in mammals by DNA: A method for flow separation of X and Y Spermatozoa in humans. USDA, 1996.

Johnson, L. et al., Recent advances in sex preselection of cattle: Flow cytometric sorting of X-&Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 (1994).

Pinkel,D.et al.,Flow cytometry of mammalian sperm progress in DNA and morphology measurement, The Journal of Histochemical and Cytochemistry vol. 27 No. 1 pp. 353-358 (1979).

Fugger, E. et al., Birth of normal daughters after MicroSort sperm separation and intrauterine insemination, in-vitro fertilization, or intracytoplasmic sperm injection, http://www.microsoft.net/HumRepro.htm Mar. 19, 2003.

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Salisbury, G.W., et al., Reversal by Metabolic Regulators of C02-induced Inhibition of Memmalian Spermatozoa, 1959, Proc Soc Exp Biology Med, vol. 101 (1) pp. 187-189.

Centola, G. et al., Cryopreservation of human semen. Comparison of cryopreservatives, sources of variability, and prediction of post-thaw survival. PMID: 1601749 May-Jun. 1992.

Bencic, D.C., et al., "Carbon Dioxide Reversibly Inhibits Sperm Motility and Fertilizing Ability in Steelhead (*Onoorhynchus mykiss*)" 2000, Fish Physiology and Biochemistry, vol. 23(4), pp. 275-281.

Boatman, D.E. et al., "Bicarbonate Carbon Dioxide Regulation of Sperm Capacitation Hyperactivated Motility and Acrosome Reactions", 1991, Biology of Reproduction vol. 44(5), pp. 806-813.

Garcia, M.A. et al., "Development of a Buffer System for Dialysis of Bovine Spermatozoa Before Freezing III.Effect of Different Inorganic and Organic Salts on Fresh and Frozen-Thawed Semen", 1989, Theriogenology, vol. 31(5),pp. 1039-1048.

Courtens, J. et al., Numerical simulation for freezing and thawing mammalian spermatozoa. Evaluation of cell injuries at different depths in bags or straws during all steps of the technique. Institute national do la recherché agronomique, 37380 Nouzilly, France.

Eiman, M.et al., Trehalose-enhanced fluidity of the goat sperm membrane and its protection freezing, Biology of Reproduction 69: 1245-1250 (2003).

Foote, R.et al., Physiology and Management, Fertility of bull spermatozoa frozen in whole milk extender with trehalose, taurine, or blood serum, J. Dairy Sci. 76:1908-1913 (1993).

Johnson, L. et al., Storage of bull semen, Animal Reproduction Science 62:143-172 (2000).

Johnson, L. et al.,Erratum to "Storage of bull semen", Animal Reproduction Science 62: 143-172 (2000).

McNutt,T.et al., Electrophoretic gel analysis of Hoechst 33342 stained and flow cytometrically sorted bovine sperm membrane proteins, Reprod. Dom Anim.31: 703-709 (1996).

Van der Werf, Julius, An overview of animal breeding programs; Animal Breeding Use of New Technologies (This is a Post Graduate Foundation Publication).

Best, T. P. et al. "Nuclear Localization of Pyrrole-Imidazole Ployamide-Flourescein Conjugates in Cell Culture", PNAS, 2003, vol. 100(21), pp. 12063-12068.

Gygi, M.P., et al. "Use of Fluorescent Sequence-Specific Polyamides to Discriminate Human Chromosomes by Microscopy and Flow Cytometry", Nuci Acids Res. 2002, vol. 30(13),pp. 2790-2799.

Young, L.et al., Prolonged feeding of low levels of zearalenone to young boars, BD Biosciences, BD AccuDrop Potion, www.bdbiosciences.com, Sep. 2002.

Agarwal, A.et al., Filtration of spermatozoa through L4 membrane:a new method, Fertility and Sterility, vol. 06, No. 6, Dec. 1991.

Anzar, M.et al., Optimizing and Quantifying fusion of liposomes to mammalian sperm using to mammalian sperm using resonance energy transfer and flow cytometric methods, Cytometry49:22-27 (2002).

Anzar, M.et al., Sperm Apoptosis in fresh and cryopreserved bull semen detected by flow cytometry and it's relationship with fertility, Biology of Reproduction 66: 354-360 (2002).

Arav, A.et al., New trends in gamete's cryopreservation, Molecular and Cellular Endocrinology 187:77-81 (2002).

Arndt-Jovin et al., "Analysis and Sorting of Living Cells According to Deoxyribonucleic Acid Content", Journal Histochem. and Cytochem., 1977, vol. 25(7), pp. 585-589.

Arts,E.et al.,Evidence for the existence of lipid-diffusion barriers in the equatorial segment of human spermatozoa, Boichem J.384:211-218 91994).

Garner,D.et al., Spermatozoa and Seminal Plasma. Reprod. in farm animals, 7th edition, Malvern, Lea & Febiger, 1987.

Gadella B,et al., Dynamics in the membrain organization of the mammalian sperm cell functionality in fertilization, Vet Quart. 21:142-146 (1999).

Garner, D.et al., Chromatin stability in sex-sorted sperm, VII International Congress of Andrology, 2001.

Garner,D. et al., Morphological and ultrastrutural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm Theriogenology, vol. 57 No. 1, 1-810 (2002).

Garner, D. et al., Assessment of spermatozoa) function using dual fluorescent staining and flow cytometric analysis, Biology of Reproduction 34:, 127-138 (1986).

Gebhard D., Sorting Viability . . . one more time, http://www.cyto.purdue.edu/hmarchiv/1998/2263.htm Feb. 14, 2004.

Givan,A., Flow Cytometry First Principles, (1992).

Gledhill, B.et al., Identifying and seperating X- and Y-Chromosome-bearing mammalian sperm by flow cytometry, Lawrence Livermore National Laboratory, Feb. 8, 1984.

Gledhill, B.et al., Identifing X- and Y- chromosome- bearing sperm by DNA content:Retrospective perspectives and prospective opinions'.

Gledhill, B.et al., Flow microflurometric analysis of sperm DNA content: Effect of cell shape on the fluorescence distribution, J. Cell Physiol.87: 367-378.

Gledhill, B.et al., Flow cytometry and sorting of sperm and male germ cells, Flow Cytometry and sorting, second edition, pp. 531-551 (1990).

Gordon et al., "Genetic Transformation of Mouse Embryos by Microinjection of Purified DNA", Proc. Natil Acad. Sci., 1980, vol. 77 (12), pp. 7380-7384.

Graham, J.et al.,Analysis of sperm cell viability, Acrosomal integrity, and Mitocondrial function using flow cytometry, Biology of Reproduction 43: 55-64 (1990).

Graham, J.et al., Effect of some Zwitter Ion buffers on freezing and storage of spermatozoa I, Bull, J. Dairy Sci 55:372-378 (1992).

Grogan, W. et al., DNA Analysis and sorting of viable mouse testis cells, The Journal of Histochemistry Cytochemistry, vol. 29 No. 6 pp. 738-746, (1981).

Guthrie, et al., "Flow Cytometric Sperm Sorting: Effects of Varying laser Power on Embryo Developement in Swine", Mol. Reprod. and Develop., 2002,vol. 61 (1), pp. 87-92.

Hacker-Klom, U.B., et al., Effect of doxorubicin and 4'-epidoxorubicin on mouse spermatogenesis. Mutation Research International Journal on Mutagenesis vol. 159, pp. 39-46. 1986.

Hargrove, T. et al., Special Techniques, Part B Cryopreservation, Chapter 11B.

Hasler, J., Symposium: Reproductive Technology and Genetic improvementJ. Dairy Sci. 75:2857-2879 (1992).

Held, A.et al., Quasi—CW Solid- state lasers Expand their reach, Photonics Spectra, Dec. 2002.

Hinkley, R.et al., Rapid visual detection of sperm-egg fusion using the DNA-Specific Fluorochrome Hoechst 33342, Developmental Biology 118: 148-154 (1986).

Januskauskas, A.et al.,Assessment of sperm quality through Fluorometry and sperm chromatin structure assay in relation to field fertility of frozen-thawed semen from Swedish Al bulls, Theriogenology 55:947-961 (2001).

Jeyendran, R.S. et al., Effect of glycerol and cryopreservaton on oocyte penetration by human spermatozoa, PMID: 4025843, Jul. 6, 2006.

Johnson, L., A flow cytometric/ sorting method for sexing mammalian sperm validated by DNA analysis and live births, Cytometry, p. 42 of supplement, Sep. 4, 1990.

Johnson, L., Flow sorting of intact X & Y chromosome-bearingmammalian spermatozoa, The Journal of the Society for Analytical Cytology Cytometry, (1988).

Zhang, M. et al., Development of bovine embryos after in vitro fertilization of oocytes with a flow cytometrically sorted, stained and unsorted sperm from different bulls, Theriogenology 60: 1657-1663 (2003).

Jones, R. et al. Effect of Osmolality and Phosphate, "iris", "Tes", "Mes", nd "Herpes" Hydrogen ion buffers on the motility of bull spermatozoa stored at 37 or 5° C., Ausi J. Biol. Sci.25:1047-1055 (1972).

Jones, R., Plasma membrane structures and remodelling during sperm maturation in the epididymis, Journal of Reproduction and Fertility (1998).

Gerrits, Roger J. Application of Biotechnology to Animal Production US Dept. of Agriculture, Beltsville Maryland.

Johnson, L, Separation of X and Y Chromosome-bearing mammalian sperm by DNA content cytometric analysis and sorting, US Department of Agriculture.

Johnson, M., The Macromolecular Organization of membranes and its bearing on events leading up to Fertilization, Journal of Reproduction and Fertility (1975).

Johnson, L., Verified Sex Pre-Selection in Farm Animals. Proceedings of the $2^{nd}$ Int. Conf. on Boar Semen Pres. Belrin and Hamburg : Paul Parey Sci. Publishers, 1990, pp. 213-219.

Johnson, L., Progress towards achieving sex preselection in farm animals, USDA Agriculture Research Service, (1989).

Keeler, K. et al., Flow microfluorometric analysis of living spermatozoa stained with Hoechst 33342, J. Reprod. Fert. 68:205-212 (1983).

Keij, J. et al., High speed Photodamage cell sorting: An evaluation of the Zapper Prototype, Methods in cell Biology vol. 42, (1994).

Kirchhoff, C. et al., The Molecular biology of the sperm surface:Post-Testicular Membrane Remodelling, The Fate of the Male Germ Cell, (1997).

Krueger, C. et al., Low dose Insemination in synchronized gilts, Theriogenology 52: 1363-1373 (1999).

Lahdetie, J., induction and survival of micronuclei in rat spermatids. Comparison of two meiotic micronucleus techniques using cyclophosphamide, Mutation Research, 203:47-53 (1988).

Laser Innovations—Applications, http://www.laserinnovations.com/448nm.htm Feb. 2, 2004.

Libbus, B. et al., Incidence of chromosome aberrations in mammalian sperm stained with Hoechst 33342 and UV-laser irradiated during flow sorting, Mutation Research, 182: 265-274 (1987).

Loken, M., Separation of viable T and B lymphocytes using a cytochemical stain, Hoechst 33342, The Journal of Histochemistry and Cytochemistry,vol. 28, No. 1, pp. 36-39 (1980).

Lucas, J. et al., Orientation measurments of microsphere doublets and metaphase chromosomes in flow, Cytometry 7:575-581 (1986).

Luttmer, S. et al., Examination of living and fixed gametes and early embryos stained with supravital fluorochromes (Hoechst 33342 and 3,3'-dihexyloxacarocyanine Iodide), Gamete Research 15:267-283 (1986).

Masaki et al. Effect of bull seminal plasma on the membrane characteristics of boarepididymal spermatozoa. Int'l Congress on Animal Reprod. and Artificial Insemination. Univ. of III, pp. 10-14, Jun. 1984.

Maxwell, W. et al.,Physiology of spermatozoa at high dilution rates:The influence of seminal plasma, Theriogenology 52:1353-1362 (1999).

Mazur, The role of Intracellular freezing in the death of cells cooled at supraoptimal rates, Cryobiology 14:251-272, 1977.

McSweeney, K. et al., Abstract: Insemination of lactating holstein cows with sexed frozen/thawed sperm, http://www.cvmbs.colostate.edu/physio/abstract/ges12.html Mar. 16, 2004.

Medeiros, C. et al., Current status of sperm cryopreservation: Why isn't it better? Theriogenology 57: 327-344 (2002).

Meistrich, M., Potential and limitations of physical methods for separation of sperm bearing an X- or Y- chromosome.

Meistrich, M. et al., "Cytogenetic" studies of spermatids of mice carrying Cattanach's translocation by flow cytometry, Chomosoma 74:141-151 (1979).

Morrell, J. et al., Offspring from inseminations with mammalian sperm stained with Hoechst 33342, either with or without flow cytometry, Mutation Research 224:177-183 (1989).

Morrell et al.,"Sexing of Sperm by Flow Cytometry", The Veterinary Record, 1988, pp. 322-324.

Morrier, A. et al., Glycerol addition and conservation of fresh and crypreserved ram spermatozoa, Canadian Journal of AnimalScience, Sep. 2002 http://pubs.nrc-cnrc.gc.ca/aic-journals/2002ab/cjas02/sep02/cjas01-045.html.

Moruzzi, J., Selecting a mammalian species for the separationof X- and Y- chromosome-bearing spermatozoa, J. Reprod. Fert. 57:319-323, (1979).

Murthi S. et al., Improved data acquisition system for digital flow cytometry, (2002).

Gwo-Bin, L et al., Multi-cell-line micro flow cytometers with buried SU-8/SOG Optical waveguides, Feb. 2002.

OcanaQuero, J. et al., Bioiogical effects of helium-neon irradiation on acrosome reaction in bull, Scisearch Journal of Photochemistry and Photobiology, vol. 40 No. 3, pp. 294-298 (1997).

Panagawkar, G. et al., Physical and biochemical characteristics of semen in relation to fertility of Holstein-Friesian bulls, Indian vet. Med.J. vol. 13 21-26 (1989).

Papa, S. et al., Chromatin organization in Isolated nuclei: Flow cytometric characterization employing forward and perpendicular light scatter, Cell Biochemistry and Function vol. 6: 31-38 (1988).

Parks, J. et al., Lipids of plasma membrane and outer acrosomal membrane from bovine spermatozoa, Blology of Reproduction 37:1249-1258 (1987).

Parks. J. Processing and handling bull semen for artificial insemination—Don't add insult to injury!, Department of Animal Science Cornell University.

Partec, Taking flow cytometry to the next generation, Catalogue 2001-2002.

Perez-Pe, R, et al., Semen plasma proteins prevent cold shock membrane damage to ram spermatozoa, Theriogenology 56 (3) : 425-434, Aug. 1, 2001, PMID: 11516122 http://www.ncbi.nlm.nih.gov/entrez/query.fcgi?CMD=search&DB=pubmed.

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society for Analytical Cytology, vol. 56A No. 2 Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research an International Journal, vol. 95, No. 3, Sep. 1983.

Piumi, F, et al., Specific cytogenetic labeling of bovine spermatozoa bearing X or Y chromosomes using florescent in situ hybridization (FISH), Genet, Sel. vol. 33: 89-98 (2001).

Polge, C., Low-temperature Stonage of mammailian spermatozoa, Unit of Reproductive Physiology and Biochemistry, Cambridge.

Edited by Bell-Prince, C., NFCR Newsletter, http://www.ls.lanl.gov/NFCR/newsletter- Oc98/oct98.html Jan. 6, 2004.

Rasul, Z. et al., Changes in motion characteristics, plasma membrane integrity, and acrosome morphology during cryopreservation of buffalo spermatozoa, Journal of Andrology, vol. 22 No. 2, Mar.-Apr. 2001.

Rees, William A., et al, Betaine Can Eliminate the Base Pair Composition Dependence of DNA Melting; Biochemistry 1993, 32, pp. 137-144.

Rens, W. et al., An X-Y paint set and sperm FISH protocol that can be used for validation of cattle sperm separation procedures, Journals of Reproduction and Fertility, 121: 541-546 (2001).

Reyes-Mereno, C. et al., Characterizzion of Secretory Proteins from cultured Cauda Epidymal Cells that significantly sustain bovine sperm motility, Molecular Reproduction and Development 63: 500-509 (2002).

Rippel, N. et al., Transcervical insemination: Effects of variation in total sperm number/dose on fertility, 83rd Annual Fall Conference for Veterinarians, Oct. 2002.

Rizzo, W. et al.,Liposome-mediated transfer of simian virus 40 DNA and minichromosome into mammalian cells. J. Gen. Virol 64:911-919 (1983).

Ruch, F., Determination of DNA content by microfluorometry, Introduction to Quanitative Cytochemistry, pp. 281-294 (1966).

Saacke, R.et al., Semen Quality test and their relationship to fertility, 4th National Association at Animal Breeders, (1972).

Salisbury, G.W.,et al."Preservation of Bovine Spermatozoa in Yolk-Citrate Diluent and Field Results from its Use", Journal of Dairy Science, 1941, vol. 24(11),pp. 905-910.

Schroter, S.et al., The glycocalyx of the sperm surface, Human Reproduction Update: vol. 5, No. 4, pp. 302-313 (1999).

Schuster, T. et al., Isolation of motile spermatozoa from semen samples using microfluidics, Reproductive BioMedicine Online, vol. 7, No. 1 75-81, www.rbmonline.com/Article/847, Apr. 16, 2003.

Seidel, George E. Jr. "What about sexed semen?" Hoard's Dairyman, The National Dairy Farm Magazine, May 10, 2001.

Sexing Technologies, Welcome to sexing Technologies, http://www.sexingtechnologies.com, Dec. 11, 2003.

Shapiro Howard M. M.D.,Building Flow Cytometers Chapter 9, Practical Flow Cytometry, second edition, Property of Washington University Medical Library.

Sharpe, J. et al., Radially symmetric excitation and collection optics for flow cytometric sorting of aspherical cells, Cytometry, 29:363-370 (1997).

Shapiro, H., Re: cheap laser idea??, http://www.cyto.purdue.edu/hmarchiv/1998/1015.htm Feb. 3, 2004.

Smith, P.et al., Characteristics of a Novel Deep Red/ Infrared Fluorescent Cell-Permeant DNA Probe, DRAQ5, in Intact human Cells Analyzed by Flow Cytometry, Confocal and Multiphoton Microscopy, Cytornetry 40:280-291 (2000).

Stanger, J.et al., The Relationship between motility and the FITC-BSA binding Properties of Mouse epididymal spermatozoa, The Journal of Experimental Zoololy 227: 323-327 (1983).

Stanic,P. et al.,Comparison of protective media and freezing techniques for cryopreservation of human semen, http://www.ncbi.nlm.nih.gov/entrez/query.fcgi?CMD=search&DB=pubmed, Jul. 11, 2000.

Stewart,R., Georgia Beef Challenge, Livestock Newsletter Jan.-Feb. 2002.

Takacs, T.et al.,Flow Cytometric determination of the sperm cell number in diluted bull semen samples by DNA staining method, Acta Biochim.Biophys.Hung. vol. 22 No. 1, pp. 45-57 (1087).

Thurston,L. et al., Identification of Amplified restriction fragment length polymorphism markers linked to genes controlling boar sperm viability following cryopreservation, Biology of Reproduction 66: 545-554 (2002).

Tone,S.et al., A method of vital staining of mouse eggs using Hoechst dye,Department of Developmential Biology (1986).

Tubman,L.et al., Abstract:Normality of calves resulting from sexed sperm, http://www.cvm bs.colostate.edu/bms/abstract/ges 12.html Mar. 16, 2004.

Tucker,K.et al., Sperm separation techniques:Comparison of gradient products, Proceedings 2ed International workshop for Embryologists: Troubleshooting activities in the ART lab. (2002).

Van Dina, M.et al., Measurement of Mammalian Sperm Deoxyribonucleic by Flow Cytometry, The journal of Histochemistry and Cytochemistry vol. 25 No. 7 pp. 763-773 (1977).

Vazquez, J.et al., Nonsurgical Uterotubal Insemination in the Mare, Reproduction: Mare. vol. 44 (1998).

Vishwanath,R.et al., Storage of bovine semen in liquid and frozen state, Animal Reproduction Science 62: 23-53 (2000).

Washburn, S., Sex-Sorted Semen; Still several steps short of sensational, http://www.cals.ncsu.edu/ansci/extention/animal/news/april96/april1965.html.

Welch,G.et al., Sex preselection: Laboratory Validation of the sperm sex ratio of Flow sorted X- and Y- sperm by sort reanal ysis for DNA, Theriogenology 52:1343-1352 (1999).

Welch, G.et al., Fluidic and optical modification to a facs IV for flow sorting of X&Y Chromosomes bearing sperm based on DNA, International Society for Analytical Cytology (1994).

Wiltshire, M.et al., A Novel Deep Red/ Low infrared fluorescent flow cytometric pobe DRAQ5NO, For the Discrimination of inact nucleated cells in apoptotic cell populations, Cytometry 39:217-223 (2000).

Woelders, H. et al., Effects of Trehalose and Sucrose, Osmolality oh the Freezing medium, and cooling Rate on Viability and intactness of bull sperm after freezing and thawing, Cryobiology 35: 93-105 (1997).

Wolf, D., Lipid doamins in sperm plasma membranes, Molecular Membrane Biology 12: 101-104 (1995).

Wolf, D.et al., Changes in sperm plasma membrane lipid diffusibility after hyperactivation during In vitro capacitation in the mouse, The Journal of Cell Biology, vol. 102: 1372-1377(1986).

Wolf, D.et al., Diffusion and regionalization in membranes of maturing ram spermatozoa, The Journal of Cell Biology, vol. 98:1678-1684 (1984).

XY Files, Issue 1 Jun. 1999.

X V. Inc., Sex Selection Procedure, http://www.xyinc.com/sex select.html.

XY Files, Issue 4 Aug. 2000.

XY Files, Issue 2 Oct. 1999.

XY Files, Issue 3 Mar. 2000.

XY Files, Issue 5 Mar. 2001.

XY Files, Issue 6 Mar. 2002.

Lindsey, A. C., et al., Hysteroscopic insemination of mares with low numbers of nonsorted or flow sorted spermatozoa; Equine vet. J. (2002) 34(2) 128-132.

Sharpe, Johnathan, Advances in flow cytometry for sperm sexing, Unpublished paper, 2008.

Johnson, S.K., Possibilities with today's reproductive technologies. Available online at www.sciencedirect.com; Therio 64(2005) pp. 639-656.

Brogliatti, G. et al., Pregnancy Rates and First Born Calves by Artificial Insemination using Sexed Semen in Argentina: Therio. Jan. 2, 2002, vol. 57, No. 1. p. 369.

Palma, G. et al., Sperm Physiology: The Ability to Produce Embryos In Vitro using Semen from Bulls with a Low Non-Return Rate. Therio. p. 308.

Gottlinger, Christopher et al., Cell-Cooling in Flow Cytometry by Peltier Elements. Cytometry 7:295-297 (1986).

Abstracts: American Dairy Science Assoc., American Society of Animal Science, Jun. 22-26, 2003, Phoenix, AZ. J. Anim Sci. vol. 81, suppl. 1 /J. Dairy Sci., vol. 86, suppl. 1.

Blanchard, et al. Stallion Management. The Veterinary Clinins of North America, Equine Practice, 1992, vol. 8, No. 1, pp. 207-218.

Garner, et al. Effect of Semen Dilution on Bovine Sperm Viability as Determined by Dual-DNA Staining and Flow Cytometry. J. of Andrology, May/Jun. 1997, vol. 18, No. 3.

Goppert-Mayer. Uber Elementarakte mit zwei Quantensprungen Von Maria Copper-Mayer.

Gottinger, et al. Cell-Cooling in Flow Cytometry by Peltier Elements. Cytometry, 1986, 7, pp. 295-297.

Jasko, et al. Pregnancy Rates Utilizing Fresh, Cooled, and Frozen-Thawed Stallion Semen. Proc 38th Ann Convention AAEP, 1992, pp. 649-660.

Johnson, et al. Sex Preselection: High-Speed Flow Cytomeric Sorting of X and Y Sperm for Maximum Efficiency. Theriogenology, 1999, vol. 52, pp. 1323-1341.

Lamb. Synchronization of Estrus and Artificial Insemination on Replacernerit Beef Heifers Using Gonadotropin-Releasing Hormone, Prostaglandin F2a and Progesterone. J. Anim Sci, 2006, vol. 84 pp. 3000-3009.

Lindsey, et al. Hysteroscopic or Rectally Guided. Deep-Uterine Insemination of Mares with Sperinatozoa Stored 18 h at either 5° C. of 15° C. prior to Flow-Cytometric sorting. Animal Reprod Sci., Jan. 2005, vol. 85, issues 1-2, pp. 125-130.

Linge. Faltforsok med Djupfrost Sperma (Field Trials with Frozen Sperm). Farkotsel, 1972, vol. 52, pp. 12-13.

O'Brien, et al. Developement of Sperm Sexing and Associated Reproductive Technology for Sex Preselection of Captive Bottlenose Dolphins (*Tursiops truncatus*). Reproduction, Fertility and Development, 2008, 18, pp. 319-329.

O'Brien, et al. Semen Collection, Characterization and Preservation in a Beluga (*Delphinapterus leucas*). 1st International Workshop on Beluga Whale Research, husbandry and Management in Wild and Captive Environments, Mar. 2007.

O'Brien. Preliminary Developments of Sperm Sorting Technology in Non-human Primates, Biology of Reproduction, 2001, 64 (Suppl. 1), p. 158.

Prokofiev. Regoulyatsia Razmnozhenia Selskokhozyastvennykh Zhivotnykh, Leningrad, Naouka Publishing House, 1983, pp. 181-195.

Saladarriaga. Ovarian, hormonal, and Reproductive events Associated with Synchronization of Ovulation and Timed Appointment Breeding in Bos Indicus-Influenced Cattle Using Intravaginal Progesterone, gonadotropin-Releasing Hormone, and Prostaglandin F2a. J Anim Sci., 2007, vol. 85, pp. 151-162.

SAS, SAS/STAT ® User's Guide (Release 6.03), SAS Inst. Inc., Cary, NC, 1988.

Schafer, et al. Comparison of Progestin-Based Protocols to Synchronize Estrus and Ovulation before Fixed-Time Artificial Insemination in Postpartum Beef Cows. J. Anim Sci., 2007, vol. 85, pp. 1940-1945.

Schenk, et al. Pregnancy Rates in Heifers and Cows with Cryopreserved Sexed Sperm: Effects of Sperm Numbers per Inseminate, Sorting Pressure, and Sperm Storage before Sorting. Theriogenology, 2009, vol. 71, issue 5, pp. 717-728.

Shapiro. Practical Flow Cytometry. Third Edition. New York, 1994.

Solsberry, et al. Theory and Practice of Artificial Cow Insemination in USA. Moscow, KOLOS Publishing House, 1966, p. 346.

Suh, et al. High Pressure Flow Cytometric Sorting Damages Sperm. Theriogenology, 2002, vol. 64, issue 5, pp. 1035-1048.

Upreti, et al. Studies on Aromatic Amino Acid Oxidase Activity in Ram Spermatozoa: Role of Pyruvate as an Antioxidant, Animal Reproduction Science, 1998, vol. 51, pp. 275-287.

Van Munster. Geslachtsbepaling met interferometrie. Derde prijs NtvN-prijsvraag voor pas-gepromoveerden. 1999, 65/4, pp. 95-98.

Wintzer, et al. Krankheiten des Pferdes Ein Leitfaden fur Stadium und Praxiz. 1982. Parey, Berlin Hamburg XP002281450.

Chinese Patent Application No. 03818558.X, Office Action dated Mar. 24, 2006.

New Zealand Application No. 538462, Offcie Action dated Apr. 24, 2006.

Australian Patent Application No. 2003/265362, Examination Report dated Sep. 4, 2008.

New Zealand Patent Application No. 538462, Letters Patent dated Oct. 9, 2008 with effect from Aug. 1, 2003.

European Patent Application No. 03767201.1, Supplemental Search Report dated Oct. 24, 2006.

Canadian Patent Applicatio No. 2,532,376, Office Action dated Jun. 29, 2010, 4 total pages.

Japanese Patent Application No. 2004-526449, Notice of Allowance with allowed claims dated Aug. 29, 2010, 14total pages.

European Patent Application No. 03676201.1, Office Action dated Sep. 29, 2010, 5 total pages.

Bacetti et al. Ingertile speratozoa in a human carrier of robertsonian translocation 14;22. Fertility and Sterility, Nov. 2002, vol. 78, No. 5, pp. 1127-1130.

Beef Semen Online. High Fertility Semen. Website, http://www.beefsemenonline.co.uk, originally downloaded Mar. 11, 2009, 1 total page, United Kingdom.

Garner et al. Seminal plasma addition attenuates the dilution effect in bovine sperm. Theriogenology, Jul. 2001, 56:31-40.

Kaeoket et al. A preliminary study on using autologous and heterologous boar sperm supernatant from freezing processes as post-thawing solution: its effect on sperm motility. Trop Anim Health Prod, Feb. 2011, 43:1049-1055.

Liu et al. Research Progress of Factors Affecting the Quality of Silage. China Cattle Science, Sep. 2006, vol. 32, No. 5, pp. 59-62, p. 66 (abstract), China.

Heterogenous; Definition. Merriam-Webster Dictionary, http://www.merriam-webster.com, originally downloaded Jun. 14, 2012, 1 total page.

Moussa et al. Low density lipoproteins extracted from hen egg yolk by an easy method: cryoprotective effect on frozen-thawed bull semen. Theriogenology, Apr. 2002, vol. 57, pp. 1695-1706.

Napier. Fertility in the male rabbit. J. Reprod. Fertil., Aug. 1961, vol. 2, No. 3, pp. 273-289.

Parks et al. Cryopreservation of peregrine falcon semen and post-thaw dialysis to remove glycerol. Raptor Research, 1986, 20(1), pp. 15-20.

Perez-Garnelo et al. Post-thaw viability of European bison (*Bison bonasus*) semen frozen with extenders containing egg yolk or lipids of plant origin and examined with a heterologous in vitro fetilization assay. Journal of Zoo and Wildlife Medicine, Jun. 2006, vol. 37, Issue 2, pp. 116-125.

Roth et al. Scimitar-Horned Oryx (*Oryx dammah*) Spermatozoa Are Functionally Competent in a Heterologous Bovine In Vitro Fertilization after Cryopreservation on Dry Ice, in a Dry Shipper, or over Liquid Nitrogen Vapor. Biology of Reproduction, Feb. 1999, 60(2), pp. 493-498.

Ryder. Genus mixed-semen service increases conception rates. Farmers Guardian, Jan. 2003, 2 total pages, United Kingdom.

Suquet et al. Cryopreservation of sperm in marine fish. Aquaculture Research, Mar. 2000, 31(1), pp. 231-243.

Tartaglione et al. Prognostic value of spermatological parameters as predictors of in vitro fertility of frozen-thawed bull semen. Theriogenology, Oct. 2004, 62(7), pp. 1245-1252.

Tiersch. Strategies for commcercialization of cryptopreserved fish semen. Revista Basileira de Zootecnia, 2008, v. 37, Supplemento especial pp. 15-19, Brazil.

Vogt et al. Human Y chromosome azoospermia factors (AZF) mapped to different subregions in Yq11. Human Molecular Genetics, 1996, vol. 5, No. 7, pp. 933-943, Oxford University Press.

Wang et al. Study on application of frozen sexed X-semen of dairy cow AI. Journal of Guangzi Agric. and Biol. Science, Sep. 2006, vol. 25, pp. 191-192, abstract only in English.

* cited by examiner

HETEROGENEOUS INSEMINATE SYSTEM

This United States Non-Provisional Patent Application is a continuation-in-part of U.S. patent application Ser. No. 12/806,945, filed Aug. 24, 2010, which is a continuation of U.S. patent application Ser. No. 10/523,268, filed Jul. 7, 2005, which is the National Stage of International Patent Cooperation Treaty Patent Application No. PCT/US03/24460, filed Aug. 1, 2003, which claims the benefit of U.S. Provisional Patent Application No. 60/400,971, filed Aug. 1, 2002, each hereby incorporated by reference herein.

I. TECHNICAL FIELD

A heterogeneous inseminate including a first amount of sperm of a first animal and a second amount of sperm of a second animal of the same species, the first amount of sperm and the second amount of sperm sex-selected sperm of the same sex, useful in the in-vivo or in-vitro fertilization of an egg of a female animal of the same species for the production of sex-selected embryos and sex-selected offspring.

II. BACKGROUND

Pre-selection of sex has been accomplished in many species of livestock following the development of safe and reliable methods of separating sperm cells (also referred to as "sperm") into enriched X chromosome bearing and Y chromosome bearing populations. See for example methods and apparatus disclosed by WO 00/06193; WO 02/043574; WO 01/85913; WO 99/33956; WO 01/40765; WO 98/34094; WO 99/42810; WO 02/043486.

A significant problem with sex-selected sperm cells may be that separation of sperm cells at rates sufficient to produce sex-selected insemination samples or sex-selected inseminates which are viable or sufficiently fertile for commercial application by conventional technology has necessitated increasing fluid stream pressure of flow cytometers or flow sort instruments to about 50 pounds per square inch. With respect to sperm cells of many species of mammals entrained in fluid streams having flow characteristics resulting from this application of pressure, the viability, motility, or other fertility characteristics may be altered.

Another significant problem with sex-selected sperm cell inseminates or sex-selected sperm cell insemination samples can be the vast difference in sperm cell fertility characteristics which can vary greatly between samples. As such, success of artificial insemination performed under substantially identical conditions can result in correspondingly different pregnancy rates or cannot achieve the threshold of fertility in the context of conventional procedures for successful fertilization of eggs whether in-vitro or in-vivo.

Additionally, cryopreservation and thawing of sex-selected sperm can result in substantially reduced motility, percent intact acrosomes and post thaw survival time, all of which can militate against successful use of cryopreserved-thawed sex-selected sperm for the in-vitro or in-vivo fertilization of eggs of the same species of animal.

Additionally, certain animals, such as dairy cows, are known to have reduced fertility as compared to heifers. An adverse side effect of acquiring certain genetic traits advantageous to milk production can be concurrent with acquisition of genetic traits which lower fertility of dairy cows. Moreover, as to the example of dairy cows, it may also be desirable to increase the proportion of female offspring by the use of sex-selected sperm. In order to successfully breed animals having reduced fertility, especially in the instance of utilizing sex-selected sperm to increase the number of female offspring, it would be useful to have an inseminate, and a method of producing such inseminate, having increased fertility in order to increase pregnancy rates.

Therefore, a need exists for a method of increasing fertility of sperm within a sex-selected inseminate to overcome reduced fertility in inseminates whether due to low numbers of sperm contained in the inseminate, low fertility of sperm relating to animal to animal variation, the process of sex-selection, the low fertility of the female animal, or the like.

Additionally, a need exists for an assay from which fertility of sex-selected sperm cells can be compared directly in-vivo (for example, in conjunction with artificial insemination procedures) and in-vitro (for example, in conjunction with IVF procedures).

The instant invention addresses the need for a sex-selected inseminate having increased fertility to overcome reduced fertility due to limited numbers of sperm, low fertility of sperm relating to animal to animal variation or the process of sex-selection, and the low fertility of the female animal.

III. DISCLOSURE OF THE INVENTION

Accordingly, a broad object of the broad object of the invention can be to provide a heterogeneous inseminate (also referred to as a "heterogeneous insemination sample") in which a first amount of sperm and a second amount of sperm obtained from a corresponding first animal and a second animal are combined, the first amount of sperm or the second amount of sperm or both being sex-selected sperm, resulting in an increase in fertility of the first amount of sex-selected sperm or the second amount of sex-selected sperm such that the egg(s) of an animal can be fertilized whether in-vitro or in-vivo by one of the sperm of the first amount of sex-selected sperm or second amount of sex-selected sperm with increased success rates as compared to conventional inseminates (also referred to as a "conventional insemination sample") containing sex-selected sperm of only one animal, thereby increasing the number of embryos produced per unit of sex-selected sperm which can reduce the cost of embryo production.

Another broad object of the invention can be to provide a cryopreserved heterogeneous inseminate in which a first amount of sperm and a second amount of sperm obtained from a corresponding first animal and a second animal are combined, the first amount of sperm or the second amount of sperm or both being sex-selected sperm, resulting in an increase in fertility of the first amount of sex-selected sperm or second amount of sex-selected sperm upon being thawed, which can correspondingly increase in fertility in the first amount of sex-selected sperm or the second amount of sex-selected sperm or both such that the egg(s) of an animal can be fertilized whether in-vitro or in-vivo by one of the sperm of the first or second amount of sex-selected sperm with increased success rates as compared to conventional cryopreserved inseminates containing sex-selected sperm of only one animal, thereby increasing the number of embryos produced per unit of sex-selected sperm and can reduce the cost of embryo production.

Another broad object of the invention can be to provide devices and methods of using such devices to control sperm cell fertility characteristics of sperm cells isolated from semen obtained from a male of species of mammal, such as motility, viability, fertilization rate, cleavage rate, blastocyst rate, or the like.

Providing controlled sperm cell fertility in accordance with the invention can be achieved with the sperm cells obtained from numerous and varied species of mammals, including without limitation, mammals selected from the group consisting of a bovine species of mammal, an equine species of mammal, an ovine species of mammal, a canine species of mammal, a feline species of mammal, a swine species of mammal, a marine species of mammal, a deer species of mammal, a primate species of mammal, a goat species of mammal, or a species of mammal listed by Wilson, D. E. and Reeder, D. M., Mammal Species of the World, Smithsonian Institution Press, (1993), hereby incorporated by reference herein.

With respect to certain embodiments of the invention, controlled sperm cell fertility characteristics comprises affirmative selection of fertility characteristics in advance of isolating sperm cells from the semen of the male of the species of mammal and application of the invention to alter sperm cell fertility characteristics to provide the fertility characteristics desired. With respect to other embodiments of the invention, sperm cell treatment conditions are selected within a broader range of sperm cell treatment conditions that can be used treat sperm cells of a particular species of mammal to obtain sperm cells having controlled fertility characteristics. Controlled fertility characteristics can comprise a desired proportion of motile sperm cells, intact acrosomes, viable sperm cells within a population of treated sperm cells; or can comprise a desired cleavage rate of oocytes or rate of blastocyst formation when treated sperm cells are utilized to fertilize oocytes in vitro; or can comprise a desired pregnancy rate or sex ratio of offspring when treated sperm cells are utilized for artificial insemination.

With respect to certain embodiments of the invention, a greater proportion of motile sperm cells, a greater proportion of viable sperm cells, a greater proportion of intact acrosomes, or a greater number of fertile sperm cells within a treated sperm cell population can be achieved compared to conventional treatment of the same of sperm cell population. Certain embodiments of the invention allow provision of sperm cells having controlled fertility characteristics which are not substantially different than, or are substantially comparable to, the fertility characteristics of sperm cells in fresh ejaculated semen. In other instances, application of certain embodiments of the invention can, if desired, result in sperm cells having controlled fertility characteristics which are substantially different than those of sperm cells of fresh ejaculated semen. In particular, certain embodiments of the invention can be used to provide bovine sperm cells having controlled fertility characteristics or can be used to provide equine sperm cells having controlled fertility characteristics, which if desired can be provided with fertility characteristics substantially comparable to the fertility characteristics of bovine sperm cells or equine sperm cells within freshly ejaculated bovine or equine semen.

Another broad object of the invention can be to provide sperm cell insemination samples having controlled sperm cell fertility characteristics, such sperm cell insemination samples, without limitation, can be configured for artificial insemination of a female of a species of mammal, in vitro fertilization of oocytes, or intracytoplasmic injection of sperm cells, or the like.

Another broad object of the invention can be to provide methods of sex selecting sperm cells that can provide affirmative control of sperm cell fertility characteristics such as motility, viability, fertilization rate, cleavage rate, blastocyst rate, or the like. One aspect of this broad object of the invention can be to provide flow cytometry or cell sorting devices or methods of flow cytometry or cell sorting which allows affirmative control of the fertility characteristics of sex-selected sperm cells.

Another object of the invention can be to provide sex-selected bovine sperm cell insemination samples having controlled sperm cell fertility characteristics configured for artificial insemination of a female of a bovine species of mammal containing between about 100,000 and about 3,000,000 sex-selected bovine sperm cells having controlled sperm cell fertility characteristics.

Another object of the invention can be to provide sex-selected equine sperm cell insemination samples having controlled sperm cell fertility characteristics configured for artificial insemination of a female of an equine species of mammal containing between about 5,000,000 and about 50,000,000 sex-selected bovine sperm cells having controlled sperm cell fertility characteristics.

Another significant object of the invention can be to provide devices or methods of maintaining controlled sperm cell fertility characteristics of sperm cells with respect to processing of sperm cells, storage of sperm cells, or use of sperm cells, including, but not limited to, insemination of female mammal(s) or fertilization of oocyte(s).

Another significant object of the invention can be to provide methods of artificially inseminating females of a species of mammal with sperm cell insemination samples having controlled sperm cell fertility characteristics. With respect to certain embodiments of the invention, methods of insemination with a low or reduced number of sperm cells having controlled fertility characteristics compared to the usual number or typical number of sperm cells used in such artificial insemination procedures whether or not such sperm cells are separated into enriched X chromosome bearing or Y chromosome bearing sperm cell populations.

Another broad object of the invention can be to provide a method of assessing comparative fertility of sperm cell populations. Certain embodiments of the invention provide a method of assessing comparative fertility of sperm cells from different males of a species of mammal when sperm cells from each male are exposed to substantially the same flow cytometric treatment. Other embodiments of the invention provide a method of assessing comparative fertility of sperm cells from the same male of a species of mammal which are exposed to different flow cytometric treatments. Certain embodiments of the invention provide methods of showing comparative fertility of sperm cells having controlled fertility characteristics.

Naturally, further significant objects of the invention are made clear in the proceeding description of the invention.

IV. BRIEF DESCRIPTION OF DRAWINGS

V. MODE(S) FOR CARRYING OUT THE INVENTION

Now referring generally to FIGS. 1-9, embodiments of the invention can include a plurality of amounts of sperm (1) from corresponding plurality of male animals (2) of a species of mammal, as broadly defined above. Particular embodiments also include a plurality of amounts of sperm (1) obtained from a species of bird or fish. As to particular embodiments, each of the plurality of amounts of sperm (1) separately, or in combination as further described below, can then be entrained in a fluid stream (3) having flow characteristics. A fluid stream (3) within a conduit has flow characteristics influenced by the rheological properties of the fluid stream (3), the configuration or geometries of the conduit in which the fluid stream (3) flows, as well as external forces applied to the fluid stream (3) such as hydrostatic pressure, oscillatory vibrations, piezoelectric vibrations, oscillations in heat, or the like.

Importantly, these flow characteristics of the fluid stream (3) contribute to the amount of pressure required to move fluid within the conduit. As a non-limiting example, in flow cytometry, fluid moves within a relatively large cross sectional area and then within a relatively small cross sectional area past an analysis interface to a final collection point. This type of configuration or geometry along with rheological properties of the fluid stream can create localized forces such as compressive forces, sheer forces, or the like, which can have influence the physical integrity of particles such as sperm cells (6) entrained in the fluid stream (3).

Figure 1:
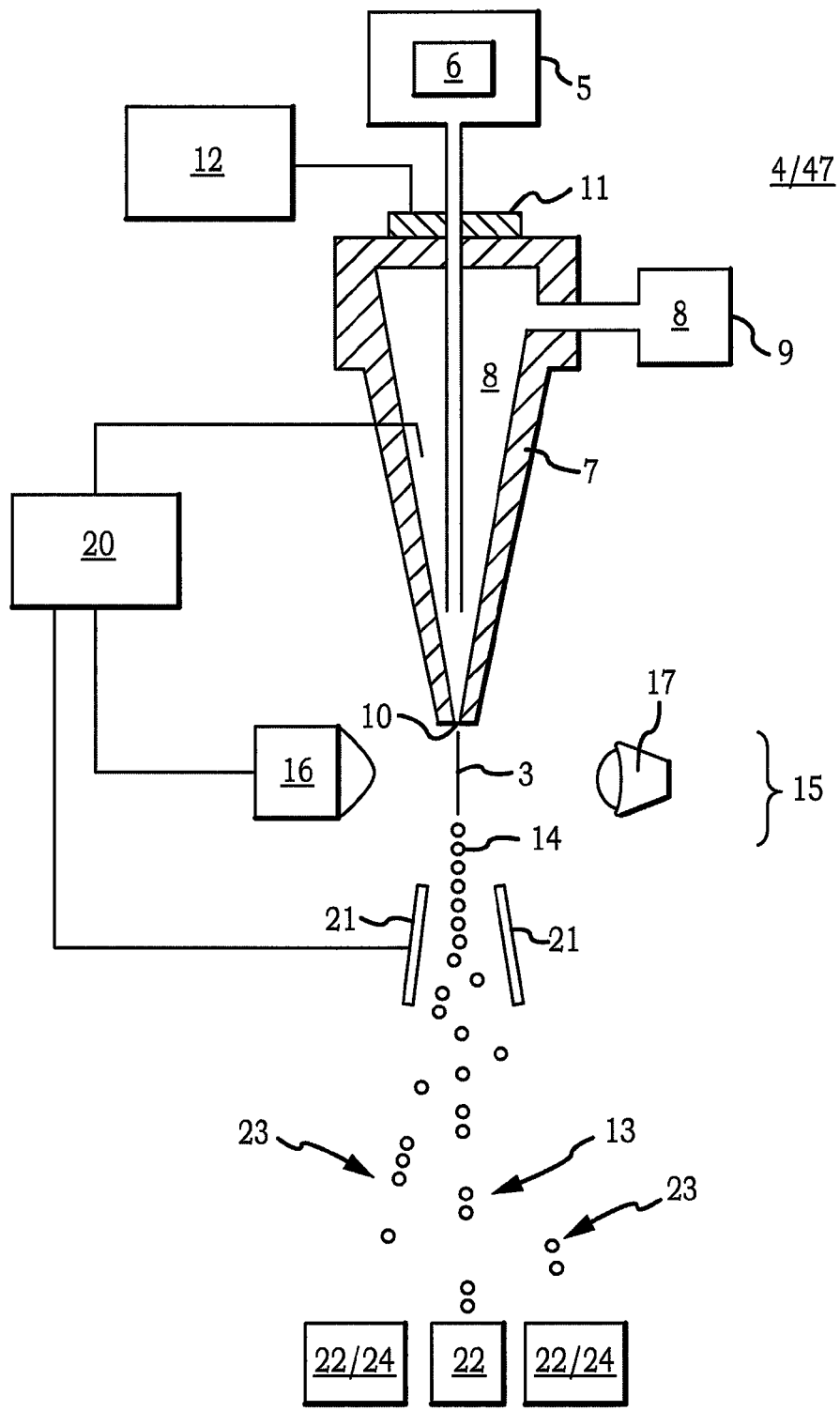
FIG. 1 is a schematic diagram of a sorter system according to a flow cytometer separation technique for the present invention.
Figure 2:
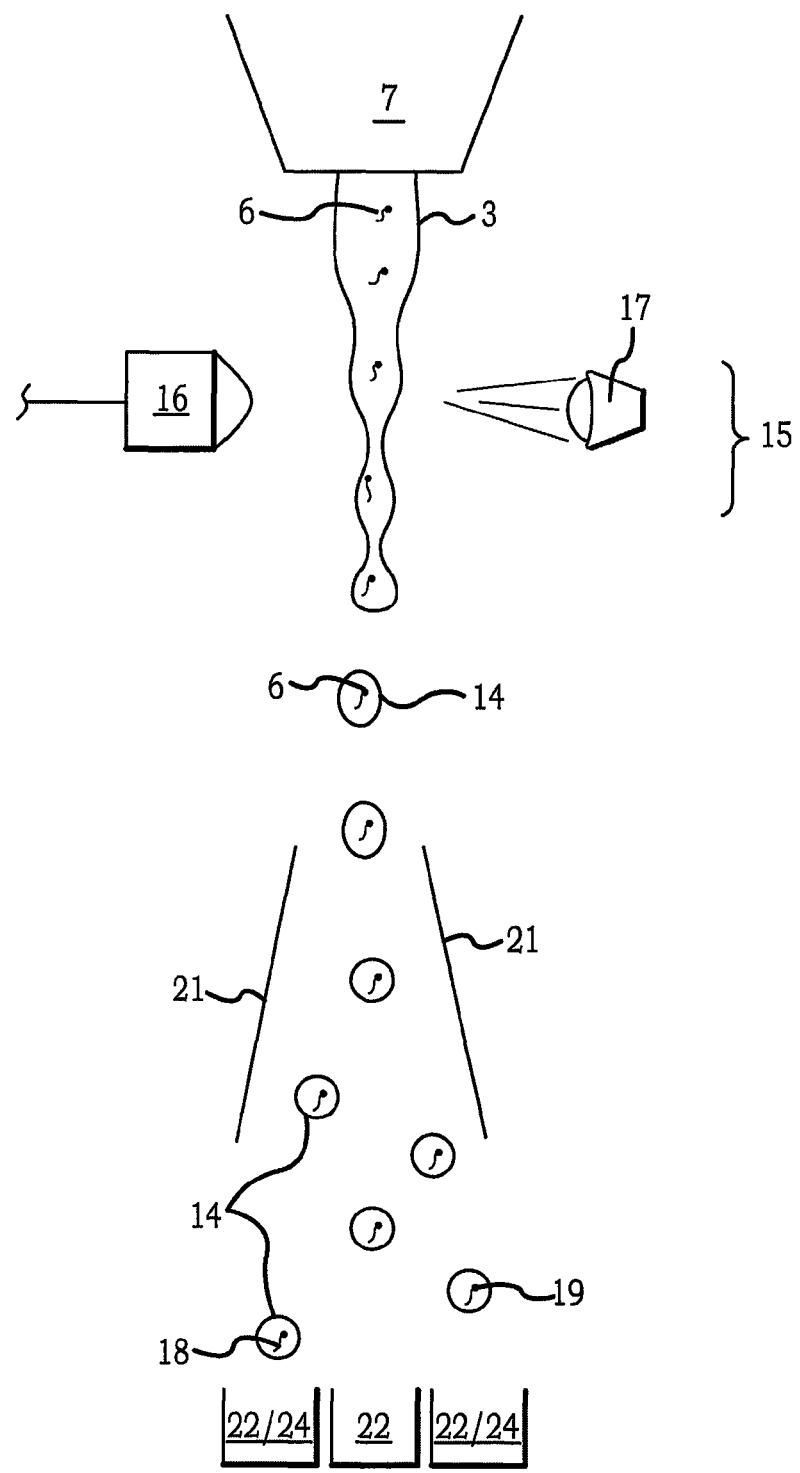
FIG. 2 is a diagram of the entrained cells in the free fall area of a typical flow cytometer.

With respect to those embodiment of the invention which include components of or steps involving flow cytometry or cell sorting as a means to analyze, separate based upon a sperm cell characteristic, sex select, or other wise process sperm cells (6), a conceptual non-limiting flow cytometer or cell sort instrument is shown in FIG. 1 and in FIG. 2.

A flow cytometer (4) or cell sort instrument includes all or a portion of the components shown in FIG. 1, including without limitation, a sperm cell source (5) which acts to establish or supply sperm (6) to analyze, separate, control fertility characteristics, or be otherwise treated.

Sperm (6) can be deposited within a nozzle (7) in a manner such that each of the sperm (6) can be surrounded by a sheath fluid (8). Any sheath fluid (8) compatible with the flow cytometer (4) or flow sort instrument and which provides an acceptable environment for sperm (6) during flow analysis or processing can be utilized with the invention, including without limitation, sheath fluids (8) which contain, individually or in various combinations, a phosphate buffered saline, a citrate solution (such as a 2.9% sodium citrate solution), a HEPES buffered solution, or the like.

The sheath fluid (8) can be delivered from a sheath fluid source (9) so that as the sperm cell source (5) supplies sperm (6), the sheath fluid (8) can be concurrently fed through the nozzle (7). In this manner, the sheath fluid (8) forms a sheath fluid environment for the cells. Since the various fluids are provided to the flow cytometer (4) at some pressure, they flow out of nozzle (7) at a nozzle orifice (10).

By providing an oscillator (11) which may be very precisely controlled through an oscillator control (12), pressure waves may be established within the nozzle (7) and transmitted to the sheath fluid (8) exiting the nozzle (7) at nozzle orifice (105). Since the oscillator (11) thus acts upon the sheath fluid (8), the stream (3) exiting the nozzle orifice (10) eventually and regularly forms droplets (14). Because each of the sperm (6) are surrounded by a sheath fluid environment, the drops (14) may contain within them individually isolated sperm (6).

Since the droplets (14) generally contain isolated sperm (6), the flow cytometer (4), or cell sorter instrument, can distinguish between and separate droplets (14) based upon one or more distinguishing sperm cell characteristic(s) of each sperm (6) contained within a droplet (14). This is accomplished through a sperm cell sensing system (15). The sperm cell sensing system (15) involves at least some type of a detector (16) responsive to differences in sperm cell characteristic(s) of the sperm (6) contained within each droplet (14).

One type of sperm cell sensing system (15) is discussed at length in U.S. Pat. No. 5,135,759 to Johnson, hereby incorporated by reference herein. As the Johnson patent explains for sperm (6), the cell sensing system (15) may cause an action depending upon the relative presence or relative absence of a particular dye which may be excited by some stimulant such as the beam of a laser (17). While each of a plurality of amounts of sperm (1) can be stained with a dye, the differing length of the X-chromosome and the Y-chromosome causes different levels of staining. Thus, by sensing the degree of dye present in each sperm (6) it is possible to discriminate between X-chromosome bearing sperm (18) and Y-chromosome bearing sperm (19) by their differing emission levels. Alternate optics, detection and sperm cell analysis systems are known which can also be used in accordance with the invention and it is intended that the description provided by the Johnson patent is for illustrative purposes so that the numerous and varied uses of the invention can be understood. See also, WO 01/85913, hereby incorporated by reference herein.

In order to achieve the separation and isolation of the appropriate cells in a flow cytometer or cell sort instrument separation technique, the signals received from the detector (16) are fed to a sorter discrimination system (20) which very rapidly makes the decision and can differentially charge each droplet (14) based upon whether the desired cell does or does not exist within that droplet (14). In this manner the sorter discrimination system (20) acts to permit the electrostatic deflection plates (21) to deflect droplets (14) based on whether or not they contain the a sperm (6) having certain sperm cell characteristics. As a result, the flow cytometer (4) or cell sorter instrument acts to separate the sperm (6) by causing them to land in one or more collection containers (22). Thus by sensing some property of the sperm (6), the flow cytometer (4) or cell sorter instrument can discriminate between sperm (6) based on a particular characteristic and place them in the appropriate collection container (22). In certain flow cytometers (4) or cell sorter instruments, the droplets (14) entraining X-chromosome bearing sperm (18) can be charged positively and thus deflect in one direction, while droplets (14) entraining Y-chromosome bearing sperm (19) can be charged negatively and thus deflect the other way, and the droplets (14) in a waste stream (13) (containing unsortable cells) remain uncharged and are delivered undeflected into a suction tube or the like.

Now referring primarily to FIG. 2, the process can be further understood in that the nozzle (7) emits a stream (4) which because of the oscillator (11) (not shown in FIG. 2) forms droplets (14). Since the cell source (5) (not shown in FIG. 2) may supply sperm (6) which as described by Johnson can be stained (or in certain embodiments of the invention unstained as when using differential interference contrast ("DIC") technology), the light emission generated by the beam generated by laser (or illumination source when using DIC technology) incident upon the dye (the sperm head when DIC technology is utilized) is differentially received by detector (16) so that the existence or nonexistence of a charge on each droplet (14) as it separates from stream (3) can be controlled by the flow cytometer (4). This control results in positively charged, negatively charged, and uncharged droplets (14) based upon their content. As shown in FIG. 2, certain droplets (14) are shown as deflected drops (23). These deflected drops (23) are those containing sperm (6) which can be one or the other sex. They are then deposited in the appropriate collector (22) thereby generating a population of sex-selected sperm cells (24).

Whether the fluid stream (3) occurs within the context of a flow cytometer (4), cell sorter, or other device which entrains sperm (6) within a fluid stream (3), the flow characteristics of the fluid stream (3) can be characterized and adjustment means for altering flow characteristics of the fluid stream (3) can be introduced to increase or decrease forces such as compressive forces, sheer forces, or the like, such that particles, cells, or sperm cells entrained in the fluid stream (3) can be physically, physiologically, functionally, or mechanically altered.

As such a selectably adjustable range of fluid stream characteristics for a flow path can be generated using the adjustment means and can be expressed as an incremental measure. For example, alteration of fluid stream characteristics within a flow cytometer (4) or cell sort instrument context can be incrementally adjusted and measured in pounds per square inch ("psi") and typically allow the incremental increase or decrease in the fluid stream pressure between about 20 pounds per square inch and 100 pounds per square inch with a commensurate increase or decrease in fluid stream or sheath fluid velocity.

In accordance with certain embodiments of the invention, sperm (6) of a particular species of mammal can be entrained in a fluid stream (3) having adjustable fluid stream flow characteristics. Fluid stream flow characteristics can then be selectably adjusted over an incrementally measured range in which the entrained sperm cells (6) remain viable. Sperm cell fertility characteristics are then assessed for each of a plurality of amounts of sperm (1) in correspondence to each of a plurality of flow characteristics generated within the measured range.

Subsequently, sperm cell fertility characteristics with respect to sperm (1) from a species of mammal or individual members of a species of mammal can be controlled and sperm cell insemination samples can be generated having the desired sperm cell fertility characteristics as further described below.

For example, a plurality of amounts of sperm cells (1) were obtained from each of six bulls. Each of the plurality of sperm cells (1) were stained with 125 μM Hoechst 33342 for 45 min at 34° C. The processed sperm cells (6) were bulk-sorted (passed through a flow cytometer (4) or cell sorter instrument without sorting into subpopulations), or sorted with a flow cytometer (4) having a nozzle (7) with an orifice with an internal diameter of 70 μM, into isolated populations of X-chromosome bearing sperm (18) or Y-chromosome bearing sperm (19) (or both) at about 95% accuracy with the fluid stream (3) having a pressure of at 30 psi, 40 psi, or 50 psi. Lowering the fluid stream pressure from 50 psi to 30 psi reduced sorting rate by only 2 to 3%.

The sperm cells (6) were subsequently cooled to 5° C. and concentrated by centrifugation, loaded into 0.25 ml artificial insemination straws (25) with about $2 \times 10^6$ total sperm cells (6) per 100 μL column, and frozen using a vapor freezing method along with unsorted controls. The sperm cells (6) in the artificial insemination straws (25) were subsequently thawed.

Sperm cells (6) were then evaluated with respect to various sperm cell fertility characteristics blindly by two observers at 30 and 120 min post-thaw for progressive motility, as well as by flow cytometry 105 min post-thaw, for percent live sperm cells by PI stain, and by CASA analysis 120 min post-thaw using the Hamilton Thorne system. The entire procedure was twice replicated. Factorial ANOVA indicated that both bull and pressure effects were significant (P<0.005, Table 1).

TABLE 1

Responses of sperm post-thaw to different system pressures during sorting.[a]

| | Pressure (psi) | | | |
|---|---|---|---|---|
| Response | 50 | 40 | 30 | Unsorted Control |
| 30 min motility (%) | 44.7 | 48.6 | 49.6 | 52.1 |
| 120 min motility (%) | 34.5 | 40.8 | 42.7 | 40.8 |
| Live sperm (%) | 51.7 | 55.7 | 57.8 | 58.5 |
| CASA total motility (%) | 25.1 | 37.2 | 40.9 | 34.8 |
| CASA ALH* | 6.0 | 7.6 | 7.8 | 8.8 |

[a]All statistically significant, P < .005.
*Amplitude of lateral head displacement.

Higher numbers mean less stiff and more normal motility. There were typical differences among bulls in all responses. However, the bull by treatment interactions were small with one exception, meaning findings apply similarly to most bulls in the population. The flow characteristics of the fluid stream (3) adjusted incrementally to increase pressure affected substantially all sperm cell fertility characteristics measured, however, only highly statistically significant ones are listed in Table 1.

As can be understood, there was significant change in sperm cell fertility characteristics between sperm cell samples taken at about 50 psi and at about 40 psi, and then a much smaller change between about 40 psi and about 30 psi, indicating that the effect on sperm cell fertility characteristics can not be assumed linear. For bovine sperm cells exposed to the flow characteristics described at 30 psi, sperm cell fertility characteristics were substantially the same as non-sorted controls or comparable to non-sorted controls, and for a few responses better, if sperm cells are to be used for insemination or artificial insemination of females of the bovine species. Similar procedures were conducted with sperm cells obtained from stallions with similar results and conclusions.

Sperm cell fertility characteristics can be controlled with respect to sperm cells obtained from mammals. For most species of mammals altering fluid stream characteristics to incrementally reduce fluid stream pressure, whether in the context of flow cytometry or otherwise, can result in a graded series of corresponding sperm cell samples having altered sperm cell fertility characteristics which may be used for a variety of procedures including artificial insemination, in vitro fertilization, or intracytoplasmic injection as described below.

The invention provides alternate tests to assess binomial responses such as pregnant/not pregnant, which typically require large numbers of animals per treatment to obtain statistical significance unless treatment differences are fairly large. One embodiment of the invention which can amplify differences in sperm cell fertility characteristics of sex-selected sperm due to treatment differences comprises competitive, or heterospermic, fertilization, mixing sperm of different treatments or males (whether or not sex-selected) (also referred to as a heterogeneous inseminate (26)) before insemination, and determining the proportion of embryos, fetuses or offspring derived from each male or treatment For example, fertility after sex selection of sperm cells (6) by flow cytometry or by cell sorting for DNA content at two different fluid stream pressures can be assessed using heterospermic insemination using sex as the genetic marker. Sperm cells (1) from each of two bulls was sorted into populations of X-chromosome bearing sperm (18) or Y-chromosome bearing sperm (19), or both, at about 95% accuracy with the fluid stream (3) pressure adjusted to either 30 psi or 50 psi. After concentrating sex-selected sperm cells (24) post-sort by centrifugation, $1 \times 10^6$ X-chromosome bearing sperm (18) sorted at 30 psi were placed in 0.25 mL straws with $1 \times 10^6$ Y chromosome bearing sperm (19) sorted at 50 psi for each bull, as well as the converse in other straws: $1 \times 10^6$ Y-chromosome bearing sperm at 30 psi plus $1 \times 10^6$ X-chromosome bearing sperm at 50 psi. These sex-selected sperm cells (18)(19), along with unsorted controls, were then frozen, thawed some months later, and inseminated into the body of the uterus of 85 Holstein heifers either 12 or 24 h after observed estrus with subgroups balanced across two inseminators.

Two months post-insemination, 81% of the 43 heifers becoming pregnant had fetuses of the sex (determined by ultrasound) corresponding to the sex of sperm processed at 30 psi. This differed from the 50:50 sex ratio expected (P<0.01), if there was no difference in sperm cell fertility characteristics of sperm cells sorted at the two pressures. The pregnancy rate with sex-selected sperm cells (24) at $2 \times 10^6$ sperm per dose was 51% (43/85); this was similar to the controls of $20 \times 10^6$ unsexed sperm per dose from the same ejaculates, 39% (9/23).

Another embodiment of the invention provides a method altering the cleavage rate and rate of blastocyst formation using sperm sex-selected sperm cells (24) having controlled sperm cell fertility characteristics. Two bovine sperm cell samples each having controlled fertility characteristics were generated by flow sorting bovine sperm cells at 40 psi and 50 psi respectively. Dose response of sperm cell concentration in the fertilization medium was conducted with X-chromosome bearing sperm cells (18) and Y-chromosome bearing sperm cells (19) from each sperm cell sample. Thus, a multifactorial procedure comprising 2 fluid stream pressures, 3 sperm cell concentrations (1, 0.33 and $0.11 \times 10^6$ sperm/mL), 6 bulls and 2 sexes can be conducted.

About 2,000 oocytes (27) (also referred to as "eggs") were aspirated from about 2 mm to about 8 mm follicles from slaughterhouse ovaries. Chemically defined media (CDM) were used throughout as described by Journal of Animal Sciences, 78:152-157 (2000), hereby incorporated by reference herein. Maturation took place in M-CDM supplemented with 0.5% FAF-BSA, 15 ng/mL NIDDK-oFSH-20, 1 µg/mL USDA-LH-B-5, 0.1 µg/mL $E_2$, 50 ng/µL EGF and 0.1 mM cysteamine for 23 h at 38.8° C. and 5% $CO_2$ in air. Sex-selected sperm cells (24) frozen with $2 \times 10^6$ cells per artificial insemination straw (25) were thawed and centrifuged at 400 g through 2 mL 45% and 2 mL 90% Percoll gradients for 20 min. Then the supernatant was discarded and 2 mL of FCDM supplemented with 0.5% FAF-BSA, 2 mM caffeine and 0.02% heparin was added to the sperm pellet and centrifuged at 500 g for 5 min. The supernatant was discarded leaving approximately 50 µL of sperm suspension. Matured oocytes (27) were washed once in FCDM and transferred in groups of 15 in 5 µL into 25 µL drops of FCDM under mineral oil. Fertilization took place by adding 10 µL of sperm suspension per drop for 18 h at 38.8° C., 5% $CO_2$ in air. Presumptive zygotes were cultured in CDM1 for 2 d and CDM2 for 4.5 d at 38.5° C., 5% $O_2$, 5% $CO_2$ and 90% $N_2$. On day 7.5, blastocyst development was evaluated: Quality 1 to 4 (1 being excellent and 4 being poor) and stage of development, 6 to 8 (6 full, 6.5 expanding, 7 expanded, 7.5 hatching and 8 hatched blastocysts). Data (Table 1) were analyzed by ANOVA and first deviation after arc sin transformation.

Cleavage (53.6 and 43.6%) and blastocyst (18.2 and 14.7%) rates were higher for procedures utilizing sperm cells having controlled sperm cell characteristics obtained at about 40 psi than at about 50 psi (P<0.01). There was no interaction between dose and pressure; therefore, there was a similar advantage to lower pressure at each sperm concentration. A clear dose response of sperm cell concentration for cleavage and blastocyst production was found (Table 2). Also, there were large differences among bulls (P<0.01) for both responses, and there was a bull×dose interaction (P<0.01) for % cleaved. The data indicate that the sperm dose should be $>1 \times 10^6$/mL for some bulls. Embryo quality was higher (P<0.01) for Y-chromosome bearing sperm (19) than for X-chromosome bearing sperm (18) (1.12 vs 1.57). Others have noted this for in-vitro fertilized embryos (28) when embryos were sexed, and this effect now is confirmed with sex-selected sperm (24).

TABLE 2

Cleavage (%, C) and blastocysts (%, B) per oocyte data presented by bull.

| Sperm conc. ($10^6$) | Bull | | | | | | | | | | | | | |
|---|---|---|---|---|---|---|---|---|---|---|---|---|---|---|
| | H023 | | H024 | | H025 | | H026 | | H027 | | H028 | | Avg | |
| | C | B | C | B | C | B | C | B | C | B | C | B | C | B |
| 0.11 | 18 | 1 | 6 | 1 | 4 | 11 | 36 | 15 | 20 | 7 | 54 | 15 | 30[a] | 8[a] |
| 0.33 | 44 | 4 | 7 | 2 | 72 | 31 | 62 | 21 | 29 | 11 | 68 | 18 | 47[b] | 14[b] |
| 1.0 | 56 | 18 | 35 | 14 | 85 | 43 | 83 | 34 | 72 | 27 | 85 | 29 | 69[c] | 28[c] |

[a,b,c] Values without common superscripts within groups differ, P < 0.01.

Fertility of sex-selected sperm (24) can be been low compared to unsorted control sperm, due partly to mechanical damage during sperm sorting by flow cytometry, as above-described. Lowering system pressure improved both sex-selected sperm cell (24) quality and fertility in IVF. The present study evaluated the effect of system pressure during sperm sorting and extended maturation of oocytes (27) on development of sex-selected embryos (8) after ICSI. Sperm from each of 3 bulls were stained with 125 μM Hoechst 33342 for 45 min at 34° C., sorted into populations of X-chromosome bearing sperm (18) and Y-chromosome bearing sperm (19) at 95% accuracy with the pressure of SX MoFlo®sorters at 40 or 50 psi, and then cryopreserved. Fifty bovine oocytes (27) obtained from slaughterhouse ovaries were placed per well with 1 mL of CDM1 supplemented with 0.5% FAF-BSA, 2 mM glucose, 50 ng/mL EGF, 15 ng/mL NIDDK-oFSH-20, 1 μg/mL USDA-LH-B-5, 1 μg/ml E2 and 0.1 mM cysteamine, and then matured for 24 h or 30 h at 38.5° C., 5% $CO_2$ in air. Cumulus cells of matured oocytes (27) were removed by vortexing, and oocytes (27) with a polar body were selected. Motile sex-selected sperm cells (24) from sorted frozen-thawed semen were recovered by centrifugation through 2 mL each of 45 and 90% Percoll, and the concentration adjusted to $4\times10^6$/mL. Matured oocytes were divided into two injection groups, ICSI and sham injection using a Piezo injection system. The outer diameter of the sperm injection pipette was 8-10 μM. All manipulations were performed at room temperature (24-25° C.). After injection, oocytes (27) were activated with 5 μM ionomycin for 4 min, cultured in 50 μL of CDM1 at 38.5° C. under 5% $CO_2$, 5% $O_2$ and 90% $N_2$, and assessed for cleavage at 72 h post-injection. Uncleaved oocytes from ICSI and sham injected groups were stained with orcein and evaluated for fertilization status. Cleaved embryos were further cultured and blastocyst development was evaluated on day 7.5 after injection. Data were subjected to ANOVA; the arc sin transformation was used for percentage data.

With 24 h matured oocytes (27), there were no differences (P>0.1) between sex-selected sperm (24) sorted at 40 versus 50 psi for cleavage or blastocyst rates, nor was there pressure× bull interaction. There were significant effects of bulls for all responses studied (P<0.05). When injected with sex-selected sperm (24) sorted at 40 psi, oocytes (27) matured for 30 h resulted in a higher cleavage rate than 24 h matured oocytes (22.9 versus 12.2%, P<0.05), with no difference P>0.1) in blastocyst rate. Overall blastocyst development was higher in ICSI than in sham injection (7.5 versus 1.3%, P<0.05). When uncleaved oocytes from 24 h maturation were evaluated for fertilization status, ICSI showed higher percentage with 2 polar bodies and/or decondensed sperm compared to sham injection (15.7 versus 1.7%, P<0.05). With 30 h matured oocytes there was no difference in fertilization status between those two groups. We conclude that there was no difference in cleavage or development to blastocysts after ICSI using motile sex-selected sperm (24) that had been sorted at 40 psi vs 50 psi.

In another embodiment of the invention, heterospermic insemination with heterogeneous inseminate (26) using sex as the genetic marker can be used to rank fertility of males and to rank fertility of sperm treatments not involving sperm sexing. Current in-vitro tests of sperm function are not highly correlated with male fertility, and homospermic inseminations require hundreds of inseminations per treatment to obtain accurate fertility data. Heterospermic insemination with heterogeneous inseminates (26) generated by mixing the sperm of two or more males, provides an accurate estimation of relative fertility in most species examined.

Frozen, flow-sorted sperm from 4 groups of 4 bulls (2) were thawed and inseminated into heifers 12 h or 24 h following onset of estrus in all combinations of 3 bulls within groups (ABC, ABD, ACD, BCD). Equal numbers of progressively motile sex-selected sperm (24) were inseminated from each bull, totaling 600,000 motile sex-selected sperm (24) post-thaw. Half of each heterogeneous inseminate (26) was deposited into each uterine horn. Embryos were collected nonsurgically 14.5 to 20 days following estrus. Collections yielded 165 elongating embryos from 332 heifers (48%). Polymorphic DNA markers were used to genotype embryos to determine the sire of each embryo biopsy. After genyotyping, 118 of the 165 embryos could be assigned a specific sire. Heterospermic indices for ranking each bull group were calculated using the maximum likelihood analysis theorem. Each bull within groups was ranked based on these indices (Table 3). In group 1, the fertility of the poorest bull was significantly lower (P<0.05) than two other bulls. In group 2, the dominant bull had the highest index (P<0.05). Similar distinctions could be made in groups 3 and 4. However, in three of the groups the fertility of some bulls was not clearly high or low (P>0.05).

TABLE 3

| Heterospermic indices ± SE for individual bulls within groups. | | | |
|---|---|---|---|
| Group 1 | Group 2 | Group 3 | Group 4 |
| $1.47 \pm .41^a$ | $2.43 \pm .43^a$ | $1.68 \pm .44^a$ | $0.92 \pm .36^{a,b}$ |
| $0.44 \pm .27^{a,b}$ | $0.22 \pm .15^b$ | $1.09 \pm .39^{a,b}$ | $0.46 \pm .20^a$ |
| $1.84 \pm .46^a$ | $0.90 \pm .35^b$ | $0.83 \pm .31^{a,b}$ | $2.02 \pm .40^b$ |
| $0.25 \pm .17^b$ | $0.45 \pm .23^b$ | $0.40 \pm .22^b$ | $0.59 \pm .24^a$ |

$^{a,b}$Indices without common superscripts differ, P < 0.05.

With these procedures, an average of 30 genotyped in-vivo embryos (8) per group of 4 bulls enabled detection of bulls with clearly differing fertility. Sperm treatments also could be evaluated with this technique. This in-vivo test requiring few female animals (29) rapidly provides information concerning which bulls have relatively high or low fertility.

The population of calves (30) (also referred to as "offspring") obtained by artificial insemination (31) of female animals (29) with sex-selected sperm cells (24) in accordance with the invention are virtually identical to controls using unsex-selected sperm cells. Furthermore, artificial insemination (31) of female animals (29) with sex-selected sperm (24) resulted in approximately 90% of calves (30) of the planned sex. As described above, sperm cells (6) can be sex selected on the basis of DNA content by flow cytometry or by cell sorting after staining with H33342. The sex-selected sperm cells (24) can then be cryopreserved as described in Theriogenology, 52:1375 (1999), hereby incorporated by reference herein.

Estrus can be synchronized in heifers and cows (female animals (29)) of various beef and dairy breeds, either by feeding 0.5 mg melengestrol acetate (MGA) daily for 14 d followed by 25 mg prostaglandin $F_2$ ($PGF_2$) im 17 to 19 d later or injection of 25 mg $PGF_2$ im at 12-d intervals. Artificial insemination (31) with either frozen-thawed sex-selected insemination samples or frozen-thawed sperm from the same ejaculate have been accomplished at either 12 h or 24 h after initial observation of estrus. For each breeding group, about ⅔ of the inseminations were with sexed sperm while control sperm were used in the remainder. Pregnancy and fetal sex were diagnosed by ultrasound 2 months later.

Cattle were managed at 13 farms through calving and weaning under differing levels of management (N=49 to 228 per farm). Data collected included gestation length, birth weight, calving ease (1=normal to 4=Caesarian), weaning weight, neonatal deaths, and deaths from birth to weaning. Not all farms recorded birth and weaning weights. Data were subjected to factorial analysis of variance with factors: management groups, sex-selected sperm cells (24) versus control sperm, and sex of calves (30). The arc sin transformation was used for percentage data. Least-square means are in Table 4.

TABLE 4

Calving results from sexed and control calves.

| Treatment | N | Gestation length (d) | Neonatal death (%) | Calving ease | Birth weight (kg) | Live at weaning (%) | Weaning weight (kg) |
|---|---|---|---|---|---|---|---|
| Sexed[a] | 574 | 279 | 3.9 | 1.31 | 34.3 | 92.0 | 239 |
| Control | 385 | 279 | 5.9 | 1.30 | 34.1 | 88.9 | 239 |

[a]No significant differences (P > 0.1) for any response.

There were no differences (P>0.1) between calves from sexed versus control groups for any response studied, nor were there significant interactions. There were significant effects of management groups for all responses studied (P<0.001 for all except % alive at weaning, P<0.02). Also, there were significant differences (all P<0.001) between female and male calves (30) for birth weight: 32.2 and 35.5 kg; weaning weight: 232 and 246 kg; calving difficulty: 1.20 and 1.42; and gestation length: 278 and 280 d. The sex ratio of the control calves (30) was 51.0% males (N=382). Sorted populations of X-chromosome bearing sperm (18) resulted in 87.7% females, while sorted populations of Y-chromosome bearing sperm (19) produced 93.6% males (N=94). A few calves that were dead at birth did not have sex recorded and are not included. The recent development of flow cytometric separation of stallion spermatozoa has resulted in the production of normal foals with preselected sex. (Lindsey A. C., Morris L. H., Allen W. R., Schenk J. L., Squires E. L., Bruemmer J. E. Equine vet J. 2002, 34: 128-132).

For this technology to be accessible, semen will be transported from the flow cytometer (4) to the mare. This study examined the longevity and acrosome status of fresh stallion spermatozoa after sex pre-selection. Three ejaculates from each of 7 stallions were collected by artificial vagina and shipped to the laboratory at 20° C. for 2-6 h in a skim milk-glucose extender (1:1 v/v). The semen was centrifuged at 400 g for 10 min and the seminal plasma removed. The sperm pellet was re-suspended to $100\times10^6$/mL in Kenneys modified Tyrodes medium (KMT), stained with Hoechst 33342 (5 mg/mL, Sigma-Aldrich, St. Louis Mo.), incubated for 30 min and subjected to flow cytometry. The sex-selected sperm cells (24) were centrifuged and resuspended to $40\times10^6$ mL in KMT in 250 μL aliquots for 48 h storage at either 4° C. or 20° C. The total progressive motility (TPM) and the acrosome status of the sex-selected sperm cells (24) were evaluated prior to sorting and at 0, 2, 12, 24, 36 and 48 h after sorting. The TPM was evaluated microscopically and acrosomes stained with FITC-PNA (Sigma-Aldrich) and classified as intact, patchy or lost. The effect of stallions, time and storage temperatures were analyzed using the Proc GLM procedure and least means comparisons made (SAS Institute).

There was an effect of stallion (p=0.03) on sperm motility and on the proportion of intact acrosomes over time. Staining and incubating the spermatozoa with Hoechst 33342 resulted in a decrease in the proportion of intact acrosomes (Table 5). However, the proportion of intact acrosomes observed after sorting was higher than in the sperm population prior to sorting. The proportion of intact acrosomes declined (p<0.0001) as the lost acrosomes increased (p<0.0001) during 48 h after sorting, but there was no effect of time on the proportion of patchy acrosomes. There was a significant effect of sperm storage temperature after sorting such that that storage for 12 h at 20° C. resulted in higher motility than storage at 4° C. Sex-sorting spermatozoa by flow cytometry results in the selection of a population of spermatozoa which can maintain acrosome integrity for 24 h, equivalent to fresh spermatozoa. The maintenance of sperm longevity for 12 h after FACS separation should enable sex-sorted spermatozoa to be shipped to mares located some distance from the site of the flow cytometer.

TABLE 5

The motility and acrosome status of flow sorted spermatozoa over time.

| Stage of Processing | | TPM | Acrosome intact |
|---|---|---|---|
| Prestain | | 50.7 ± 10.2 | 57.1 ± 28.2 |
| Post stain | | 42.0 ± 17.1 | 42.3 ± 26.7 |
| Post incubation | | 48.0 ± 15.7 | 34.9 ± 27.1[a] |
| 0 h | Post sort | 49.9 ± 18.3 | 60.2 ± 22.3[b] |
| 2 h | 4° C. | 34.3 ± 19.3 | 47.1 ± 28.3 |
| | 20° C. | 40.8 ± 21.8 | 53.9 ± 24.5 |
| 12 h | 4° C. | 8.5 ± 12.8[a] | 59.8 ± 19.7 |
| | 20° C. | 27.0 ± 21.0[b] | 66.6 ± 12.0 |
| 24 h | 4° C. | 4.8 ± 12.9 | 56.2 ± 16.8 |
| | 20° C. | 17.2 ± 17.9 | 64.3 ± 16.4 |
| 48 h | 4° C. | 0.0 ± 0.0 | 32.7 ± 25.0 |
| | 20° C. | 5.1 ± 8.6 | 41.6 ± 24.0 |

[a,b]Values within a column with different superscripts are significantly different (p < 0.05).

Foals of predetermined sex have been accurately and reliably produced in a research setting (Lindsey et al., Equine Vet. J. 2002, 34: 128-132). Sex-sorted sperm would be more efficiently utilized by the industry, however, if froze-thawed sex-sorted sperm were available. The objective of this study was to compare the motion characteristics of sperm that had been stored for 18 h at 15° C., flow-sorted, and then frozen, to sperm that had been cryopreserved immediately following shipment at 18 h at 15° C. Two ejaculates were used from each of five stallions. Following collection, sperm for both treatments were extended to $25\times10^6$/mL in a Kenney+Modified Tyrodes (KMT) medium and stored in a water bath at 15° C. for 18 h. After storage, sperm were allowed to reach ambient temperature (about 22° C.) prior to centrifugation at 600 g for 10 min. Seminal plasma was removed and the sperm pellet re-suspended to $500\times10^6$/mL in KMT. An aliquot of sperm was removed (Control) from this sample, extended to $87\times10^6$/mL in a skin-mild, egg yolk freezing extended (4% glycerol; FR5), and allowed to slow cool to 5° C. for 90 min before freezing in liquid nitrogen vapor. A second aliquot (Flow-sorted) of sperm was extended to $100\times10^6$/mL in KMT, stained with Hoechst 33342 (5 mg/mL, Sigma-Aldrich, St. Louis Mo.), incubated for 30 min, and subsequently sorted by flow-cytometry. Sorted sperm was centrifuged at 850 g for 20 min, resuspended to 87×10⁶/mL in FR5, and allowed to cool slowly to 5° C. for 90 min prior to cryopreservation. Sperm for both treatments were packaged in 0.25 mL straws, and each straw contained 20 million sperm. Sperm were evaluated (blindly) for visual progressive motility (2 observers) at 30 and 90 min post-thaw. An aliquot of sperm from each straw was diluted in both KMT and in KMT containing 2 mM caffeine. Samples were allowed to equilibrate for 5-10 min at 37° C. prior to evaluation. A second straw of each treatment was evaluated (with and without caffeine) using the Hamilton-Thom Motility Analyzer (CASA). Results are in Table 1. Differences in motion parameters were determined by ANOVA. According to most measured responses, flow-sorting was detrimental to sperm motility. Additionally, 2 mM caffeine improved many sperm responses. There was an interaction whereby caffeine improved some responses more for sorted sperm than for control sperm. Therefore, the damage caused by sorting can be partially compensated for by caffeine. It is possible that similar compensation may occur in the mare reproductive tract Studies are currently in progress to compare the fertility of stored, cryopreserved stallion sperm to that of sperm that has been stored and sorted prior to cryopreservation.

TABLE 6

| Treatment | Vis 30 | Vis 90 | CASA Tot | CASA Prog | VAP | VSL | VCL | ALH | BCF | STR | LIN |
|---|---|---|---|---|---|---|---|---|---|---|---|
| C-Control | 50$^a$ | 41$^a$ | 64$^a$ | 60$^a$ | 94$^a$ | 80$^a$ | 164$^a$ | 6.19$^a$ | 33$^a$ | 83$^a$ | 50$^a$ |
| Control | 45$^a$ | 40$^b$ | 50$^b$ | 44$^b$ | 82$^a$ | 69$^a$ | 144$^a$ | 5.73$^a$ | 33$^a$ | 82$^a$ | 50$^a$ |
| C-Sorted | 32$^b$ | 31$^c$ | 32$^c$ | 21$^c$ | 48$^b$ | 38$^b$ | 98$^b$ | 4.75$^b$ | 41$^b$ | 73$^b$ | 39$^b$ |
| Sorted | 18$^c$ | 16$^d$ | 24$^d$ | 12$^d$ | 39$^b$ | 30$^b$ | 80$^b$ | 4.51$^b$ | 37$^c$ | 69$^b$ | 38$^b$ |

$^{a,b,c,d}$Values in the same column without common superscripts differ (P, 0.05).
C-treatments stimulated with 2 mM caffeine.

Cow elk 3-6-yr of age in Colorado and Minnesota were synchronized for estrus in September by insertion of a progesterone CIDR into the vagina for 12-14 d. Upon removal of the CIDR, 200 IU of eCG was administered intramuscular and elk were timed-inseminated 60 h later. Fresh semen was collected via electro-ejaculation from a 5-yr old bull elk and slowly cooled over 4 h to about 20° C. for transportation as a neat ejaculate to the sperm-sorting laboratory. The ejaculate was concentrated to 1×10⁹ sperm/mL for straining by centrifuging 1.5 mL aliquots for 10 sec at 15,000×g. Semen was incubated in 112 μM Hoechst 33342 at 200×10⁶ sperm/ml in a TALP medium for 45 min at 34° C., and then diluted to 100×10⁶/mL for sorting. Sperm were sorted on the basis of differing DNA content of X and Y chromosome-bearing sperm. X chromosome-bearing elk sperm contain 3.8% more DNA than Y chromosome-bearing sperm. Sperm were flow-sorted over a 4 h period using MoFlo®SX operating at 50 psi with a TRIS-based sheath fluid. The 351 and 364 bands of an argon laser, emitting 150 mW, excited Hoechst 33342 dye bound to DNA. Both X and Y chromosome-bearing sperm were collected (about 92% purity as verified by reanalyzing sonicated sperm aliquots for DNA) were collected at about 4,700 sperm/sec into tubes containing 2 mL of 20% egg yolk-TRIS extender. Sorted volumes of 15 ml were sequentially collected. Approximately 110×10⁶ sperm of each sex were sorted and cooled to 5° C. Cover 90 min. An equal volume of glycerol (12%) containing extender was added to the sorted volume at 5° C. Sorted sperm aliquots containing 30-ml were concentrated by centrifugation at 4° C. for 20 min at 850×g. Sperm pellets were pooled, adjusted to 21.7×10⁶ sperm/mL and loaded into 0.25 mL straws. Each straw, containing 5×10⁶ total sperm, was frozen in liquid nitrogen vapor. As a control, 5×10⁶ total sperm from the same ejaculate were frozen in 0.25 mL straws at the same time as the sexed sperm. After thawing for 30 sec at 37° C., 65% and 60% of sperm (control and sexed, respectively) were progressively motile as determined by visual estimates. Cows at 3 different locations and management schemes were inseminated using routine trans-cervical semen deposition in the uterine body. Pregnancy was determined 40 d post insemination by assaying blood for Pregnancy-Specific Protein B (Bio Tracking, Moscow, Id.). Ten cows at one location were in poor condition at the time of insemination and no pregnancies were achieved with sexed or control sperm. The pregnancy rate at the other locations with sexed sperm (61%; 11/18) was similar to that for control inseminates (50%; 3/6). These pregnancy rates (sexed and controls) resulted from fewer sperm than are used in normal elk artificial insemination. Nine of eleven (82%) of sexed calves were of the predicted sex.

Figure 3:
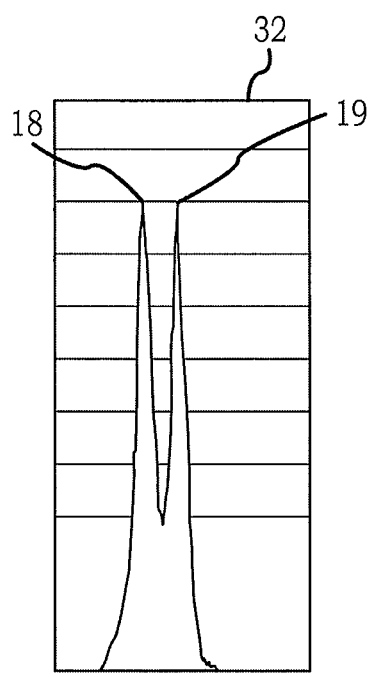
FIG. 3 is a plot which shows the level of resolution achieved between an X-chromosome bearing population and a Y-chromosome bearing population resulting from the separation of sperm in a first amount of sperm obtained from a first male animal using a flow cytometer in accordance with the method shown in FIG. 9.
Figure 4:
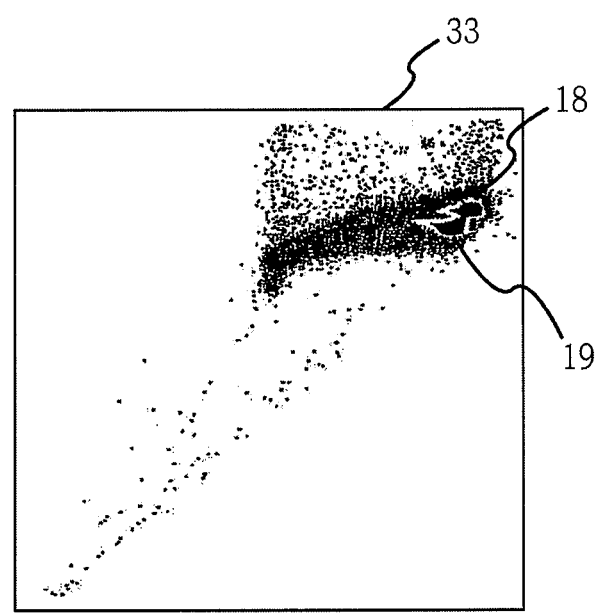
FIG. 4 is a bivariate plot which shows separation of sperm in a first amount of sperm obtained from a first animal separated into an X-chromosome bearing population and a Y-chromosome bearing population using a flow cytometer in accordance with the method shown in FIG. 9.
Figure 5:
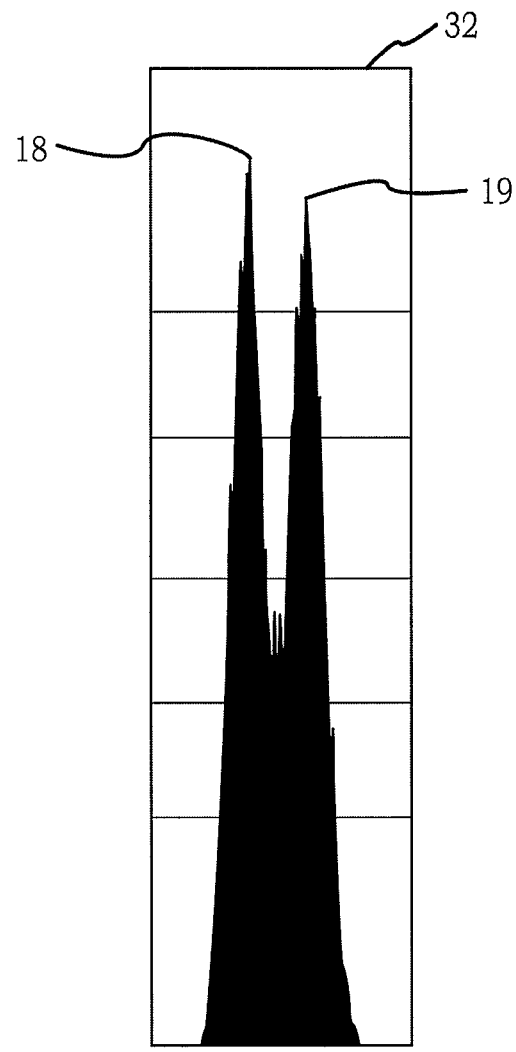
FIG. 5 is a plot which shows the level of resolution achieved between an X-chromosome bearing population and a Y-chromosome bearing population resulting from the separation of sperm of a first amount of sperm obtained from a first male animal combined with a second amount of sperm obtained from a second male animal using flow cytometry in accordance with the method shown in FIG. 8.
Figure 6:
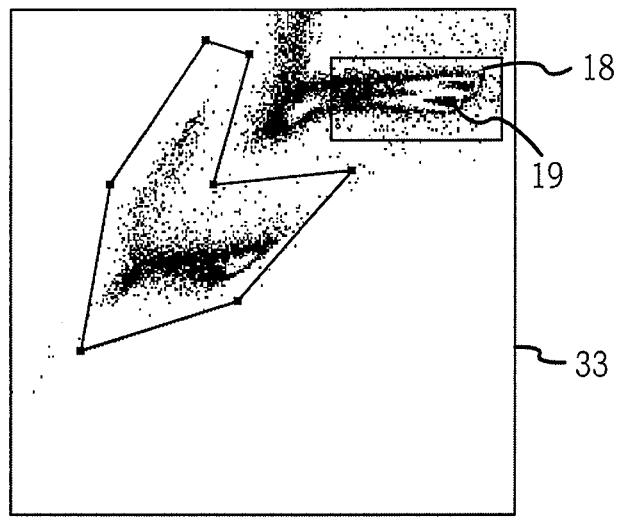
FIG. 6 is a bivariate plot which shows the level of resolution achieved between an X-chromosome bearing population and a Y-chromosome bearing population resulting from the separation of sperm of a first amount of sperm obtained from a first animal combined with a second amount of sperm obtained from a second animal using flow cytometry in accordance with the method shown in FIG. 8.
Figure 9:
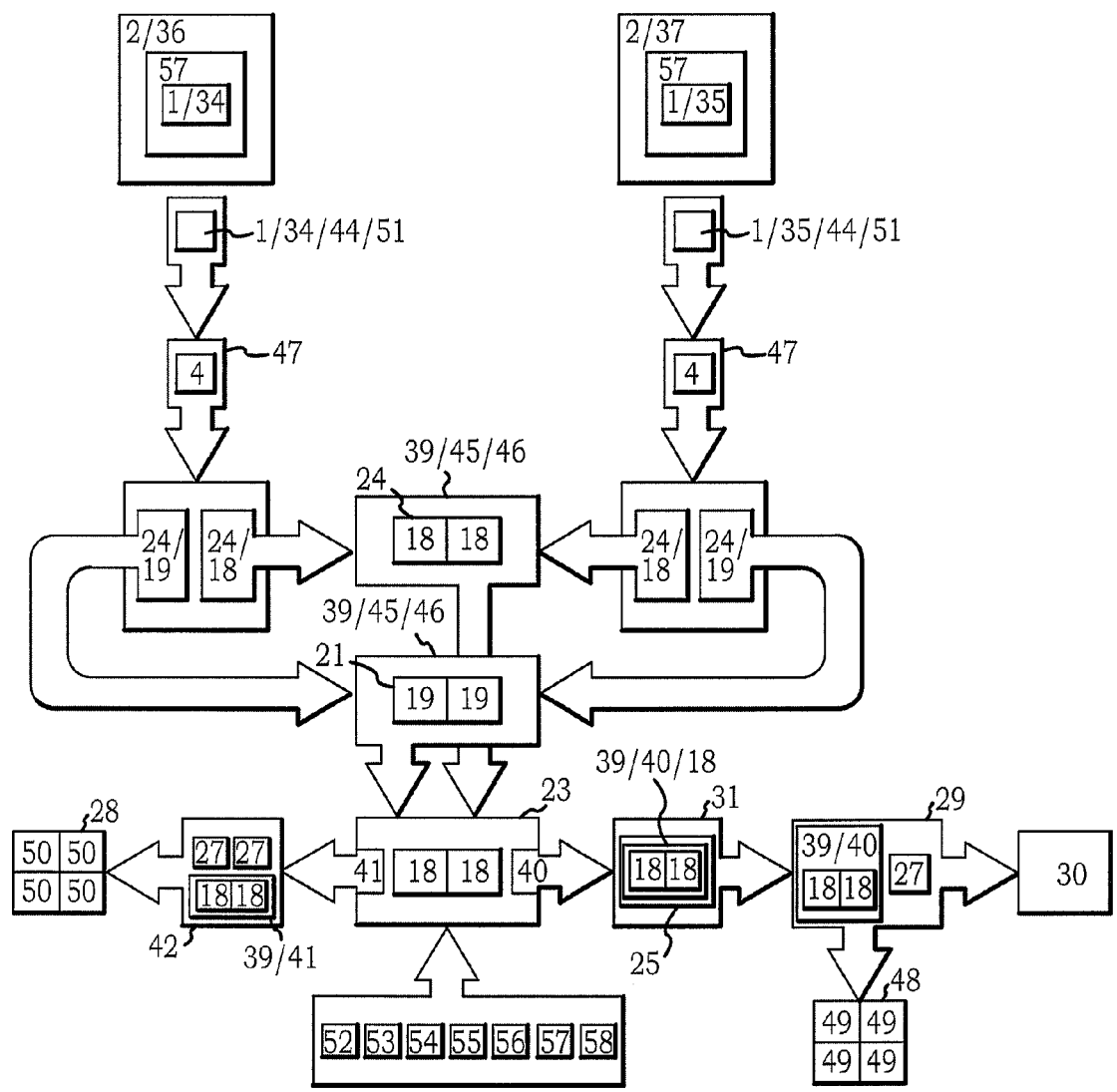
FIG. 9 is a block diagram which shows a particular method of how to make and use an embodiment of the inventive heterogeneous inseminate.

Now referring primarily to FIGS. 3, 4, and 9 a univariate plot (or histogram) (32) (FIG. 3) and a bivariate plot (33) (FIG. 4) can be generated using a flow cytometer (4) to separate or sort a first amount of sperm (34) or a second amount of sperm (35) or each of a plurality of amounts of sperm (1) from a corresponding first male animal (36), second male animal (37) or plurality of male animals (2) into subpopulations of X-chromosome bearing sperm (18) and Y-chromosome bearing sperm (19) prior to being combined to achieve an embodiment of the sex-selected heterogeneous inseminate (26), as above described. The histogram (32) (FIG. 3) and the bivariate plot (33) (FIG. 4) show that the mixture of X-chromosome bearing sperm (18) and Y-chromosome bearing sperm (19) in each of a first amount of sperm (34) or second amount of sperm (35) or plurality of amounts of sperm (1) can be resolved into separate corresponding subpopulations of X-chromosome bearing sperm (18) and subpopulations of Y-chromosome bearing sperm (19).

Figure 7:
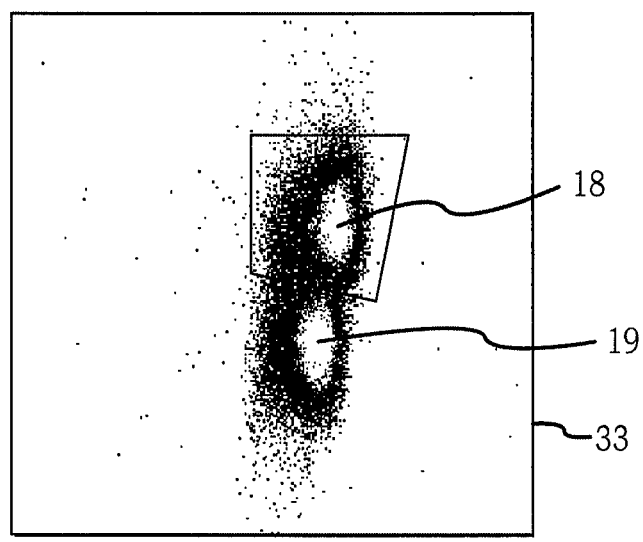
FIG. 7 is an illustration which shows an enlarged portion the bivariate plot shown in FIG. 6.
Figure 8:
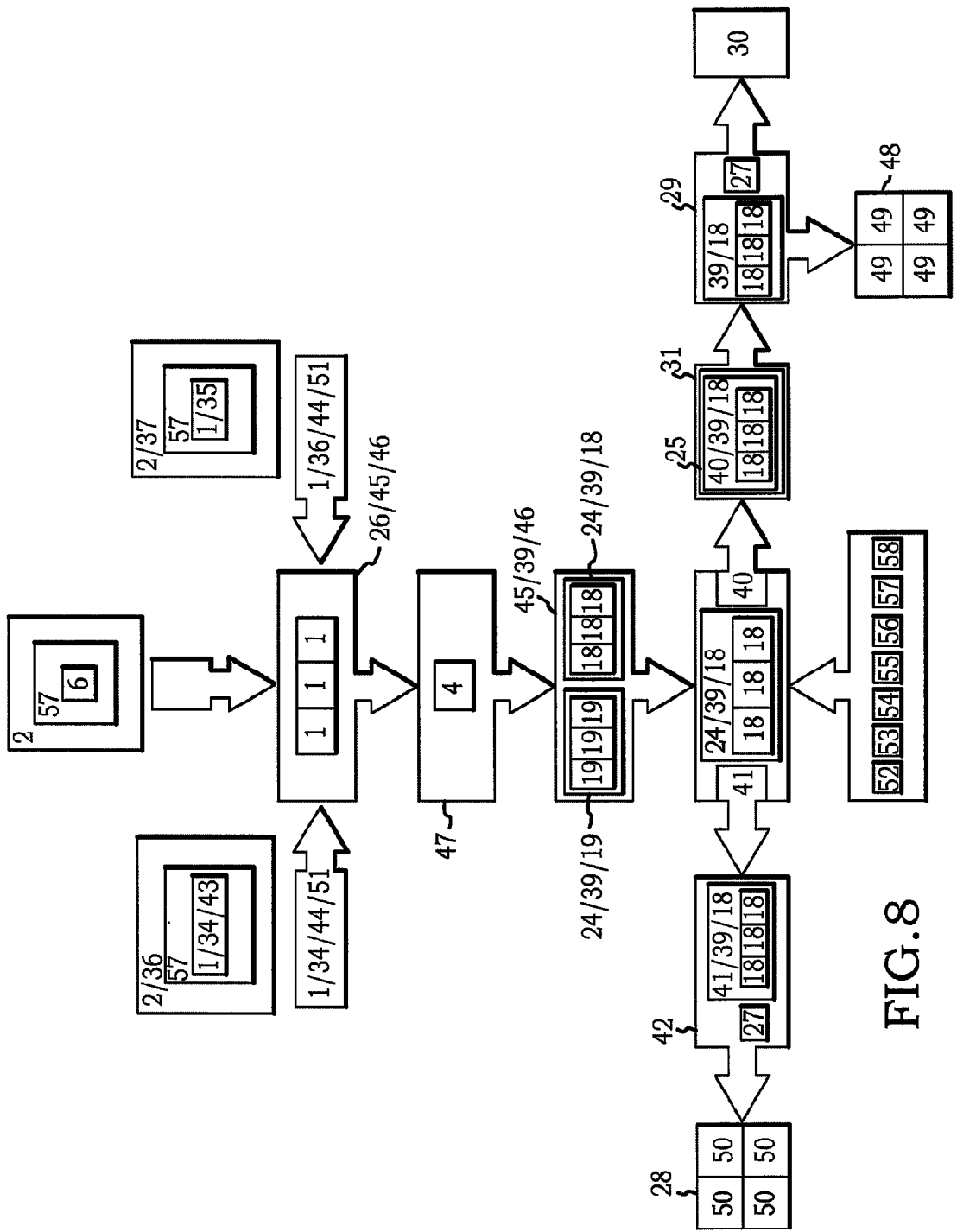
FIG. 8 is a block diagram which shows a particular method of how to make and use an embodiment of the inventive heterogeneous inseminate.

Now referring primarily to FIGS. 5, 6, 7 and 8, a univariate plot (or histogram) (32) (FIG. 5) and bivariate plot (33)(FIG. 6) (see also FIG. 7 showing an enlarged portion of bivariate plot shown in FIG. 6) can be generated using a flow cytometer (4) to separate or sort X-chromosome bearing sperm (18) from Y-chromosome bearing sperm (19) in a heterogeneous inseminate (24) prior achieved by combination of a first amount of sperm (34) with a second amount of sperm (35) or by combination of a plurality of amounts of sperm (1) from a corresponding first male animal (36), second male animal (37) or plurality of male animals (2) of the same species, as above described (also refer to FIG. 8). Because of differences in the same sperm characteristics (38) between a first amount of sperm (34) obtained from a first male animal (36) and a second amount of sperm (35) obtained from a second male animal (37), or between a plurality of amounts of sperm (1) obtained from a corresponding plurality of animals (2) of the same species, the separation, selection, or sorting (depending upon the method) of the X-chromosome bearing sperm (18)

from the Y-chromosome bearing sperm (19) in a heterogeneous inseminate (26) of unsorted sperm may not have been achieved prior to the instant invention.

Now referring to primarily to FIG. 8, particular embodiments of a sex-selected heterogeneous inseminate (39) and particular methods of preparing and using a sex-selected heterogeneous inseminate (39) are presented. A plurality of amounts of sperm (1) can be obtained from a corresponding plurality of male animals (2), each of the plurality of male animals (2) of the same species. The term "plurality of male animals" (2) can encompass two, three, four, five, six, or a greater number of male animals (2), as above described, for heterospermic insemination. The plurality of amounts of sperm cells (1) can be combined to achieve embodiments of the heterogeneous inseminate (26), as above described. The heterogeneous inseminate (26) can be divided to produce a plurality artificial insemination dosages (40) which can as to particular embodiments be contained one each in a corresponding number of artificial insemination straws (25), as above described. One or more of the artificial insemination doses (40) can be used for artificial insemination (31) of a female animal (29) of the same species for the production of in-vivo embryos (28) whether as single embryo pregnancies to generate offspring (30) for meat or animal replacement or multiple embryo pregnancies for multiple ovulation embryo transfer ("MOET") by subsequent flushing of a plurality of in-vivo embryos (48) from the female animal (29). As to other embodiments, the heterogeneous inseminate (26) can be divided or used as a number of in-vitro fertilization doses (41) for in-vitro fertilization (42) of one or more eggs (27) obtained from a female animal (29) to produce a plurality of in-vitro fertilized embryos (28).

Again referring primarily to FIG. 8, while a plurality of amounts of sperm (1) from a corresponding plurality of male animals (2) is shown; a particular illustrative example useful in understanding the numerous and varied embodiments of the invention can include a first amount sperm (34) obtained from a first male animal (36) and a second amount of sperm (35) obtained from a second male animal (37). The first male animal (36) and the second male animal (37) being of the same species. The first amount of sperm (34) obtained from the first male animal (36) can be combined with the second amount of sperm (35) obtained from the second male animal (37) to produce a particular embodiment of the heterogeneous inseminate (26).

As to particular embodiments of the heterogeneous inseminate (26), the first amount of sperm (34) can be an amount of infertile sperm (43) while the second amount of sperm (35) can have an initial level of fertility (44) outside of the heterogeneous inseminate (26). Upon combination of the first amount of sperm (34) (infertile sperm (43)) with the second amount of sperm (35), as concentration of the first amount of sperm (34) increases in the heterogeneous inseminate (26) as compared to the concentration of the second amount of sperm (35), the second amount of sperm (35) can exhibit by comparison to the initial level of fertility (44) an increased level of fertility (45) within the heterogeneous inseminate (26). Accordingly, the first amount sperm (34) can be sufficient in number or concentration within the heterogeneous inseminate (26) such that, the second amount of sperm (35) achieves by comparison to the initial level of fertility (44) an increased level of fertility (45).

As to other particular embodiments of the heterogeneous inseminate (26), the first amount of sperm (35) outside the heterogeneous inseminate (26) can have greater fertility than the initial level of fertility (44) of the second amount of sperm (35) outside of the heterogeneous inseminate (26). In combination, the second amount of sperm (35) can exhibit an increased level of fertility (45) within the heterogeneous inseminate (26). Accordingly, the heterogeneous inseminate (26) can afford a substantial advantage over conventional inseminates when the second amount of sperm (35) can confer desirable genetic traits, but has an initial level of fertility (44) outside of the heterogeneous inseminate (26) which may be unsuitable for use as an artificial insemination dosage (40) for the artificial insemination (31) of a female animal (29) or may be unsuitable for use as an in-vitro fertilization dose (41) for in-vitro fertilization (42) of eggs (27) obtained from a female animal (29). The comparably lesser initial level of fertility (44) of the second amount of sperm (35) outside of the heterogeneous inseminate (26) as compared to increased level of fertility (45) inside of the heterogeneous inseminate (26) may be due to a number of factors.

For example, there may be a lesser concentration of sperm outside of the heterogeneous inseminate (26), or the first amount of sperm (34) having greater initial level of fertility (44) may contribute, supplement or afford within the heterogeneous inseminate (26) a physical stimulus or chemical stimulus that acts upon the second amount of sperm (35) to generate the increased level of fertility (45) within the heterogeneous inseminate (26), or the second amount of sperm (35) may exhibit an increased level of motility (46) within the heterogeneous inseminate (26) as compared to outside of the heterogeneous inseminate (26), such greater motility can act to increase fertility of the second amount of sperm (35) in the heterogeneous inseminate (26).

Now referring primarily to FIG. 8 and FIG. 9, embodiments of the heterogeneous inseminate (3) can further include a first amount of sperm (34) and a second amount of sperm (35) (or a plurality of amounts of sperm (1)) from a corresponding first male animal (36) and a second male animal (37) (or plurality of male animals (2)) of the same species in which the first amount of sperm (35) or the second amount of sperm (36) or both the first amount of sperm (35) and the second amount of sperm (36) (or plurality of amounts of sperm (1)) can be sex-selected sperm (24).

Now referring primarily to FIG. 8, as to particular embodiments of the invention, the sex-selection process (47) above described and shown in FIGS. 1 and 2 for production of sex-selected sperm (24) can occur after combining the first amount of sperm (34) with the second amount of sperm (35) (or after combining a plurality of amounts of sperm (1)) to achieve the heterogeneous inseminate (26). After combination, the heterogeneous inseminate (26) can then undergo the sex selection process (47) resulting in a sex-selected heterogeneous inseminate (39) containing X-chromosome bearing sperm (18) and a sex-selected heterogeneous inseminate (39) containing Y-chromosome bearing sperm (19). The sex-selected heterogeneous inseminate (39) can contain X-chromosome bearing sperm (18) of the first amount of sperm (35) and the second amount of sperm (36) (or the plurality of amounts of sperm (1)) in similar proportion or concentration as in the original heterogeneous inseminate (26) to afford the substantial advantages above-described.

Similarly, the sex-selected heterogeneous inseminate (39) can contain Y-chromosome bearing sperm (19) of the first amount of sperm (34) and the second amount of sperm (35) (or plurality of amounts of sperm (1)) in similar proportion or concentration to the original heterogeneous inseminate (26) to afford the substantial advantages above-described. The sex-selected heterogeneous inseminate (39) containing X-chromosome bearing sperm (18) or the sex-selected heterogeneous inseminate (29) containing Y-chromosome bearing sperm (19) can be used in-vitro or in-vivo to fertilize the eggs (27) of a female animal (29) of the same species to produce sex-selected in-vivo embryos (48) or sex-selected offspring (30) or produce sex-selected in-vitro embryos (28) of a pre-selected sex. While FIGS. 8 and 9, show a sex-selected heterogeneous inseminate (39) containing only X-chromosome bearing sperm (18) of two or more male animals (2) being used for in-vitro (42) and in-vivo artificial insemination (31) of eggs (27); the invention is not so limited, and as above described embodiments of the sex-selected homogeneous inseminate (39) can include the X-chromosome bearing sperm (18) of two or more male animals (2) or the Y-chromosome bearing sperm (19) of two or more male animals (2).

Now referring primarily to FIG. 9, as to particular embodiments of the invention, the sex-selection process (47) for production of sex-selected sperm cells (24) can occur prior to combining the first amount of sperm (34) with the second amount of sperm (35) (or prior to combining the plurality of amounts of sperm (1)) to produce a sex-selected heterogeneous inseminate (39). As to these embodiments, each of the first amount of sperm (34) and the second amount of sperm (35) (or the plurality of amounts of sperm (1)) separately undergo the sex selection process (47) prior to combination. The first amount of sperm (34) can be separated into a subpopulation of X-chromosome bearing sperm (18) and into a subpopulation of Y-chromosome bearing sperm (19) as above described. Similarly, the second amount of sperm (35) (or each of the plurality of amounts of sperm (1)) can be separated into isolated subpopulations respectively containing X-chromosome bearing sperm (18) and Y-chromosome bearing sperm (19). An amount of the X-chromosome bearing sperm (18) obtained from the first amount of sperm (34) can be combined with an amount of the X-chromosome bearing sperm (18) obtained from the second amount of sperm (35) (or the X-chromosome bearing sperm (18) of a plurality of amounts of sperm (1) can be combined) to provide the sex-selected heterogeneous inseminate (39) containing X-chromosome bearing sperm (18).

Similarly, an amount of Y-chromosome bearing sperm (19) obtained from the first amount of sperm (34) can be combined with an amount of the Y-chromosome bearing sperm (19) obtained from the second amount of sperm (35) (or the Y-chromosome bearing sperm (18) of a plurality of amounts of sperm (1) can be combined) to provide a sex-selected heterogeneous inseminate (39) containing Y-chromosome bearing sperm (19).

The amount of the X-chromosome bearing sperm (18) obtained from the first amount of sperm (34) can be adjusted in relation to the amount of the X-chromosome bearing sperm (18) obtained from the second amount of sperm (35) (or the X-chromosome bearing sperm (18) obtained from each of the plurality of amounts of sperm (1) can be adjusted in relation to each other) to achieve a desired concentration or proportion of X-chromosome bearing sperm (18) from the first amount of sperm (34) and the second amount of sperm (35) (or the plurality of amounts of sperm (1)) in the sex-selected heterogeneous inseminate (39) to afford the substantial advantages above-described.

Similarly, the amount of the Y-chromosome bearing sperm (19) obtained from the first amount of sperm (34) can be adjusted in relation to the amount of the Y-chromosome bearing sperm (19) obtained from the second amount of sperm (35) (or the Y-chromosome bearing sperm (19) obtained from each of the plurality of amounts of sperm (1) can be adjusted in relation to each other) to achieve a desired concentration or proportion of Y-chromosome bearing sperm (19) from the first amount of sperm (34) and the second amount of sperm (35) (or the plurality of amounts of sperm (1)) in the sex-selected heterogeneous inseminate (26) to afford the substantial advantages above-described.

The sex-selected heterogeneous inseminate (39) containing X-chromosome bearing sperm (18) or the sex-selected heterogeneous inseminate (39) containing Y-chromosome bearing sperm (19) (or a particular proportion of X-chromosome bearing sperm (18) to Y-chromosome bearing sperm (19)) can be used for in-vitro fertilization (42) or in-vivo artificial insemination (31) to fertilize the eggs (27) of a female animal (29) of the same species to produce in-vivo sex-selected embryos (49) or in-vitro sex-selected embryos (50) of a pre-selected sex.

In regard to the increased level of fertility (45), particular embodiments of the invention can include a first amount of sperm (34) which outside of the heterogeneous inseminate (26) can have an initial level of fertility (44) of zero or nearly zero for a particular application, which can be due to insufficient numbers of sperm, insufficient motility of sperm, or insufficient physical or chemical stimuli which can be afforded within the homogeneous inseminate (26). Accordingly, once the threshold as to numbers of sperm, motility of sperm or the physical or chemical stimuli is achieved within the heterogeneous inseminate (26), the increased level of fertility (45) of the second amount of sperm (35) can be sufficient to allow successful fertilization of an egg (27) of a female animal (29) for that particular application, which would otherwise be unsuccessful or have a lesser fertility rate.

Understandably, the initial level of fertility (44) can be any level of fertility within a particular application, and the increased level of fertility (45) can be a comparable increase of fertility for that particular application. One measure by which initial level of fertility (44) and increased level of fertility (45) can be assessed is by measure of the initial level of motility (51) of the second amount of sperm (35) (or of any of the plurality of amounts of sperm (1)) outside of the heterogeneous inseminate (26) and the increased level of motility (46) of the second amount of sperm (36) (or of any of the plurality of amounts of sperm (1)) within the heterogeneous inseminate (26)). As to embodiments of the inventive heterogeneous inseminate (26) or sex-selected heterogeneous inseminate (393) the increase in the motility of the second amount of sperm (35) within the heterogeneous inseminate (26) (or sex-selected heterogeneous inseminate (39)) as compared to outside of the heterogeneous inseminate (26) can be in the range of between about 1% and about 30%. With respect to sex-selected heterogeneous inseminates (39) as one example, the initial level of motility (51) of sex-selected sperm (24) outside of the sex-selected heterogeneous inseminate (26) shortly after separation by a sex-selection process (47), such as flow cytometry, can be at or below 45% as compared to the increased level of motility (46) of the an substantially identical sample of sex-selected sperm (24) within the heterogeneous inseminate (26) of about 60% to about 70%.

For the purposes of this invention, the term "extender" refers to a solution that comes in contact with the plurality of sperm cells (1), the heterogeneous inseminate (26), or sex-selected sperm (24), or sex-selected heterogeneous inseminate (39), typically for the purpose of dilution or as a cryoprotectant. Typical examples of an extender (52) can contain one or more of: sodium citrate, Tris[hydroxymethyl]aminomethane (also referred to as "TRIS"), TES (N-Tris [Hydroxymethyl]methyl-2-aminoethanesulfonic acid), monosodium glutamate, HEPES medium such as HEPES buffered medium, HEPES buffered bovine gamete medium and particularly HBGM3 and can further contain cryoprotectants

(55) such as glycerol, dimethyl sulfoxide, ethylene glycol, propylene glycol; other organic substances such as egg yolk, an egg yolk extract, milk, a milk extract, casein, albumin, lecithin, bovine serum albumin, cholesterol; sugars such as the monosacharides, glucose, fructose, or mannose; detergents such as sodium dodecyl sulfate; antioxidants such butylated hydroxytoluene; capacitation facilitators such as alpha amylase, beta amylase, or beta glucuronidase; antibiotics such as tylosin, gentamicin, lincomycin, spectinomycin, linco-spectin (a combination of lincomycin and spectinomycin), penicillin, streptomycin, and ticarcillin; flow cytometer sheath fluids; and specifically without limiting the forgoing, particular extenders (52) referred to below as TRIS-A (53) and TRIS-B (54); although the inventive heterogeneous inseminate (26) or sex-selected heterogeneous inseminate (39) or methods of using the heterogeneous inseminate (26) or sex-selected heterogeneous inseminate (39) are not limited by the working examples which use TRIS-A (53) or TRIS-B (54) as an extender (52) to dilute concentration of the plurality of sperm cells (1), the sex-selected sperm cells (24) or embodiments of the heterogeneous inseminate (26) or sex-selected heterogeneous inseminate (39) which can be diluted by use of TRIS-A (53) or the use TRIS-B (54) as a cryoprotectant (55). The use of TRIS-A (53) or the use of TRIS-B (54) is described in detail as an illustrative example of the numerous and varied extenders that can be used with embodiments of the invention as diluents and cryoprotectants (55).

For the purposes of this invention the term "TRIS-A" refers to an extender (52) having the formulation in Table 7.

TABLE 7

| TRIS-A Extender. | |
| --- | --- |
| TRIS | 200 mM |
| Citric Acid | 65 mM |
| Fructose | 56 mM |
| Egg Yolk* | 20% by volume |
| Hydrochloric Acid addition to pH 6.8 | |

*Egg Yolk can be clarified by winterization process to remove certain particulates and fats.

The formulation of TRIS-A set out in Table 7 can be from application to application of the invention modified to increase viability or reduce damage to the plurality of sperm cells (1), the heterogeneous inseminates (26) or sex-selected heterogeneous inseminates (39) and the above formulation is provided as a non-limiting example of a numerous and wide variety of similar extenders (52) which are suitable for use in making or using the embodiments of the invention. See also, Yassen, A. M. and Foote, R. H., Freezability of Bovine Spermatozoa in Tris-Buffered Yolk Extenders Containing Different Levels of Tris, Sodium, Potassium and Calcium Ions, J. Dairy Science, Vol. 50, No. 6, 887-892 (1966), hereby incorporated by reference in the entirety herein. Extenders (52) in general and specifically the particular extender TRIS-A (53) can further include one or more antibiotics (56) as above described or consistent with animal health regulations of any particular jurisdiction. Also, the description of TRIS-A (53) is not intended to be limiting with respect to the wide variety of extenders (52) which can be utilized in making and using certain embodiments of the invention, as described above.

For the purposes of this invention the term "TRIS-B" refers to an extender (52) having the formulation in Table 8.

TABLE 8

| TRIS-B Extender. | |
| --- | --- |
| TRIS | 200 mM |
| Citric Acid | 65 mM |
| Fructose | 56 mM |
| Egg Yolk* | 20% by volume |
| Glycerol | 12% by volume |
| Hydrochloric Acid addition to pH 6.8 | |

*Egg Yolk can be clarified by winterization process to remove certain particulates and fats.

The formulation of TRIS-B (54) set out in Table 8 can from application to application of the invention be modified to increase viability or reduce damage to the plurality of sperm cells (1), the heterogeneous inseminates (26) or sex-selected heterogeneous inseminates (39) and the above formulation is provided as a non-limiting example of a numerous and wide variety of similar extenders (52) which are suitable for use in making or using the embodiments of the invention. Again see for example, Yassen, A. M. and Foote, R. H., Freezability of Bovine Spermatozoa in Tris-Buffered Yolk Extenders Containing Different Levels of Tris, Sodium, Potassium and Calcium Ions, J. Dairy Science, Vol. 50, No. 6, 887-892 (1966). Extenders (52) in general and specifically the particular extender TRIS-B (54) can further include one or more antibiotics (56) as above described or consistent with animal health regulations of any particular jurisdiction. Additionally, while TRIS-B (54) of the particular formulation set out in Table 8 uses glycerol as a cryoprotectant (55) the invention is not so limited. Also, the description of TRIS-B (54) is not intended to limiting with respect to the wide variety of extenders (52) which can be utilized in making and using certain embodiments of the invention, as described above.

Again referring primarily to FIGS. 8 and 9, as to particular embodiments, the plurality of sperm cells (1), the first amount of sperm (34) and the second amount of sperm (35) (whether or not sex-selected sperm (24)), the resulting heterogeneous inseminate (26) or sex-selected heterogeneous inseminate (39) can further include an amount of seminal fluid (57), which may be may be cell free semen (58) prepared by removal of entrained sperm (1) which may be diluted with an extender (52). Removal of entrained sperm (1) from the seminal fluid (57) can be achieved by centrifugation of semen at about 500×g for about 15 min. The seminal fluid (57) decanted and centrifuged a second time at 500×g for about 15 min.

Again referring to FIGS. 8 and 9, embodiments of the homogeneous inseminate (26) or sex-selected homogeneous inseminate (39) can further include a particular dosage form. As one non-limiting example, the dosage form for artificial insemination (31) of cattle can be a one-quarter cubic centimeter (0.25 cc) artificial insemination straw (25) which contains the heterogeneous inseminate (26) or sex-selected heterogeneous inseminate (39). While the FIGS. 8 and 9 only show a sex-selected heterogeneous inseminate (39) contained in the artificial insemination straw (25); the invention is not so limited and dosage forms whether in the form of an artificial insemination straw (25) or otherwise can contain a heterogeneous inseminate (26), a sex-selected heterogeneous inseminate (39), or can contain a combination of both a heterogeneous inseminate (26) and sex-selected heterogeneous inseminate (29).

Again referring to FIGS. 8 and 9, dosage forms of the heterogeneous inseminate (26) and the sex-selected heterogeneous inseminate (39) can be produced by similar steps or procedures as conventional insemination or sex-selected insemination dosage forms; however, the use of the heterogeneous inseminate (26) or sex-selected heterogeneous inseminate (39) can by comparison provide artificial insemination dosages (40) or in-vitro fertilization dosages (41) which exhibit an increased level of motility (46) or have an increased level of fertility (45).

Now referring primarily to FIG. 8, as one non-limiting example, a bovine embodiment of a sex-selected heterogeneous inseminate (39) can be produced by obtaining a first amount of sperm (34) (whether fresh or cryopreserved) of a first male animal (36) and obtaining a second amount of sperm (35) (whether fresh or cryopreserved) of a second male animal (37) of the same species of bovine male animal (or by obtaining a plurality of amounts of sperm (1) from a plurality of male animals (2) of the same species). The first amount of sperm (34), the second amount of sperm (35), or the plurality of amounts of sperm (1) can each be separately suspended in an amount of TRIS-A (53) (or other extender (52)) and then centrifuged in range of about 500 rounds per minute ("rpm") and about 5,000 rpm for a period of time in a range of between about one minute and about ten min. The supernatant can be decanted from each of the amounts of sperm (34)(35)(1). Each of the amounts of sperm (34)(35)(1) can be extended with TRIS-A (53) (or other extender (52)) to achieve a concentration which allows each the extended first amount of sperm (34), second amount of sperm (35), or plurality of amounts of sperm (1) to be combined to produce a heterogeneous inseminate (26) each of the first amount of sperm (34), the second amount of sperm (35, or each of a plurality of amounts of sperm (1) at a desired concentration within the heterogeneous inseminate (26).

As a non-limiting example, the concentration of the first amount of sperm (34) and the second amount of sperm (35) within the heterogeneous inseminate (26) can be about 75 million sperm per milliliter. The concentration of the first amount of sperm (34) in the heterogeneous inseminate (26) can be about 55 million sperm per milliliter and the concentration of the second amount of sperm (35) in the heterogeneous inseminate (26) can be about 20 million sperm per milliliter; however the invention is not so limited, and the concentration of the first amount of sperm (34) or the second amount of sperm (35) or a plurality of amounts of sperm (1) within the heterogeneous inseminate (26) can be at any predetermined concentration depending upon the application, which as to certain embodiments can provide about equal concentration of each of a plurality of amounts of sperm (1) from a corresponding plurality of animals (2) or can provide unequal concentration as to a plurality of amounts of sperm (1) from a corresponding plurality of animals (2).

The heterogeneous inseminate (3) can then be incubated in about 38 micromolar Hoechst 33342 at about 75 million sperm/ml in the extender (52) for 1 hour at about 34° C.; although other stains or staining conditions can be utilized as above described, to achieve staining of the DNA of the first amount of sperm (34), the second amount of sperm (35), or the plurality of amounts of sperm (1) within the heterogeneous inseminate (26) for separation into subpopulations containing X-chromosome bearing sperm (18) and Y-chromosome bearing sperm (19), as above described or otherwise. As an example, the stained sperm contained in the heterogeneous inseminate (26) can be interrogated by laser excitation at 351 and 364 nm at 150 mW and based on the difference in fluorescent emission be separated into subpopulations of X-chromosome bearing sperm (18) and Y-chromosome bearing sperm (19) using a MOFLO flow cytometer (4) (or other makes or models of flow cytometers or multiple flow channel apparatus), as above described. The subpopulations of X chromosome-bearing sperm (18) and Y-chromosome bearing sperm (19) of about 90% purity as verified by resort analysis can be collected at between about 1,500 live sperm/second and about 5,000 live sperm/second into 2-ml Eppendorf tubes containing 100 micromolar Cornell Universal Extender (CUE) with 20% egg yolk.

Collected sex-selected sperm (24) can be centrifuged at about 600×g for 10 min and resuspended in TRIS B (54) to a concentration of about 2 million motile sex-selected sperm/mL to provide an embodiment of a sex-selected heterogeneous inseminate (39). The sex-selected heterogeneous inseminate (39) can be cooled to about 5° C. over about 75 min and artificial insemination dosages (40) transferred into 0.25-cc artificial insemination straws (25) (about 150 microliters to about 200 microliters per straw). Straws (25) can be cryopreserved, as above described by conventional procedures, or transported at about 3° C. to about 5° C. for use in artificial insemination (31) of female animals (29). Artificial insemination dosages (40) and control dosages can be inseminated using side-opening blue sheaths (IMV), one half of each straw into each uterine horn of female animal (29) of the same bovine species (total of about $3.5 \times 10^5$ sex-selected sperm per artificial insemination dosage or about 250,000 sex-selected sperm from the first amount of sperm (34) and about 50,000 sex-selected sperm from the second amount of sperm (35)). Understandably, the respective concentration of sex-selected sperm (24) in an artificial insemination dosage (40) between a first amount of sperm (34), a second amount of sperm (35), or a plurality of amounts of sperm (1) can be adjusted by adjusting the initial concentration of the a sex-selected heterogeneous inseminate (39) prior to division into the corresponding plurality of artificial insemination dosages (40) or other dosage forms.

Now referring primarily to FIG. 9, as a general non-limiting example, a bovine embodiment of a sex-selected heterogeneous inseminate (39) can be produced by obtaining a first amount of sperm (34) as sex-selected sperm cells (24) (whether fresh or cryopreserved) of a first male animal (36) of a bovine species. The first amount of sperm (34) can be suspended in an amount of TRIS-A (53) (or other extender (52)) and then centrifuged in range of about 500 rounds per minute ("rpm") and about 5,000 rpm for a period in a range of between about one minute and about ten min. The supernatant can be decanted. The first amount of sperm (34) can be extended with TRIS-A (53) extender (or other extender (52)) to achieve a concentration of the extended first amount of sperm (34) of about four times greater than the expected concentration of the second amount of sperm (35), or other concentration depending upon the application. The four times concentration of the first amount of sperm (34) in TRIS-A (54) (or other extender (53)) can be for example a concentration in a range of about 3.2 million sperm cells/mL and about 128 million sperm cells/mL.

The extended first amount of sperm (34) (sex-selected sperm (24)) can be cooled to a temperature in a range of about 4 degrees Celsius ("° C.") and about 5° C. The cooled extended first amount of sperm (34) can be held at this temperature to allow the membranes of the first amount of sperm (34) to move toward equilibrium or equilibrate with the TRIS-A (53) (typically a period of about 90 min or as to certain embodiments not less than 90 min). The cooled extended first amount of sperm (34) can be held in this condition not to exceed a length of time in which the sperm cells (34) remain viable or capable of fertilizing an egg (27) of a female animal (29) of the same species as the first and second male animals (36)(37). Typically, the period of time held will not exceed 12 h.

A second amount of sperm (35) as sex-selected sperm cells (24) (fresh or cryopreserved) can be obtained of a second male animal (37) of the same bovine species. The second amount of sperm (35) can be suspended in an amount of TRIS-A (53) (or other extender (52)) and then centrifuged in range of about 500 rounds per minute ("rpm") and about 5,000 rpm for a period in a range of between about one minute and about ten min. The supernatant can be decanted and the pellet containing the second amount of sperm (35) can be suspended in an amount of TRIS-A (53) to achieve a concentration of the second amount of sperm (35) of about one-fourth that of the first amount of sperm (34). Accordingly, the second amount of sperm (35) as a non-limiting example can have a concentration in a range of about 800,000 sperm per milliliter and about 32 million sperm per milliliter depending upon various factors such as the species of the second male animal (37), the scarcity of the sperm, the fertility of the sperm, the dosage form, the method of insemination (whether artificial insemination (31) or in-vitro fertilization (42)), whether for multiple ovulation embryo transfer or single ovulation single embryo production, the female animal (29) of the same species as the first and second male animal (36)(37) being inseminated, or the like.

The extended second amount of sperm (35) can be cooled to a temperature in a range of about 4° C. and about 5° C. The cooled extended second amount of sperm (35) can be held at this temperature to allow the membranes of the second amount of sperm (35) to move toward equilibrium or equilibrate with the TRIS-A (53) (typically a period of about 90 min or as to certain embodiments not less than 90 min).

About equal volumes of the cooled extended first amount of sperm (34) (sex-selected sperm (24)) and the cooled extended second amount of sperm (35) (sex-selected sperm (24)) can be combined to achieve two times greater concentration of the first amount of sperm (34) with respect to the final concentration of the second amount of sperm (35) contained in the resulting heterogeneous sex-selected inseminate (39).

To the resulting sex-selected heterogeneous inseminate (39) about an equal volume of TRIS-B (54) (containing between about 12% and 20% glycerol) can be added and the combination cooled to temperature in a range of about 4° C. and about 5° C. The cooled extended sex-selected heterogeneous inseminate (39) can be held at this temperature to allow the membranes of the sperm cells (1)(24) to move toward equilibrium or equilibrate with the TRIS-B (54) (typically a period in the range of about 30 min and about 90 min or as to certain embodiments not less than 90 min). The cooled sex-selected heterogeneous inseminate (39) can be held in this condition not to exceed a length of time in which the sex-selected sperm cells (24) remain viable or capable fertilizing an egg (27) of a female (29) of the same species as the male animals (2).

The cooled sex-selected heterogeneous inseminate (39) can be handled by normal procedures utilized for producing artificial insemination doses (40). Accordingly, as to certain embodiments, the cooled sex-selected heterogeneous inseminate (39) can be aliquoted into 0.25 cc artificial insemination straws (25) (about 100 microliters to about 200 microliters per straw). The 0.25 cc artificial insemination straw (25) can contain an amount of the sex-selected heterogeneous inseminate (39) which contains sex-selected sperm (24) from the second amount of sperm (35) in the range of about 50,000 and about 2 million and from the first amount of sperm (14) in the range of about 200,000 and about 8 million. However, a greater or lesser number of the first amount of sperm (34) and the second amount of sperm (35) can be included in each 0.25 cc artificial insemination straw (25) by adjusting the initial concentrations of the first amount of sperm (34) and the second amount of sperm (35) with the total number of sex-selected sperm (24) in each artificial insemination dosage (40) of the instant example being in the range of about 250,000 and about 10 million sex-selected sperm (24).

The sex-selected heterogeneous inseminate (39) can used for artificial insemination (31) to fertilize the egg(s) (27) of a female animal (29) of the same species as the first and second male (36)(37) for the production of sex-selected in-vivo embryo (49) whether as single embryo pregnancies to generate offspring (30) for meat or animal replacement or multiple embryo pregnancies for MOET by subsequent flushing of a plurality of sex-selected embryos (49). Alternately, the sex-selected heterogeneous inseminate (39) can be used in-vitro fertilization procedures (42) to fertilize eggs (27) obtained from a female animal (297) of the same species to produce in vitro sex-selected in-vitro fertilized embryos (50).

The use of heterogeneous sex-selected inseminate (39) can result in increased fertility rates. As one non-limiting example, where a plurality of amounts of sperm (1) are processed in accordance with either the method shown in FIG. 8 or FIG. 9 and as described above to produce a sex-selected heterogeneous inseminate (39), the sex-selected heterogeneous inseminate (39) can have an increased level of fertility (45) overall as compared to any initial level of fertility (44) for any one of the plurality of amounts of sperm (1) outside of the sex-selected heterogeneous inseminate (39).

As a second non-limiting example, where a plurality of amounts of sperm (1) from a corresponding plurality animals (2) of the same species are processed as above described to provide a sex-selected heterogeneous inseminate (39) which includes at least one amount of sex-selected sperm (24) having a comparably greater initial level of fertility (45) to one or more amounts of sex-selected sperm (24) having a lesser initial level of fertility (44) outside of the sex-selected heterogeneous inseminate (26), the one or more of the amounts of sex-selected sperm (24) within the sex-selected heterogeneous inseminate (39) can exhibit an increased level of fertility (45) which can exceed the initial level of fertility (44) of the amount of sex-selected sperm (24) having the greater initial level of fertility (45).

As a third non-limiting example, the seminal fluid (57) of one or more amounts of sex-selected sperm (24) which exhibit a comparably greater initial level of fertility (45) outside of the sex-selected heterogeneous inseminate (26) can be stored as an amount cell free semen (58) and added back into the sex-selected heterogeneous inseminate (39) processed in accordance with either the method shown in FIG. 8 or FIG. 9 and as described above to produce a sex-selected heterogeneous inseminate (39). The amount of cell free semen (58) in a sex-selected heterogeneous inseminate (39) can be in the range of zero cell free semen to about 2 parts cell free semen (58) to one part sex-selected heterogeneous insemination (39). The concentration of the sex-selected sperm (24) can be adjusted as above-described to afford the desired concentration of sex-selected sperm (24) in an artificial insemination dosage (40) or an in-vivo insemination dosage (40).

The invention can further include a mammal produced in accordance with any of the above described embodiments of the invention, or can include a mammal of predetermined sex in accordance with the various embodiments of the invention that provide sperm cell insemination samples having an enriched population of either X-chromosome bearing sperm cells or enriched population of Y-chromosome bearing sperm cells, or a mammal produced in accordance with any embodiment of the invention in which a sperm cell insemination sample containing a low number of sperm cells compared to the typical number used to inseminate that particular species of mammal is used, or elk progeny produced in accordance with the invention as described above.

As can be easily understood from the foregoing, the basic concepts of the present invention may be embodied in a variety of ways. It involves both a sperm cell process system including both techniques as well as devices to accomplish sperm cell processing. In this application, various sperm cell processing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this nonprovisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which will be included in a full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "flow-sorter" should be understood to encompass disclosure of the act of "flow-sorting"—whether explicitly discussed or not—and, conversely, were there effectively disclosure of the act of "flow-sorting", such a disclosure should be understood to encompass disclosure of a "flow-sorter" and even a "means for flow-sorting" Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the sperm cell processing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed, and xi) each potentially dependent claim or concept as a dependency on each and every one of the independent claims or concepts presented. In this regard it should be understood that for practical reasons and so as to avoid adding potentially hundreds of claims, the applicant may eventually present claims with initial dependencies only. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

For the purposes of this invention, the term "animal" means a species of mammal, ayes, or fish from which semen containing an amount of sperm is produced by a male animal of the species and an egg is produced by the female animal of the species and a mammal, without limiting the general forgoing statement, can be a species of: horse, cattle, camel, deer, pig, sheep, goat, dog, cat, lion, whale, dolphin, porpoise, seal, hare, rabbit, elephant, mouse, rat, or the like, and a fish, without limiting the general forgoing statement, can be a species of: salmon, tuna, sturgeon, halibut, catfish, or the like, and a bird, without limiting the general forgoing statement can be a species of: chicken, turkey, eagle, falcon, ostrich, emu, duck, goose, or the like.

For the purposes of this invention the term "semen" means seminal fluid which may contain sperm (also referred to as "spermatozoa") secreted by the gonads of a male animal which can be collected from the male animal by a variety of methods such as use of an artificial vagina, manual manipulation of the penis, electrical manipulation of the anus, or the like.

For the purposes of this invention the term "sperm" or "sperm cell" means the haploid cell that is the garnet of a male animal which may join an egg (also referred to as "ovum") to produce a zygote and broadly encompasses infertile sperm, sperm having a comparably lesser or a comparably greater fertility between a first amount of sperm obtained from a first animal and a second amount of sperm obtained from a second animal and which may be obtained in the form of a raw ejaculated semen, frozen semen, as sperm separated from the semen and contained in an extender or diluent, or as sex-selected sperm.

For the purposes of this invention the term "sex-selected sperm" means sperm which have been separated, regardless as to the method of separation, into subpopulations containing X-chromosome bearing sperm and Y-chromosome bearing sperm having a purity in the range of about 70 percent ("%") and about 100%.

For the purposes of this invention, the term "inseminate" or "insemination sample" is intended to broadly encompass an amount of sperm whether contained in semen or other extender or diluent which can be utilized to fertilize the eggs of a female animal whether in-vitro or in-vivo and without limitation to the general forgoing statement can be an amount of sperm whether or not sex-selected introduced or injected into the reproductive tract of a female animal whether by artificial insemination procedures or otherwise, or utilized in in-vitro fertilization procedures.

For the purposes of this invention, the term "heterogeneous inseminate" means an inseminate in the form of a combination of a first amount sperm obtained from a first male animal and a second amount of sperm obtained from a second male animal, the first animal and the second male animal being of the same species; however, the invention is not so limited and a plurality of amounts of sperm obtained from a corresponding plurality of male animals of the same species can be combined to produce various embodiments of the heterogeneous inseminate.

For the purposes of this invention, the term "sex-selected heterogeneous inseminate" means a heterogeneous inseminate having the first amount of sperm obtained from a first male animal and the second amount of sperm obtained from a second male animal (or a plurality of amounts of sperm obtained from a plurality of animals) which are processed, whether prior to combination or after combination, such that the first amount of sperm and the second amount of sperm (or the plurality of amounts of sperm) contained in a heterogeneous inseminate are sex-selected sperm.

For the purposes of this invention, the term "fertility" means the fertilization rate determined for an artificial insemination procedure as the number of pregnancies achieved within a population of inseminated female animals divided by the total number inseminated female animals and multiplied by 100 or determined for in-vitro fertilization procedure as the number of embryos (greater than or equal to two cells) divided by the sum of the embryos and oocytes recovered and multiplied by 100.

For the purposes of this invention, the term "motility" means moving sperm in an inseminate or sample of sperm.

For the purposes of this invention, the term "infertile" means as to any particular procedure incapable of fertilizing an egg of a female animal.

We claim:

1. A method of producing a heterogeneous inseminate, comprising:
   obtaining a first amount of sperm of a first animal;
   obtaining a second amount of sperm of a second animal, said first animal and said second animal of the same species, wherein said first amount of sperm of said first animal or said second amount of sperm of said second animal comprises sex-selected sperm;
   combining said first amount of sperm of said first animal with said second amount of sperm of said second animal; and
   adjusting said first amount of sperm of said first animal in said heterogeneous inseminate to provide a concentration sufficient to increase motility of said second amount of sperm of said second animal in said heterogeneous inseminate.

2. The method of producing a heterogeneous inseminate of claim 1, wherein said first amount of sperm of said first animal has a greater fertility than said second amount of sperm.

3. The method of producing a heterogeneous inseminate of claim 1, wherein a concentration of said first amount of sperm of said first animal in said heterogeneous inseminate has a greater concentration than said second amount of sperm of said second animal.

4. The method of producing a heterogeneous inseminate of claim 1, wherein said first amount of sperm of said first animal comprises an amount of infertile sperm.

5. The method of producing a heterogeneous inseminate of claim 1, wherein said first amount of sperm and said second amount of sperm each comprise said sex-selected sperm.

6. The method of producing a heterogeneous inseminate of claim 5, further comprising selecting sex of said first amount of sperm of said first animal and selecting sex of said second amount of sperm of said second animal prior to said step of combining said first amount of sperm of said first animal with said second amount of sperm of said second animal.

7. The method of producing a heterogeneous inseminate of claim 5, further comprising selecting sex of said first amount of sperm of said first animal and said second amount of sperm of said second animal after said step of combining said first amount of sperm of said first animal with said second amount of sperm of said second animal.

8. The method of producing a heterogeneous inseminate of claim 5, wherein said first amount of sperm of said first animal or said second amount of sperm of said second animal comprises frozen-thawed sperm.

9. The method of producing a heterogeneous inseminate of claim 5, wherein said species of animal is selected from the group consisting of: a mammal, an aves, and a fish.

10. The method of producing a heterogeneous inseminate of claim 5, wherein said species of animal is a bovine mammal and wherein said second amount of sperm of said second animal in said heterogeneous inseminate has a concentration of between about $2 \times 10^4$ sperm per milliliter and about $4 \times 10^6$ sperm per milliliter and said first amount of sperm of said first animal in said heterogeneous inseminate has a concentration of between $2\times10^7$ sperm per milliliter and about $8\times10^7$ sperm per milliliter.

11. The method of producing a heterogeneous inseminate of claim 10, further comprising producing said heterogeneous inseminate in a dosage form having a volume between one-tenth milliliter and about one milliliter contained in an artificial insemination straw.

12. The method of producing a heterogeneous inseminate of claim 11, further comprising freezing said dosage form having a volume of between about one-tenth milliliter and about one milliliter contained in said artificial insemination straw.

13. The method of producing a heterogeneous inseminate of claim 1, wherein said adjusting of said first amount of sperm of said first animal in said heterogeneous inseminate increases fertility of said second amount of sperm of said second animal, and wherein fertility is determined as the ability to fertilize an egg of said species of animal.

14. The method of producing a heterogeneous inseminate of claim 1, further comprising admixing an amount of cell free seminal fluid prepared from an amount of semen having a greater initial level of fertility than said level of fertility of said first amount of sperm and/or said second amount of sperm.

15. A method of producing a heterogeneous inseminate, comprising the steps of:
obtaining a first amount of sperm of a first animal;
obtaining a second amount of sperm of a second animal, said first animal and said second animal of the same species, wherein said first amount of sperm of said first animal or said second amount of sperm of said second animal comprises sex-selected sperm;
combining said first amount of sperm of said first animal with said second amount of sperm of said second animal; and
adjusting said first amount of sperm of said first animal in said heterogeneous inseminate to provide a concentration sufficient to increase fertility of said second amount of sperm of said second animal in said heterogeneous inseminate.

16. The method of producing a heterogeneous inseminate of claim 15, wherein said first amount of sperm of said first animal has a greater fertility than said second amount of sperm.

17. The method of producing a heterogeneous inseminate of claim 15, wherein a concentration of said first amount of sperm of said first animal in said heterogeneous inseminate has a greater concentration than said second amount of sperm of said second animal.

18. The method of producing a heterogeneous inseminate of claim 15, wherein said first amount of sperm of said first animal comprises an amount of infertile sperm.

19. The method of producing a heterogeneous inseminate of claim 15, wherein said first amount of sperm and said second amount of sperm each comprise said sex-selected sperm.

20. The method of producing a heterogeneous inseminate of claim 19, further comprising selecting sex of said first amount of sperm of said first animal and selecting sex of said second amount of sperm of said second animal prior to said step of combining said first amount of sperm of said first animal with said second amount of sperm of said second animal.

21. The method of producing a heterogeneous inseminate of claim 19, further comprising selecting sex of said first amount of sperm of said first animal and said second amount of sperm of said second animal after said step of combining said first amount of sperm of said first animal with said second amount of sperm of said second animal.

22. The method of producing a heterogeneous inseminate of claim 19, wherein said first amount of sperm of said first animal and/or said second amount of sperm of said second animal comprises frozen-thawed sperm.

23. The method of producing a heterogeneous inseminate of claim 15, wherein said species of animal is selected from the group consisting of: a mammal, an ayes, and a fish.

24. The method of producing a heterogeneous inseminate of claim 15, wherein said species of animal is a bovine mammal and wherein said second amount of sperm of said second animal in said heterogeneous inseminate has a concentration of between about $2\times10^4$ sperm per milliliter and about $4\times10^6$ sperm per milliliter and said first amount of sperm of said first animal in said heterogeneous inseminate has a concentration of between $2\times10^7$ sperm per milliliter and about $8\times10^7$ sperm per milliliter, and wherein said second amount of sperm comprises sex-selected sperm.

25. The method of producing a heterogeneous inseminate of claim 24, wherein said mammal comprises a bovine mammal and further comprising the step of producing said heterogeneous inseminate in a dosage form having a volume of between about one-tenth milliliter and about one milliliter contained in an artificial insemination straw.

26. The method of producing a heterogeneous inseminate of claim 25, further comprising freezing said dosage form having a volume of between about one-tenth milliliter and about one milliliter contained in said artificial insemination straw.

27. The method of claim 15, wherein fertility is determined as the ability to fertilize an egg of said species of animal.

28. The method of producing a heterogeneous inseminate of claim 15, further comprising admixing an amount of cell free seminal fluid prepared from an amount of semen having a greater initial level of fertility than said level of fertility of said first amount of sperm and/or said second amount of sperm.

* * * * *

UNITED STATES PATENT AND TRADEMARK OFFICE
CERTIFICATE OF CORRECTION

PATENT NO.       : 8,486,618 B2                                 Page 1 of 1
APPLICATION NO.  : 13/185400
DATED            : July 16, 2013
INVENTOR(S)      : John L. Schenk et al.

It is certified that error appears in the above-identified patent and that said Letters Patent is hereby corrected as shown below:

In the Claims

Claim 23, Column 32, line 24, "ayes" should be changed to --aves--

Signed and Sealed this
Twenty-fifth Day of March, 2014

Michelle K. Lee
*Deputy Director of the United States Patent and Trademark Office*